United States Patent
Ackermann et al.

(10) Patent No.: US 7,253,192 B2
(45) Date of Patent: Aug. 7, 2007

(54) PHENYL DERIVATIVES COMPRISING AN ACETYLENE GROUP

(75) Inventors: Jean Ackermann, Riehen (CH); Johannes Aebi, Basel (CH); Alfred Binggeli, Binningen (CH); Uwe Grether, Efringen-Kirchen (DE); Bernd Kuhn, Liestal (CH); Hans-Peter Maerki, Basel (CH); Markus Meyer, Neuenburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 52 days.

(21) Appl. No.: 11/172,321

(22) Filed: Jun. 30, 2005

(65) Prior Publication Data
US 2006/0004091 A1    Jan. 5, 2006

(30) Foreign Application Priority Data
Jul. 1, 2004 (EP) .................................. 04103116
Mar. 14, 2005 (EP) .................................. 05101986

(51) Int. Cl.
*A61K 31/44* (2006.01)
*C07C 69/66* (2006.01)
*C07D 413/00* (2006.01)
*C07D 417/00* (2006.01)

(52) U.S. Cl. ................... 514/342; 560/174; 546/268.7; 546/344; 544/124

(58) Field of Classification Search ................ 560/174, 560/751; 546/268.7, 344; 514/342; 544/124
See application file for complete search history.

(56) References Cited

U.S. PATENT DOCUMENTS 5,731,454 A * 3/1998 Abraham et al. .............. 560/43

FOREIGN PATENT DOCUMENTS

| EP | 1 380 562 A1 | 1/2004 |
| WO | WO 03/084916 A2 | 10/2003 |
| WO | WO 2004/002253 A1 | 3/2004 |

OTHER PUBLICATIONS

Hcaplus 142:35748.*

Martens et. al., Metabolic and Additional Vascular Effects of Thiazolidinediones, Drugs 2002:62(10), 1463-1480.*
Sewter et. al., PPARy and the thiazolidinediones: molecular basis for a treatment of 'Syndrome X'?, pp. 239-248.*
Oliver et al; Proc Nat Acad Sci USA 2001; 98: 5306-11.
Guerre-Millo et al; J Biol Chem 2000; 275: 16638-16642.

* cited by examiner

Primary Examiner—D. Margaret Seaman
Assistant Examiner—Binta Robinson
(74) Attorney, Agent, or Firm—George W. Johnston; Dennis P. Tramaloni; Samuel H. Megerditchian

(57) ABSTRACT

This invention is concerned with compounds of the formula I:

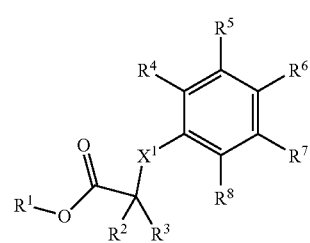

wherein one of $R^5$, $R^6$ and $R^7$ is

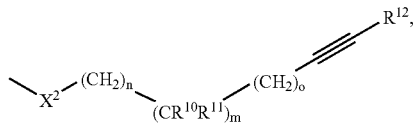

and $X^1$, $X^2$, $R^1$ to $R^{12}$, m, n and o are as defined in the description, and pharmaceutically acceptable salts and/or esters thereof. The invention further relates to pharmaceutical compositions containing such compounds, to a process for their preparation and to their use for the treatment and/or prevention of diseases which are modulated by PPARδ and/or PPARα agonists.

23 Claims, No Drawings

PHENYL DERIVATIVES COMPRISING AN ACETYLENE GROUP

FIELD OF THE INVENTION

The present invention is directed to novel phenyl derivatives comprising an acetylene group of the formula I:

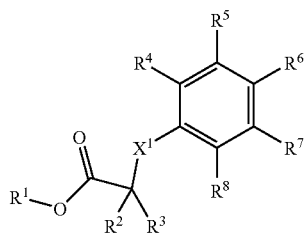

and pharmaceutically acceptable salts and esters thereof.

It has been found that compounds of formula I are useful as lipid modulators and insulin sensitizers. In particular, compounds of formula I are PPAR activators.

All documents cited or relied upon below are expressly incorporated herein by reference.

BACKGROUND OF THE INVENTION

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described which are PPARα, PPARδ (also known as PPARβ), and PPARγ. PPARδ is ubiquitously expressed. PPARα is predominantly expressed in the liver, kidney and heart. There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose- and lipid-homeostasis and metabolism, energy balance, cell differentiation, inflammation and cardiovascular events.

Approximately half of all patients with coronary artery disease have low concentrations of plasma HDL cholesterol. The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels. The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol>240 mg/dl is 37% in diabetic men and 44% in women. The respective rates for LDL-C>160 mg/dl are 31% and 44%, respectively, and for HDL-C<35 mg/dl 28% and 11%, respectively.

Diabetes is a disease in which a patient's ability to control glucose levels in blood is decreased because of partial impairment in response to the action of insulin. Type II diabetes (T2D) is also called non-insulin dependent diabetes mellitus (NIDDM) and afflicts 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2D is a cardiovascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance.

A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (Actos™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients. Therefore, new, more efficacious drugs with greater safety and lower side effects are urgently needed. Recent studies provide evidence that agonism of PPARδ would result in compounds with enhanced therapeutic potential, i.e. such compounds should improve the lipid profile, with a superior effect on HDL-C raising compared to current treatments and with additional positive effects on normalization of insulin-levels (Oliver et al; Proc Nat Acad Sci USA 2001; 98: 5306-11). Recent observations also suggest that there is a independent PPARα mediated effect on insulin-sensitization in addition to its well known role in reducing triglycerides (Guerre-Millo et al; J Biol Chem 2000; 275:16638-16642).

Thus, a need exists in the art for selective PPARδ agonists, or PPARδ agonists with additional PPARα activity, having superior therapeutic efficacy without the side-effects such as the weight gain seen with PPARγ agonists.

SUMMARY OF THE INVENTION

In one embodiment of the invention, provided is a compound of the formula I:

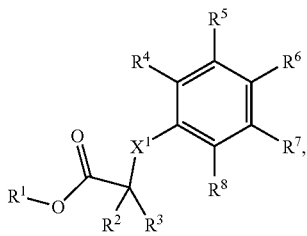

wherein
$X^1$ is O or S;
$R^1$ is hydrogen or $C_{1-7}$-alkyl;
$R^2$ is hydrogen or $C_{1-7}$-alkyl,
$R^3$ is hydrogen or $C_{1-7}$-alkyl;
$R^4$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;
$R^5$, $R^6$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;
and one of $R^5$, $R^6$ and $R^7$ is

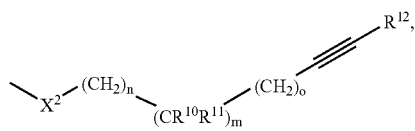

wherein
$X^2$ is selected from the group consisting of S, O, $NR^9$, $(CH_2)_pNR^9CO$ and $(CH_2)_pCONR^9$;
$R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl;
$R^{10}$ is selected from the group consisting of $C_{1-7}$-alkyl, $C_{3-7}$-cycloalkyl, fluoro-$C_{1-7}$-alkyl and $C_{1-7}$-alkoxy-$C_{1-7}$-alkyl;
$R^{11}$ is selected from the group consisting of hydrogen, $C_{1-7}$-alkyl, and $C_{1-7}$-alkoxy-$C_{1-7}$-alkyl;
or $R^{10}$ and $R^{11}$ together with the carbon atom they are attached to form a $C_{3-6}$-cycloalkyl ring;
m, o, p is 0, 1 or 2; n is 0, 1, 2 or 3;
and the sum of m, n and o is 1 to 5;
$R^{12}$ is aryl or heteroaryl;
and pharmaceutically acceptable salts and/or esters thereof.

In another embodiment of the present invention, provided is a pharmaceutical composition comprising a therapeutically effective amount of a compound of formula I, as well as a pharmaceutically acceptable carrier and/or adjuvant.

In a further embodiment of the present invention, provided is a method for the treatment and/or prevention of diseases which are modulated by PPARδ and/or PPARα agonists, comprising the step of administering a therapeutically effective amount of a compound of the formula I to a human being or animal in need thereof.

DETAILED DESCRIPTION

The novel compounds of the present invention exceed the compounds known in the art, inasmuch as they bind to and selectively activate PPARδ or coactivate PPARδ and PPARα simultaneously and very efficiently, and with much improved pharmacokinetic properties. Therefore, these compounds combine the anti-dyslipidemic and anti-glycemic effects of PPARδ and PPARα activation with no effect on PPARγ. Consequently, HDL cholesterol is increased, triglycerides lowered and plasma glucose and insulin are reduced. In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2D disease syndrome are addressed by PPARδ-selective agonists and PPARδ and α coagonists, they are expected to have an enhanced therapeutic potential compared to the compounds already known in the art.

The compounds of the present invention further exhibit improved pharmacological properties compared to known compounds.

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono- or multiply substituted with fluorine. Examples of fluoro-lower alkyl groups are e.g. —$CF_3$, —$CH_2CF_3$, —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Preferred are the lower-alkoxy groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower fluoro-alkyl, lower-alkoxy, lower fluoro-alkoxy, aryl and/or aryloxy. Preferred substituents are halogen, —$CF_3$, —$OCF_3$, lower-alkyl and/or lower-alkoxy. Preferred are the specifically exemplified aryl groups.

The term "heteroaryl" refers to an aromatic 5- or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl".

Preferred heteroaryl groups are e.g. pyridyl, thienyl and furyl which can optionally be substituted as described above, preferably with halogen, lower fluoro-alkyl such as —$CF_3$, lower fluoro-alkoxy such as —$OCF_3$, lower-alkyl and/or lower-alkoxy.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "pharmaceutically acceptable salts" embraces salts of the compounds of formula (I) with pharmaceutically acceptable bases such as alkali salts, e.g. Na— and K-salts, alkaline earth salts, e.g. Ca— and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

In detail, the present invention relates to compounds of formula (I)

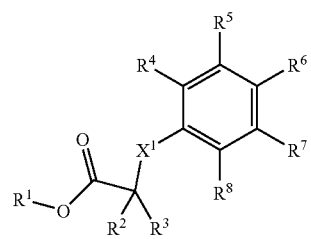

wherein
$X_1$ is O or S;
$R^1$ is hydrogen or $C_{1-7}$-alkyl;
$R^2$ is hydrogen or $C_{1-7}$-alkyl,
$R^3$ is hydrogen or $C_{1-7}$-alkyl;
$R^4$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;
$R^5$, $R^6$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;
and one of $R^5$, $R^6$ and $R^7$ is

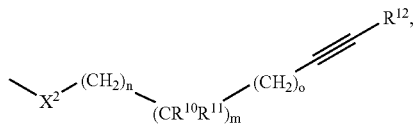

wherein
$X^2$ is selected from the group consisting of S, O, $NR^9$, $(CH_2)_PNR^9CO$ and $(CH_2)_PCONR^9$,
$R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl;
$R^{10}$ is selected from the group consisting of $C_{1-7}$-alkyl, $C_{3-7}$-cycloalkyl, fluoro-$C_{1-7}$-alkyl and $C_{1-7}$-alkoxy-$C_{1-7}$-alkyl;
$R^{11}$ is selected from the group consisting of hydrogen, $C_{1-7}$-alkyl, and $C_{1-7}$-alkoxy-$C_{1-7}$-alkyl;
or $R^{10}$ and $R^{11}$ together with the carbon atom they are attached to form a $C_{3-6}$-cycloalkyl ring;

m, o, p is 0, 1 or 2; n is 0, 1, 2 or 3;
and the sum of m, n and o is 1 to 5;
$R^{12}$ is aryl or heteroaryl;
and pharmaceutically acceptable salts and/or esters thereof.

Preferred compounds of formula I of the present invention are compounds of formula

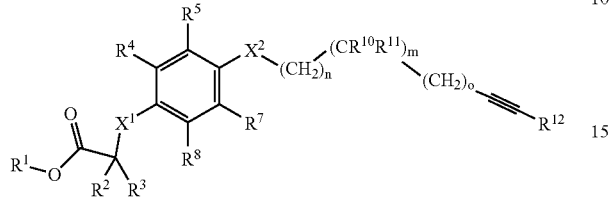

I-A wherein
$X^1$, $X^2$, $R^3$ to $R^4$, $R^8$, $R^{10}$ to $R^{12}$, m, n and o are as defined herein before;
$R^5$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and
pharmaceutically acceptable salts and/or esters thereof.

More preferred are those compounds of formula I-A in accordance with the present invention, wherein at least one of $R^4$, $R^5$, $R^7$ and $R^8$ is selected from the group consisting of $C_{1-7}$-alkyl, $C_{1-7}$-alkoxy and halogen, with those compounds of formula I-A wherein $R^4$ is $C_{1-7}$-alkyl, halogen or $C_{1-7}$-alkoxy being especially preferred. Even more preferred are those compounds of formula I-A, wherein one of $R^4$ and $R^8$ is methyl and the other one hydrogen.

Also preferred are compounds of formula I-A, wherein at least one of $R^4$, $R^5$, $R^7$ and $R^8$ is halogen, with those compounds of formula I-A wherein halogen means chloro, being especially preferred, and with those compounds of formula I-A, wherein $R^4$ and $R^7$ are chloro, being more preferred.

Also preferred are compounds of formula I having the formula

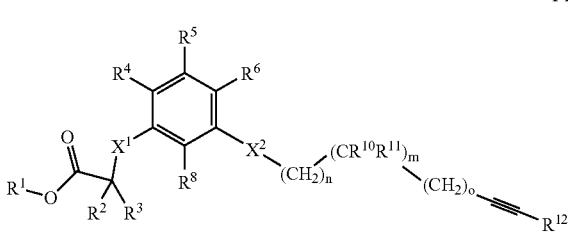

I-B wherein
$X^1$, $X^2$, $R^1$ to $R^4$, $R^8$, $R^{10}$ to $R^{12}$, n, m and o are as defined herein before;
$R^5$ and $R^6$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and
pharmaceutically acceptable salts and/or esters thereof.

More preferred are those compounds of formula I-B in accordance with the present invention, wherein at least one of $R^4$, $R^5$, $R^6$ and $R^8$ is selected from the group consisting of $C_{1-7}$-alkyl, halogen and $C_{1-7}$-alkoxy, with those compounds of formula I-B wherein $R^4$ is $C_{1-7}$-alkyl, halogen or $C_{1-7}$-alkoxy being especially preferred. Even more preferred are those compounds of formula I-B, wherein one of $R^4$ and $R^8$ is methyl and the other one is hydrogen.

Further preferred compounds of formula I have the formula

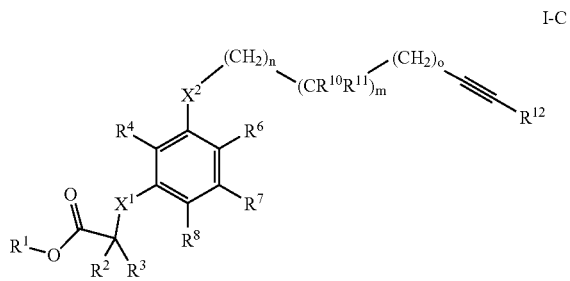

I-C wherein
$X^1$, $X^2$, $R^3$ to $R^4$, $R^8$, $R^{10}$ to $R^{12}$, m, n and o are as defined herein before;
$R^6$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano; and
pharmaceutically acceptable salts and/or esters thereof.

More preferred are those compounds of formula I-C in accordance with the present invention, wherein at least one of $R^4$, $R^6$, $R^7$ and $R^8$ is selected from the group consisting of $C_{1-7}$-alkyl, halogen and $C_{1-7}$-alkoxy, with those compounds of formula I-C wherein $R^4$ is $C_{1-7}$-alkyl or $C_{1-7}$-alkoxy being especially preferred. Even more preferred are those compounds of formula I-C, wherein one of $R^4$ and $R^8$ is methyl and the other one is hydrogen.

Preferred compounds of formula I are those, wherein $R^1$ is hydrogen. $X^1$ is selected from O or S. Compounds of formula I, wherein $X^1$ is O are preferred. More preferred are those compounds of formula I, wherein $X^1$ is O and at least one of $R^2$ and $R^3$ is $C_{1-7}$-alkyl with those compounds of formula I wherein $X^1$ is O and $R^2$ and $R^3$ are $C_{1-7}$-alkyl being especially preferred.

Thus, compounds, wherein $R^2$ and $R^3$ are $C_{1-7}$-alkyl, are preferred, with those compounds wherein $R^2$ and $R^3$ are methyl being especially preferred.

Also preferred are compounds of formula I, wherein $R^2$ and $R^3$ are hydrogen.

$X^2$ is selected from the group consisting of S, O, $NR^9$, $(CH_2)_pNR^9CO$ and $(CH_2)_pCONR^9$, wherein $R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl.

Preferred are compounds of formula I, wherein $X^2$ is selected from the group consisting of S, O and $NR^9$ and $R^9$ is hydrogen, $C_{1-7}$-alkyl, $C_{3-7}$-cycloalkyl, fluoro-$C_{1-7}$-alkyl, hydroxy-$C_{2-7}$-alkyl, or $C_{1-7}$-alkoxy-$C_{2-7}$-alkyl, with compounds of formula I wherein $X^2$ is S or O, being particularly preferred.

One group of especially preferred compounds of formula I are those, wherein $X^2$ is S.

Another especially preferred group of compounds are those, wherein $X^2$ is O.

Another group of compounds of formula I are those, wherein $X^2$ is $(CH_2)_pNR^9CO$ or $(CH_2)_pCONR^9$, $R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl and the integer p is 0, 1 or 2. Preferably, $R^9$ is hydrogen or $C_{1-7}$-alkyl. Preferred p is 1.

$R^{10}$ is selected from the group consisting of $C_{1-7}$-alkyl, $C_{3-7}$-cycloalkyl, fluoro-$C_{1-7}$-alkyl and $C_{1-7}$-alkoxy-$C_{1-7}$-alkyl and $R^{11}$ is selected from the group consisting of hydrogen, $C_{1-7}$-alkyl and $C_{1-7}$-alkoxy-$C_{1-7}$-alkyl; or $R^{10}$ and $R^{11}$ together with the carbon atom they are attached to form a $C_{3-6}$-cycloalkyl ring. Preferred are compounds of formula I, wherein $R^{10}$ is selected from the group consisting of $C_{1-7}$-alkyl, $C_{3-7}$-cycloalkyl, fluoro-$C_{1-7}$-alkyl and $C_{1-7}$-alkoxy-$C_{1-7}$-alkyl and $R^{11}$ is hydrogen or $C_{1-7}$-alkyl.

The integer m is 0, 1 or 2. Preferred are compounds of formula I wherein m is 0.

The integer n is 0, 1, 2 or 3 and the integer o is 0, 1 or 2. Especially preferred are compounds of formula I, wherein $X^2$ is S or O, m is 0 and the sum of n and o is 1, 2 or 3.

Furthermore, compounds of formula I, wherein $R^{12}$ is aryl, are preferred. More preferred are those compounds of formula I, wherein $R^{12}$ is unsubstituted phenyl or phenyl substituted with one to three groups selected from the group consisting of $C_{1-7}$-alkyl, $C_{1-7}$-alkoxy, halogen, fluoro-$C_{1-7}$-alkyl, fluoro-$C_{1-7}$-alkoxy and cyano, with those compounds, wherein $R^{12}$ is phenyl substituted with halogen, $C_{1-7}$-alkoxy, fluoro-$C_{1-7}$-alkyl or fluoro-$C_{1-7}$-alkoxy, being particularly preferred. Especially preferred are those compounds, wherein $R^{12}$ is phenyl substituted with trifluoromethoxy.

Another group of preferred compounds of formula I are those wherein $R^{12}$ is heteroaryl. Especially preferred are those compounds of formula I, wherein $R^{12}$ is unsubstituted pyridyl or pyridyl substituted with one to three groups selected from the group consisting of $C_{1-7}$-alkyl, $C_{1-7}$-alkoxy, halogen, fluoro-$C_{1-7}$-alkyl, fluoro-$C_{17}$-alkoxy and cyano, with those compounds, wherein $R^{12}$ is pyridyl substituted by fluoro-$C_{1-7}$-alkyl or fluoro-$C_{1-7}$-alkoxy, being particularly preferred.

Examples of preferred compounds of formula I are the following:

2-methyl-2-{2-methyl-4-[5-(4-trifluoromethoxy-phenyl)-pent-4-ynylsulfanyl]-phenoxy}-propionic acid,
2-methyl-2-{2-methyl-4-[4-(4-trifluoromethyl-phenyl)-but-3-ynylsulfanyl]-phenoxy}-propionic acid,
2-methyl-2-{2-methyl-4-[5-(3-trifluoromethoxy-phenyl)-pent-4-ynylsulfanyl]-phenoxy}-propionic acid,
{2-methyl-4-[5-(4-trifluoromethoxy-phenyl)-pent-4-ynylsulfanyl]-phenoxy}-acetic acid,
{2-methyl-4-[3-(4-trifluoromethyl-phenyl)-prop-2-ynylsulfanyl]-phenoxy}-acetic acid,
{2-methyl-4-[3-(3-trifluoromethyl-phenyl)-prop-2-ynylsulfanyl]-phenoxy}-acetic acid,
{2-methyl-4-[3-(2-trifluoromethyl-phenyl)-prop-2-ynylsulfanyl]-phenoxy}-acetic acid,
{4-[3-(4-chloro-phenyl)-prop-2-ynylsulfanyl]-2-methyl-phenoxy}-acetic acid,
{4-[3-(4-methoxy-phenyl)-prop-2-ynylsulfanyl]-2-methyl-phenoxy}-acetic acid,
[2-methyl-4-(3-phenyl-prop-2-ynylsulfanyl)-phenoxy]-acetic acid,
{4-[3-(4-fluoro-phenyl)-prop-2-ynylsulfanyl]-2-methyl-phenoxy}-acetic acid,
{2-methyl-4-[4-(4-trifluoromethyl-phenyl)-but-3-ynylsulfanyl]-phenoxy}-acetic acid,
2-methyl-2-{2-methyl-4-[5-(4-trifluoromethoxy-phenyl)-pent-4-ynyloxy]-phenoxy}-propionic acid,
2-methyl-2-{2-methyl-4-[5-(4-trifluoromethyl-phenyl)-pent-4-ynyloxy]-phenoxy}-propionic acid,
2-{4-[5-(4-chloro-phenyl)-pent-4-ynyloxy]-2-methyl-phenoxy}-2-methyl-propionic acid,
2-methyl-2-{2-methyl-4-[4-(4-trifluoromethyl-phenyl)-but-3-ynyloxy]-phenoxy}-propionic acid,
2-methyl-2-{2-methyl-4-[4-(4-trifluoromethoxy-phenyl)-but-3-ynyloxy]-phenoxy}-propionic acid,
2-{4-[4-(4-chloro-phenyl)-but-3-ynyloxy]-2-methyl-phenoxy}-2-methyl-propionic acid,
2-methyl-2-{2-methyl-4-[5-(5-trifluoromethyl-pyridin-2-yl)-pent-4-ynyloxy]-phenoxy}-propionic acid,
{2-methyl-4-[5-(4-trifluoromethoxy-phenyl)-pent-4-ynyloxy]-phenoxy}-acetic acid,
2-{2,5-dichloro-4-[5-(4-trifluoromethoxy-phenyl)-pent-4-ynyloxy]-phenoxy}-2-methyl-propionic acid,
2-methyl-2-{2-methyl-4-[5-(3-trifluoromethoxy-phenyl)-pent-4-ynyloxy]-phenoxy}-propionic acid,
2-methyl-2-{2-methyl-4-[5-(3-trifluoromethyl-phenyl)-pent-4-ynyloxy]-phenoxy}-propionic acid,
2-{4-[2,2-dimethyl-5-(4-trifluoromethoxy-phenyl)-pent-4-ynyloxy]-2-methyl-phenoxy}-2-methyl-propionic acid,
2-{4-[2,2-dimethyl-5-(4-trifluoromethoxy-phenyl)-pent-4-ynylsulfanyl]-2-methyl-phenoxy}-2-methyl-propionic acid,
2-{4-[5-(3-fluoro-phenyl)-pent-4-ynyloxy]-2-methyl-phenoxy}-2-methyl-propionic acid,
2-{4-[5-(4-chloro-3-fluoro-phenyl)-pent-4-ynyloxy]-2-methyl-phenoxy}-2-methyl-propionic acid,
2-methyl-2-{2-methyl-4-[5-(2-trifluoromethyl-pyrimidin-5-yl)-pent-4-ynyloxy]-phenoxy}-propionic acid,
2-methyl-2-(4-{[5-(4-trifluoromethoxy-phenyl)-pent-4-ynoylamino]-methyl}-phenoxy)-propionic acid,
2-methyl-2-[4-({methyl-[5-(4-trifluoromethoxy-phenyl)-pent-4-ynoyl]-amino}-methyl)-phenoxy]-propionic acid,
rac-2-methyl-2-{2-methyl-4-[1-methyl-5-(4-trifluoromethoxy-phenyl)-pent-4-ynyloxy]-phenoxy}-propionic acid,
2-{3-fluoro-4-[5-(4-trifluoromethoxy-phenyl)-pent-4-ynyloxy]-phenoxy}-2-methyl-propionic acid,
2-{3-fluoro-2-methyl-4-[5-(4-trifluoromethoxy-phenyl)-pent-4-ynyloxy]-phenoxy}-2-methyl-propionic acid,
2-methyl-2-(2-methyl-4-{1-[3-(4-trifluoromethoxy-phenyl)-prop-2-ynyl]-cyclobutylmethoxy}-phenoxy)-propionic acid,
2-methyl-2-(2-methyl-4-{1-[3-(4-trifluoromethoxy-phenyl)-prop-2-ynyl]-cyclopropylmethoxy}-phenoxy)-propionic acid,
2-{5-methoxy-2-methyl-4-[5-(4-trifluoromethoxy-phenyl)-pent-4-ynyloxy]-phenoxy}-2-methyl-propionic acid, and pharmaceutically acceptable salts and/or esters thereof.

Especially preferred are also the following compounds of formula I of the present invention:
{2-methyl-4-[5-(4-trifluoromethoxy-phenyl)-pent-4-ynylsulfanyl]-phenoxy}-acetic acid,
2-methyl-2-{2-methyl-4-[5-(4-trifluoromethoxy-phenyl)-pent-4-ynyloxy)-phenoxy}-propionic acid,
2-methyl-2-{2-methyl-4-[4-(4-trifluoromethoxy-phenyl)-but-3-ynyloxy)-phenoxy}-propionic acid,
2-{2,5-dichloro-4-[5-(4-trifluoromethoxy-phenyl)-pent-4-ynyloxy]-phenoxy}-2-methyl-propionic acid,
2-{4-[2,2-dimethyl-5-(4-trifluoromethoxy-phenyl)-pent-4-ynylsulfanyl]-2-methyl-phenoxy}-2-methyl-propionic acid,
2-methyl-2-(2-methyl-4-{1-[3-(4-trifluoromethoxy-phenyl)-prop-2-ynyl]-cyclobutylmethoxy}-phenoxy)-propionic acid,
and pharmaceutically acceptable salts and/or esters thereof.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral absorbens or eluant). The invention embraces all of these forms.

Compounds of formula I may also contain $C_{1-7}$-alkenyl groups. All forms of cis- and trans-isomers are embraced by the present invention.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of formula

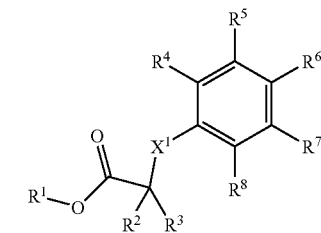

II wherein $R^1$ is $C_{1-7}$-alkyl, $X^1$ and $R^2$ to $R^8$ are as defined herein before and one of $R^5$, $R^6$ or $R^7$ is selected from —OH, —SH or —NHR$^9$, wherein $R^9$ is as defined herein before, with a compound of formula

III $R^{13}$—(CH$_2$)$_n$—(CR$^{10}$R$^{11}$)$_m$—(CH$_2$)$_o$—≡—R$^{12}$ wherein $R^{10}$, $R^{11}$, $R^{12}$, m, n and o are as defined herein before and $R^{13}$ is —OH, —Cl, —Br, —I or another leaving group, to obtain a compound of formula

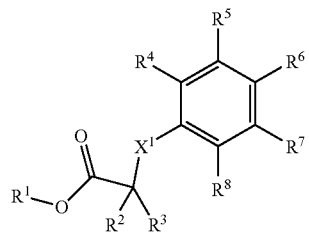

I-1 wherein one of $R^5$, $R^6$ and $R^7$ is

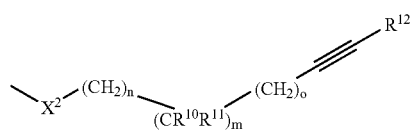

and wherein $X^2$ is O, S or —NR$^9$, $R^1$ is $C_{1-7}$-alkyl and $X^1$, $R^2$ to $R^{12}$ and m, n and o are as defined herein before, and optionally hydrolyzing the ester group to obtain a compound of formula I, wherein $R^1$ is hydrogen;

or, alternatively, reacting a compound of formula

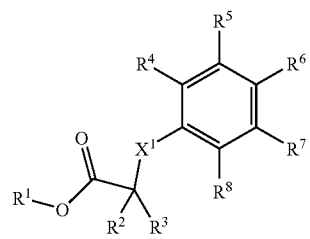

IV wherein $R^1$ is $C_{1-7}$-alkyl, $R^2$ to $R^8$ are as defined as herein before and one of $R^5$, $R^6$ or $R^7$ is —(CH$_2$)$_p$—NHR$^9$, wherein $R^9$ and p are as defined in claim 1, with a compound of formula

V

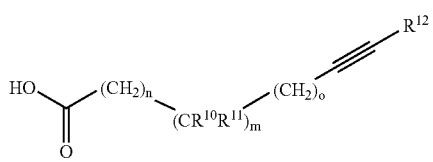

wherein $R^{10}$, $R^{11}$, $R^{12}$, m, n and o are as defined herein before, to obtain a compound of formula

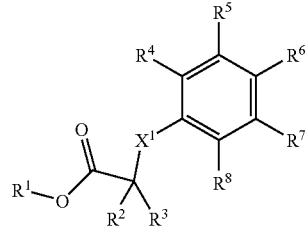

I-2 wherein one of $R^5$, $R^6$ and $R^7$ is

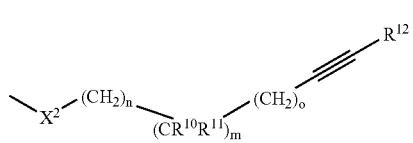

and wherein $X^2$ is —$(CH_2)_p$—$NR^9CO$—, $R^1$ is $C_{1-7}$-alkyl and $X^1$, $R^2$ to $R^{12}$ and m, n, o and p are as defined herein before, and optionally hydrolyzing the ester group to obtain a compound of formula I, wherein $R^1$ is hydrogen;

or, alternatively, reacting a compound of formula

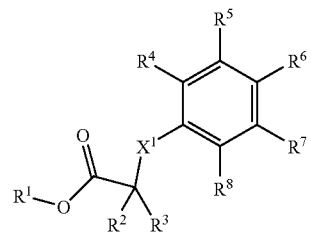

VI wherein $R^1$ is $C_{1-7}$-alkyl, $R^2$ to $R^8$ are as defined herein before and one of $R^5$, $R^6$ or $R^7$ is —$(CH_2)_p$—COOH, and p is defined as herein before, with a compound of formula

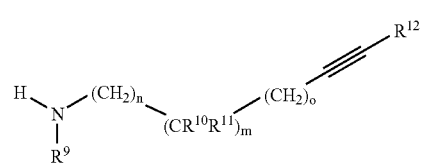

VII wherein $R^9$, $R^{10}$, $R^{11}$, $R^{12}$, m, n and o are as defined herein before, to obtain a compound of formula

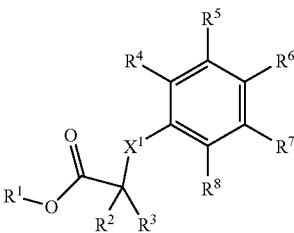

I-3 wherein one of $R^5$, $R^6$ and $R^7$ is and wherein $X^2$ is —$(CH_2)_p$—$CONR^9$, $R^1$ is $C_{1-7}$-alkyl and $X^1$, $R^2$ to $R^{12}$ and m, n, o and p are as defined herein below;

and optionally hydrolyzing the ester group to obtain a compound of formula I, wherein $R^1$ is hydrogen.

As described above, the compounds of formula (I) of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment of low HDL cholesterol levels, high LDL cholesterol levels, high triglyceride levels, and the metabolic syndrome (syndrome X) is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

The synthesis of compounds with the general structure I, particularly compounds according to formula Ia to Ik, are described in scheme 1 to scheme 5. Scheme 6 to scheme 8 describe the synthesis of alkyne building blocks 5 and 6 (scheme 1), identical to 11 and 12 (scheme 3), 6 and 7 (scheme 5) and acids 5 and amines 6 (scheme 4).

The synthesis of compounds with the general structure I of the present invention, particularly compounds according to formula Ia with $X^1$ and $X^2$ equal to oxygen can be accomplished according to scheme 1.

Hydroxy aldehydes or hydroxy aryl alkyl ketones 1 are known or can be prepared by methods known in the art, e. g. by applying the following reaction sequence to a phenol 1 where optionally one of $R^4$, $R^5$, $R^7$ or $R^8$ is a fluoro atom: i) protection of the phenolic hydroxy group as a methoxy group; ii) protection of the carbonyl group as an acetal or ketal; iii) deprotonation and alkylation to introduce an additional substituent $R^4$, $R^5$, $R^7$ or $R^8$; iv) global or sequential deprotection. Reaction of phenols 1 with alpha halo esters of formula 2 in the presence of a base like potassium or cesium carbonate in solvents like acetone, methyl-ethyl ketone, acetonitrile or N,N-dimethylformamide in a temperature range between room temperature and 140° C. leads to the corresponding ether compounds 3 (step a). Baeyer Villiger oxidation, e. g. with meta-chloroperbenzoic acid in a solvent like dichloromethane, and subsequent ester cleavage leads to compounds 4 (step b). Alkynes 5 (prepared as outlined in schemes 6 to 8) are condensed with phenols 4 according to well known procedures (step c): if $R^{13}$ represents a hydroxy group e. g. via Mitsunobu-reaction, with triphenylphosphine and di-tert-butyl-, diisopropyl- or diethyl-azodicarboxylate as reagents; this transformation is preferably carried out in a solvent like toluene, dichloromethane or tetrahydrofuran at ambient temperature.

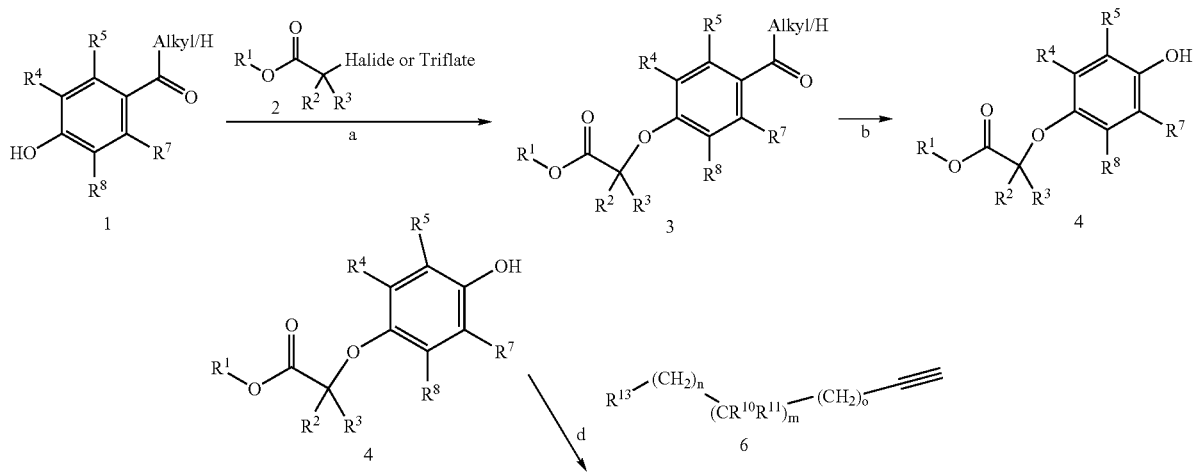

Scheme 1

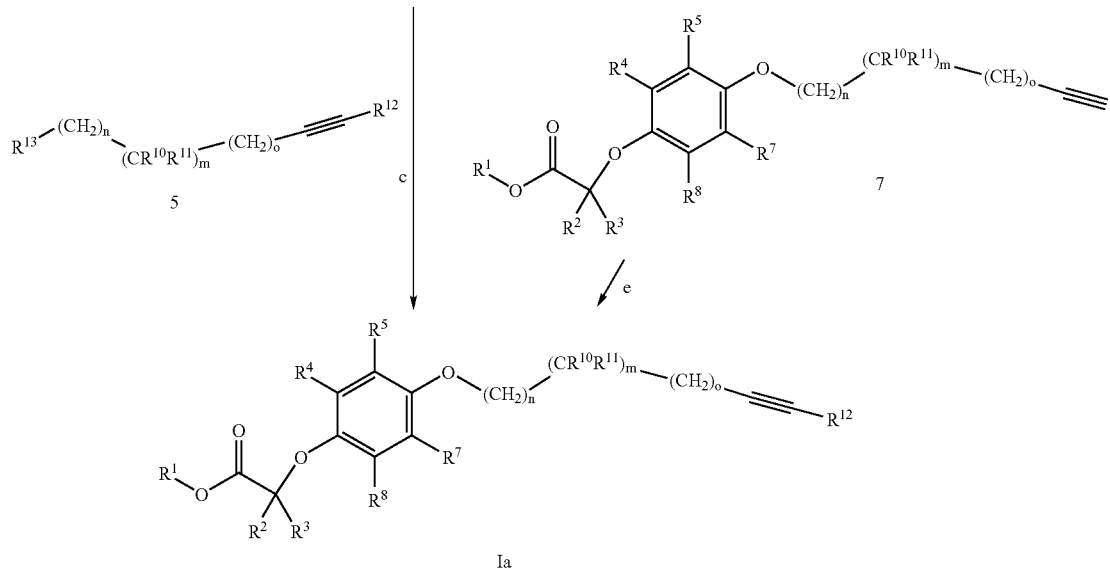

Ia

Alternatively, if $R^{13}$ represents a halide, mesylate, tosylate or triflate moiety, the alkyne 5 can be reacted with phenols 4 in solvents like N,N-dimethylformamide, dimethylsulfoxide, acetonitrile, acetone or methyl-ethyl ketone in the presence of a weak base like cesium or potassium carbonate at a temperature ranging from room temperature to 140° C., preferably around 50° C. to yield ether compounds Ia (step c). $R^{12}$ can also represent a protecting group, e. g. a trimethylsilyl group. Removal of the protecting group, e. g. by using n-Bu$_4$NF forms the free acetylene which can be modified via a Sonogashira-reaction as described below to give new ether compounds Ia. This transformation can be performed either on esters Ia ($R^{12}$=H, $R^1$=alkyl) or on acids Ia ($R^{12}$=H, $R^1$=H). Alternatively, phenols 4 can be reacted with alkyne 6 (prepared as outlined in schemes 6 to 8) to give alkynes 7 (step d). Alkynes 5 or 6 with $R^{13}$=OH can also be transformed in situ to the corresponding triflates by treatment with trifluoromethanesulfonic anhydride/2,6-di-tert-butylpyridine in dichloromethane at 0° C. to room temperature. The triflates are then reacted with phenols 4 in solvents like N,N-dimethylformamide, dimethylsulfoxide, acetonitrile, acetone or methyl-ethyl ketone in the presence of a weak base like cesium or potassium carbonate at a temperature ranging from room temperature to 140° C., preferably around 50° C. to yield ether compounds Ia (step c) or 7 (step d), respectively. Intermediates 7 can further be subjected to Sonogashira coupling conditions (e.g. see descriptions in schemes 6 and 7 or Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071) to give the final compounds Ia (step e). Esters of formula Ia can optionally be hydrolyzed according to standard procedures, e. g. by treatment with an alkali hydroxide like LiOH or NaOH in a polar solvent mixture like tetrahydrofuran/ethanol/water leading to carboxylic acids Ia.

An analogous reaction scheme with the same reaction sequences applies for the isomeric compound series leading to compounds of general formula I, particularly compounds according to formula Ib:

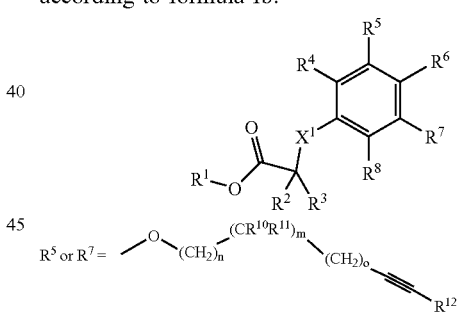

Ib

The synthesis of compounds with the general structure I, particularly compounds according to formula Ic, with $X^1$ equal to O and $X^2$ equal to nitrogen, can be accomplished according to schemes 2 and 3.

Scheme 2

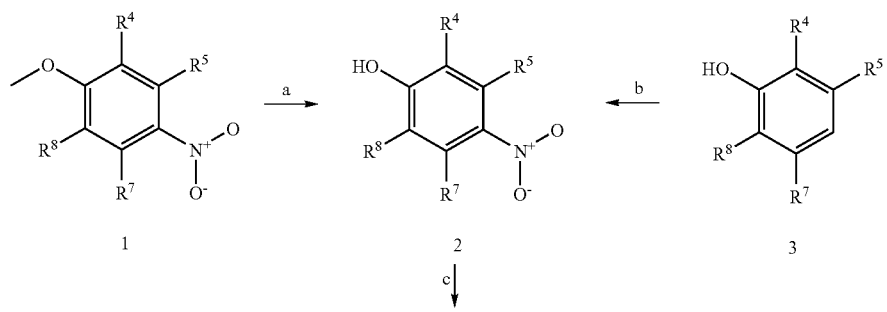

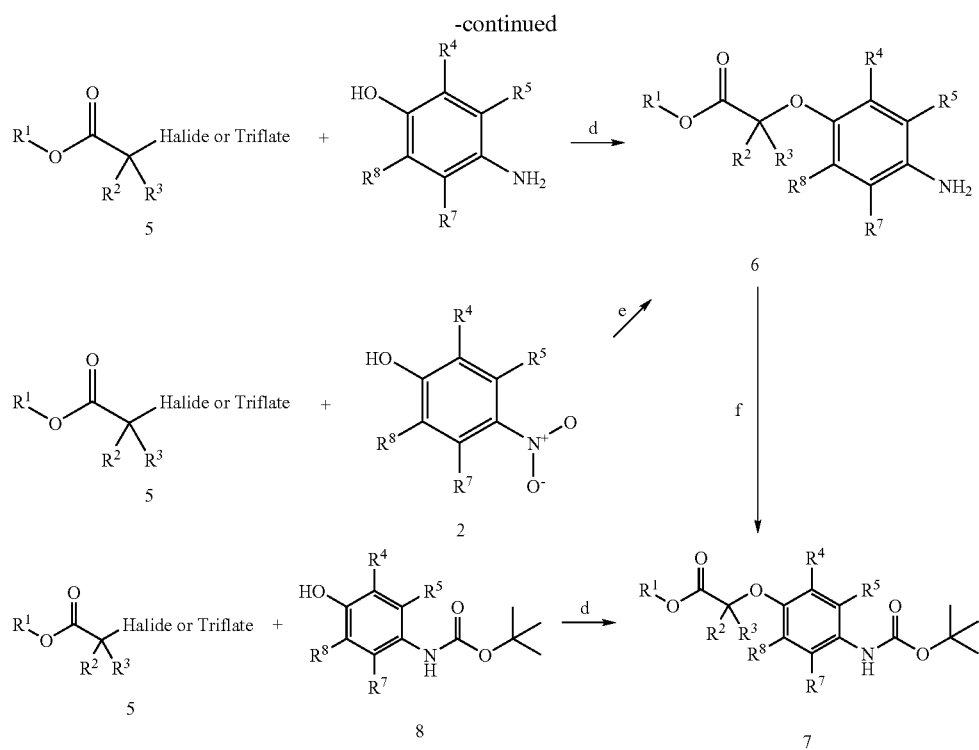

Nitro-phenols 2 of scheme 2 are commercially available, known or can be synthesized from anisols 1 by demethylation with aqueous 62% HBr in acetic acid between room temperature and 120° C. (step a). Alternatively, phenols 3 can be nitrated in para-position according to well established methods, e. g. with a solution of NaNO₃ in water/concentrated hydrochloric acid in a solvent like Et₂O, followed by the addition of acetic acid anhydride at room temperature [following a procedure of P. Keller, *Bull. Soc. Fr.* 1994, 131, 27-29] leading to phenols 2 (step b). Nitro-phenols 2 are then hydrogenated in an alcohol like EtOH or MeOH in the presence of Pd/C and optionally an acid like HCl or AcOH at room temperature to give anilines 4 (step c). Intermediates 4 are then O-alkylated with compounds 5, e.g. a bromoacetate 5, in the presence of K₂CO₃ or Cs₂CO₃ in a solvent like acetonitrile or acetone between 10° C. and 60° C., preferable at room temperature to give intermediates 6 of scheme 2 (step d). Activated esters 5 are commercially available or can be synthesized by methods known in the art. Triflates 5 can be prepared from the corresponding alcohols. Anilines 6 can alternatively be synthesized from compounds 5 and nitrophenols 2 in a two step procedure: first by O-alkylation as described above, followed by hydrogenation using catalytic amounts of Pd/C in an alcohol like MeOH or EtOH optionally in the presence of AcOH or HCl (step e). BOC-protection with di-tert-butyl dicarbonate in tetrahydrofuran at a temperature between room temperature and the reflux temperature of the solvent yields compounds 7 (step f). Compounds 7 can also be synthesized directly from compounds 5 and BOC-protected anilines 8 (which are e. g. accessible via treatment of anilines 4 with di-tert-butyl dicarbonate under standard conditions) with K₂CO₃ or Cs₂CO₃ as described for the synthesis of compounds 6 (step g).

Intermediates 7 of scheme 3 (equal to compounds 7 of scheme 2) can optionally be alkylated at nitrogen using sodium hydride and a reactive $R^9$-halogenide/mesylate or triflate to give compounds 9 (step h, scheme 3). Standard BOC-deprotection (TFA/CH₂Cl₂, or HCl in dioxane) at 0° C. to room temperature affords anilines 10 (step i, scheme 3). Reaction with activated alkyne 11 ($R^{13}$ being a halide, a methanesulfonate or a triflate) using sodium hydride or sodium, potassium or cesium carbonate in N,N-dimethylformamide, dimethylsulfoxide, dimethylacetamide or tetrahydrofuran, at 0° C. to room temperature, leads to compounds Ic (step k). $R^{12}$ can also represent a protecting group, e. g. a trimethylsilyl group. Removal of the protecting group, e. g. by using n-Bu₄NF forms the free acetylene which can be modified via a Sonogashira reaction as described below to give new ether compounds Ic. This transformation can be performed either on esters Ic ($R^{12}$=H, $R^1$=alkyl) or on acids Ic ($R^{12}$=H, $R^1$=H). Secondary aniline compounds Ic ($R^9$=H) can be reductively methylated with an aqueous solution of NaH₂PO₃ and formaldehyde between room temperature and 65° C. [Loibner, H., Pruckner, A., Stuetz, A., *Tetrahedron Lett.* 1984, 25, 2535-2536] to give compounds Ic with $R^9$=Me. Alternatively, anilines 10 can be reacted with alkynes 12 (prepared as outlined in schemes 6 to 8) (step l) to give alkynes 13. Intermediates 13 can further be subjected to Sonogashira coupling conditions (e.g. see descriptions in schemes 6 and 7 or Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071) to give the final compounds Ic (step m). Ensuing hydrolysis with aqueous LiOH, NaOH or KOH in tetrahydrofuran/EtOH or another suitable solvent produces compounds Ic of scheme 3 in the form of the free acid.

Scheme 3

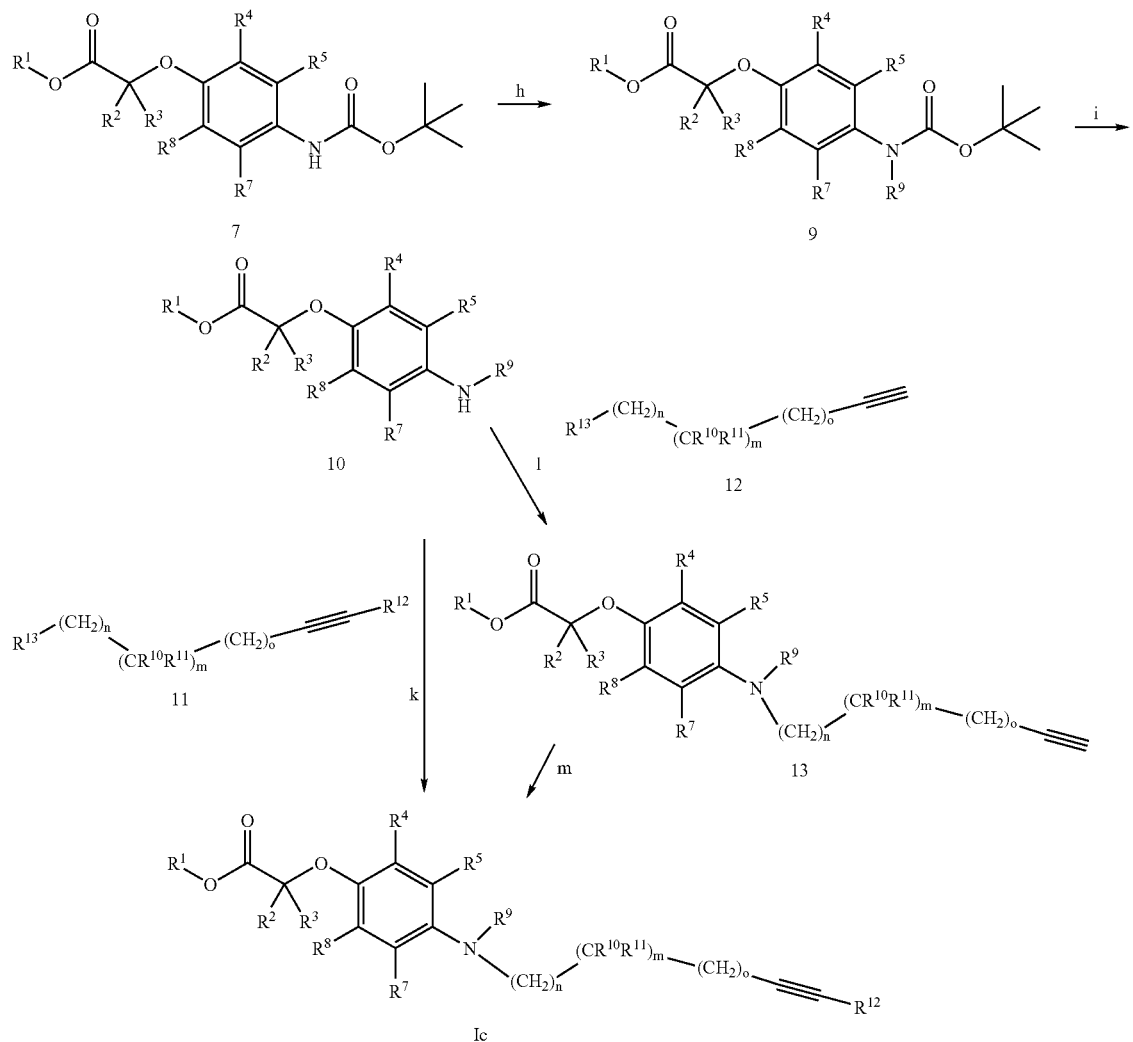

An analogous reaction scheme with the same reaction sequences applies for the isomeric compound series leading to compounds of general formula I, particularly compounds according to formula Id:

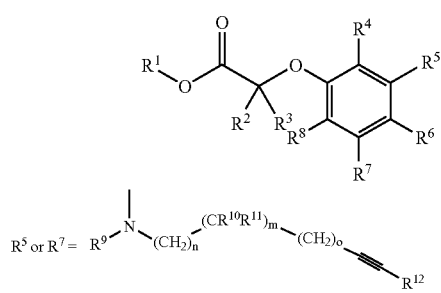

As alternative to the sequences described in scheme 2, the nitrogen containing intermediates can be prepared from suitable intermediates carrying a phenolic hydroxyl moiety. In such intermediates, optionally carrying one or more protective functions, the phenolic OH group can be replaced by the corresponding aromatic $NH_2$ function by methods known in the art. For example by a three step sequence as described in Tetrahedron Letters 43(42), 7617-7619(2002): i) transformation of the phenol moiety into its trifluoromethanesulfonate (triflic anhydride, 2,6-lutidine, 4-dimethylaminopyridine, dichloromethane, 0° C. to room temperature; ii) treatment of the triflate with benzophenone imine, di-palladium-tris(dibenzylideneacetone) complex, S-(−)-2,2′-bis(diphenylphosphino)-1,1′-binaphthyl, cesium carbonate, toluene, in a Schlenk tube at temperatures around 120° C.; iii) treatment with catalytic amounts of hydrochloric acid in wet tetrahydrofuran preferably at room temperature to liberate the aromatic $NH_2$ moiety.

The synthesis of compounds with the general structure I, particularly compounds according to formula Ie and If, with $X^1$ equal to O and $X^2$ equal to $(CH_2)_p NR^9 CO$, or $(CH_2)_p CONR^9$ can be accomplished according to scheme 4.

Nitriles 1 and aldehydes 2 can be prepared from the corresponding cyano- or formyl-phenols (which are known, commercially available or can be prepared by methods known in the art) by reaction with activated esters (compounds 5 in scheme 2) in the presence of a base like potassium or cesium carbonate in solvents like acetone, methyl-ethyl ketone, acetonitrile or N,N-dimethylformamide in a temperature range between room temperature and 140° C. Hydrogenation of nitrile compounds 1, e. g. with palladium on charcoal in a mixture of acetic acid and ethanol, leads to compounds 3 with p=1 (step a). The preparation of compounds 3 with p=0 has been described in scheme 2 and 3 (compounds 6, scheme 2, and compounds 10, scheme 3).

Compounds 3 with p=2 can be prepared from compounds 2 in a two step procedure: i) treatment with nitro-methane and ammonium acetate in acetic acid at a temperature around 110° C. to form the corresponding nitro styrene compounds; ii) hydrogenation with palladium on charcoal in the presence of a strong acid like sulfuric acid or hydrogen chloride in solvents like ethanol or acetic acid and in a temperature range between room temperature and 100° C. (step c). In order to introduce substituent $R^9$, BOC-protection of compounds 3, followed by alkylation and subsequent removal of the BOC group can be performed similarly as described in schemes 2 and 3. Compounds 4 with p=0 can be prepared by oxidizing aldehydes 2 under standard conditions to aromatic acids 4 (e. g. with sodium chlorite, sodium dihydrogen-phosphate in a mixture of tert butanol and water and in the presence of 3-methyl-2-butene at temperatures around room temperature) (step b).

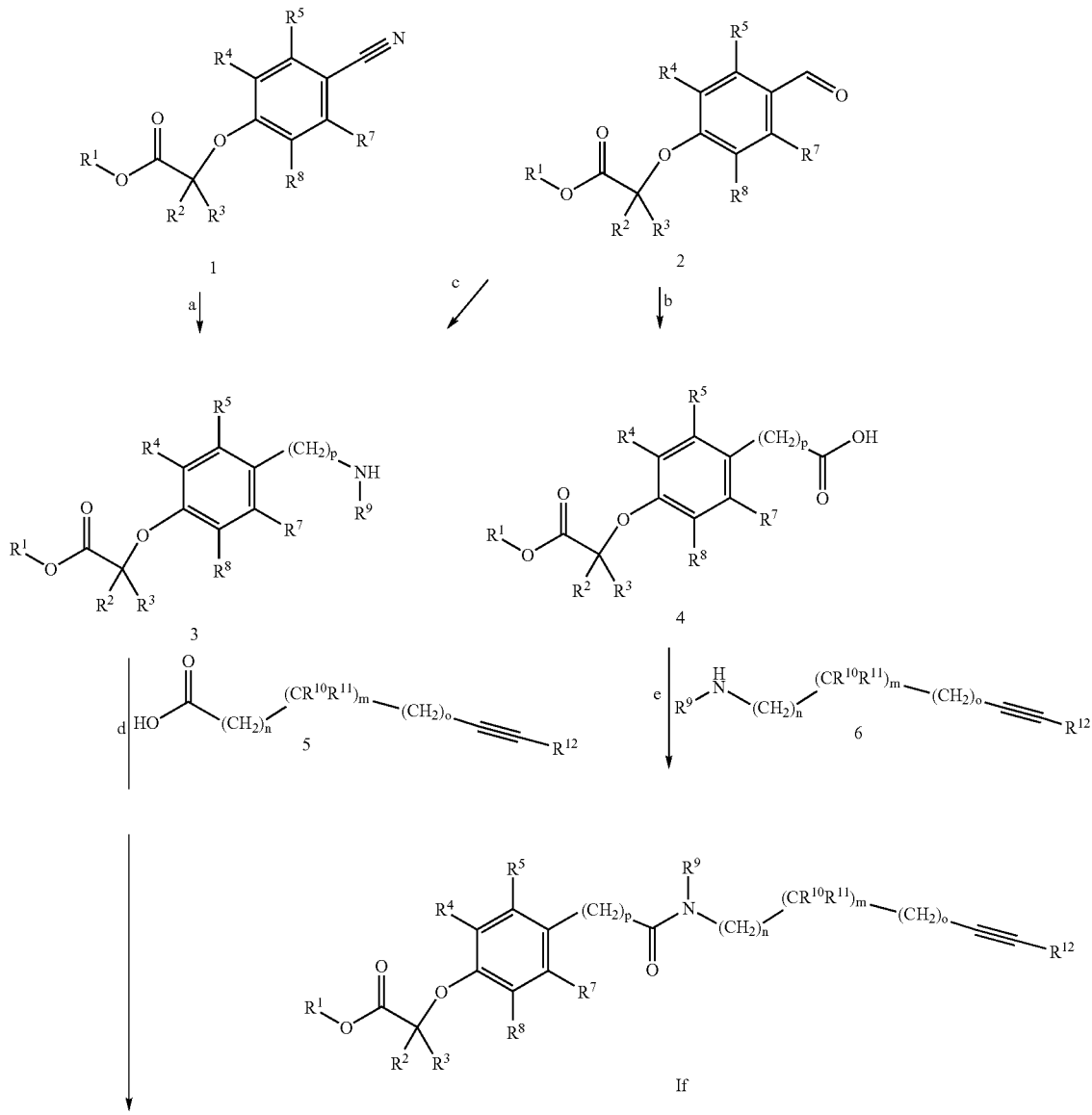

Scheme 4

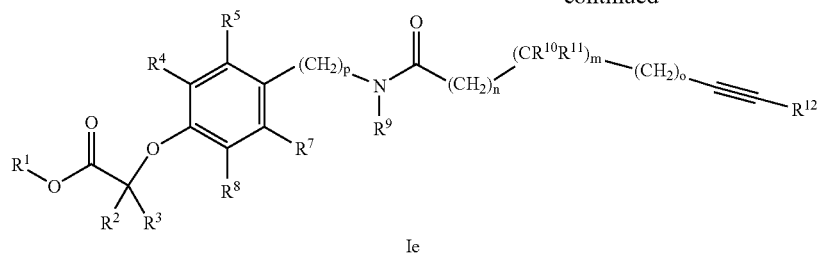

Ie

Compounds 4 with p=1 can be prepared from compounds 2 by a Wittig reaction using (methoxymethyl)-triphenylphosphonium chloride as reagent, treatment of the Wittig product with acid and oxidation of the aldehyde formed to the corresponding acid (step b). Compounds 4 with p=2 can be prepared from compounds 2 by a Horner-Emmons reaction with e. g. dimethyl(benzyloxy-carbonyl)methyl phosphonate, followed by concomitant reduction of the double bond and liberation of the ester function by e. g. hydrogenation with palladium on charcoal (step b). Condensation of amines 3 or acids 4 with acids 5 or amines 6 can be performed using well known procedures for amid formation, such as the use of N-(3-dimethylaminopropyl)-N′-ethyl-carbodiimide-hydrochloride and 4-dimethylamino-pyridine in dichloromethane at temperatures between 0° C. and room temperature yielding compounds Ie (step d) or If (step e). $R^{12}$ can also represent a protecting group, e. g. a trimethylsilyl group. Removal of the protecting group, e. g. by using n-BU$_4$NF forms the free acetylene which can be modified via a Sonogashira reaction as described below to give new ether compounds Ie or If. This transformation can be performed either on esters Ie or If ($R^{12}$=H, $R^1$=alkyl) or on acids Ie or If ($R^{12}$=H, $R^1$=H). Alternatively, amines 3 or acids 4 can be condensed with alkynes 5 or 6 with $R^{12}$=H (prepared as outlined in schemes 6 to 8) to give alkynes Ie ($R^{12}$=H) (step d) or If ($R^{12}$=H) (step e). Intermediates Ie ($R^{12}$=H) or If ($R^{12}$=H) can further be processed via Sonogashira coupling as described in schemes 6 and 7 to the final compounds Ie or If [e.g. see description in schemes 6 and 7 or Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071]. Esters of formula Ie or If can optionally be hydrolyzed according to standard procedures, e. g. by treatment with an alkali hydroxide like LiOH or NaOH in a polar solvent mixture like tetrahydrofuran/ethanol/water, giving carboxylic acids Ie or If.

An analogous reaction scheme with the same reaction sequences applies for the isomeric compound series leading to compounds of general formula I, particularly compounds according to formula Ig and Ih:

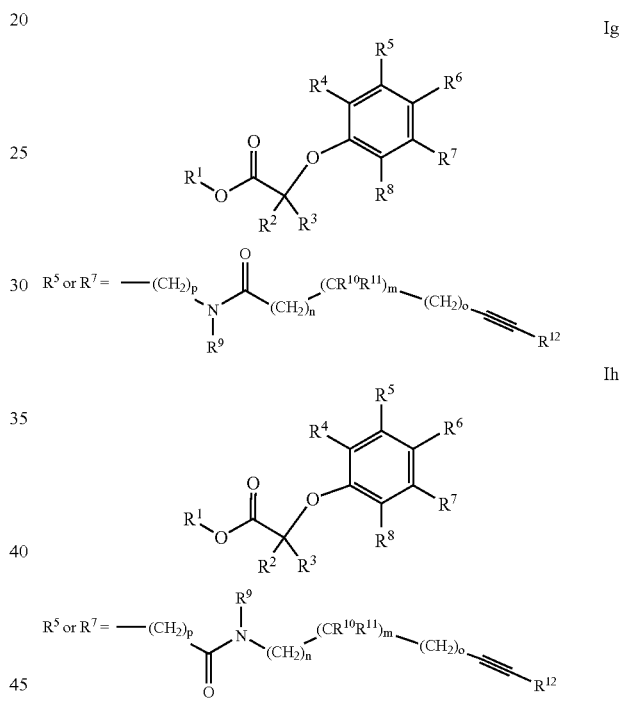

The synthesis of compounds with the general structure I, particularly compounds according to formula Ii (Scheme 5), with $X^1$ and/or $X^2$ equal to S can be accomplished in close analogy to the synthesis of the corresponding analogues with $X^1$ and/or $X^2$ equal to oxygen (Scheme 1).

Scheme 5

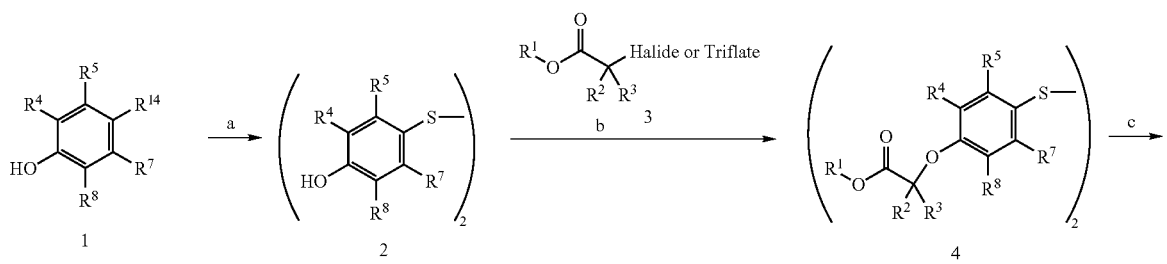

-continued

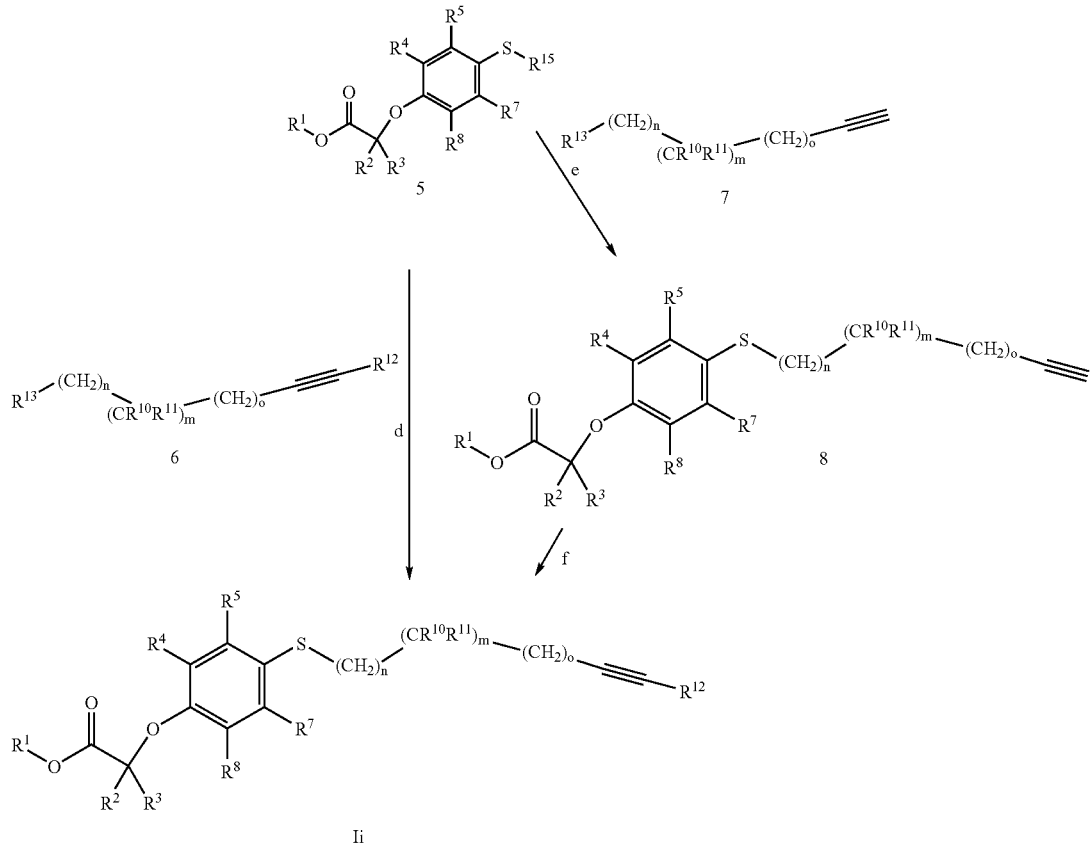

Suitable sulfur containing intermediates 1 ($R^{14}$=SH or SCN) are known, can be prepared by methods known in the art or are prepared from phenolic intermediates as described by W Zhi-Liang and A P Kozikowski (Journal of Organic Chemistry (2003), 68(23), 9116-9118): treatment of a phenolic intermediate with sodium thiocyanate, sodium bromide and bromine in a solvent like methanol, preferably between 0° C. and room temperature gives the corresponding 4-thiocyanato-phenols; subsequent reduction with lithiumaluminium hydride in a solvent like tetrahydrofuran at temperatures around 0° C. liberates the corresponding 4-mercapto-phenol 1 ($R^{14}$=SH). Alternatively, intermediates carrying an aromatic SH moiety can be prepared from suitable intermediates carrying a phenolic hydroxyl function. In such intermediates, optionally carrying one or more protective functions, the phenolic OH group can be replaced by the corresponding aromatic SH function by methods known in the art. For example by a three step sequence as described in J. Labelled Compounds & Radiopharmaceuticals 43(7), 683-691, (2000): i) transformation of the phenol moiety into its trifluoromethanesulfonate (triflic anhydride, triethylamine, dichloromethane, at low temperature, preferably around −30° C.); ii) treatment of the triflate with triisopropylsilanethiolate, tetrakis(triphenyl-phosphine)-palladium(0) in solvent mixtures like toluene and tetrahydrofuran in a temperature range between 60° C. and 150° C.; iii) treatment of the silyl sulfide with hydrogen chloride in methanol preferably around 0° C. to liberate the phenolic SH moiety. Alternatively, thiocyanato phenols 1 can be hydrolyzed with NaOH in water at room temperature to reflux temperature and oxidized in DMSO at higher temperature, preferably around 95° C. to the dithiols 2 (step a). Thiophenols 1 described above can be oxidized to the dithiols 2 as well (step a). Reaction of phenols 2 with alpha halo esters or triflates of formula 3 in the presence of a base like potassium or cesium carbonate in solvents like acetone, methyl-ethyl ketone, acetonitrile or N,N-dimethylformamide in a temperature range between room temperature and 100° C. leads to the corresponding ether compounds 4 (step b). Dithiol reduction with (n-Bu$_3$PH)BF$_4$ and Hüinig's base in DMF at room temperature as described in the literature [Netherton, Matthew R.; Fu, Gregory C. Organic Letters (2001), 3(26), 4295-4298] yields thiophenols 5 ($R^{15}$=H) (step c). The reaction can also be carried out with acetic acid anhydride to give the stable compounds 5 ($R^{15}$=Ac) (step c).

Alkynes 6 (prepared as outlined in schemes 6 to 8) are condensed with thiophenols 5 ($R^{15}$=H) according to well known procedures (step d): if $R^{13}$ represents a hydroxy group e. g. via Mitsunobu-reaction, with triphenylphosphine and di-tert-butyl-, diisopropyl- or diethyl-azodicarboxylate as reagents; this transformation is preferably carried out in a solvent like toluene, dichloromethane or tetrahydrofuran at ambient temperature. Alternatively, if $R^{13}$ represents a halide, mesylate, tosylate or triflate moiety, alkynes 6 can be reacted with S-acetyl protected 5 ($R^{15}$=Ac) in solvents like N,N-dimethylformamide, dimethylsulfoxide, acetonitrile, acetone or methyl-ethyl ketone in the presence of methanol and a weak base like cesium or potassium carbonate at a temperature ranging from 0° C. to 140° C., preferably around room temperature to yield ether compounds Ii (step d). $R^{12}$ can also represent a protecting group, e. g. a trimethylsilyl group. Removal of the protecting group, e. g. by using n-Bu$_4$NF forms the free acetylene which can be modified via a Sonogashira reaction as described below to give new ether compounds Ii. This transformation can be performed either on esters Ii ($R^{12}$=H, $R^1$=alkyl) or on acids Ii ($R^{12}$=H, $R^1$=H). Alternatively, compounds 5 ($R^{15}$=H or Ac) can be reacted with alkynes 7 in analogy to the transformation described in step d to give alkynes 8 (step e). Intermediates 8 can be subjected to Sonogashira coupling conditions (e.g. see descriptions in schemes 6 and 7 or Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071) to give the final compounds Ii (step f). Alkynes 6 or 7 with R $^{13}$=OH can also be transformed in situ to the corresponding triflates by treatment with trifluoromethanesulfonic anhydride/2,6-di-tert-butylpyridine in CH$_2$Cl$_2$ at 0° C. to room temperature. The triflates are then reacted with thiophenols 5 ($R^{15}$=H) in solvents like N,N-dimethylformamide, dimethylsulfoxide, acetonitrile, acetone or methyl-ethyl ketone in the presence of a weak base like cesium or potassium carbonate at a temperature ranging from room temperature to 140° C., preferably around 50° C. to yield ether compounds Ii (step d or e). Esters of formula Ii can optionally be hydrolyzed according to standard procedures, e. g. by treatment with an alkali hydroxide like LiOH or NaOH in a polar solvent mixture like tetrahydrofuran/ethanol/water leading to carboxylic acids Ii.

An analogous reaction scheme with the same reaction sequence applies for the isomeric compound series leading to compounds of general formula I, particularly compounds according to formula Ik:

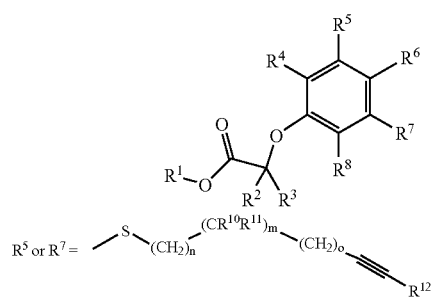

Ik

Compounds of the general formula I with $X^1$=S can be prepared from the appropriate thiophenol precursors which themselves can be obtained by converting suitable phenol intermediates into the corresponding thiophenols applying methods described above.

Compounds of the general formula I can contain one or more stereocenters and can optionally be separated into optically pure enantiomers or diastereomers by methods well known in the art, e. g. by HPLC chromatography, chromatography on a chiral HPLC column, chromatography with a chiral eluant or by derivatization with an optically pure alcohol to form esters, which can be separated by conventional HPLC chromatography and then converted back to the enantiomerically pure acids I ($R^1$=H). In addition, racemic compounds can be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine.

Schemes 6 to 8 describe the synthesis of alkyne building blocks 5 and 6 (scheme 1), identical to 11 and 12 (scheme 3), 6 and 7 (scheme 5) and acid-5 and amine-building blocks 6 (scheme 4).

Scheme 6

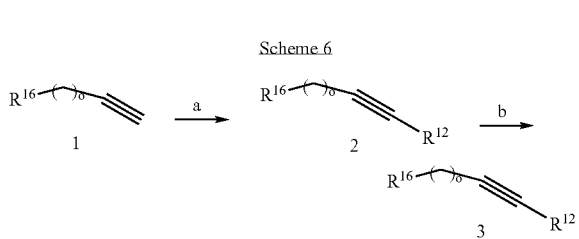

Hydroxy alkynes 1 ($R^{16}$=OH) or amino alkynes 1 ($R^{16}$=NHR$^9$ or N-protected NR$^9$) or alkyne esters 1 ($R^{16}$=COOalkyl) are known or can be prepared by methods known in the art. Alkynes 1 undergo palladium- and copper mediated coupling reactions with halo aryls or halo heteroaryls to give alkynes 2 (step a) wherein $R^{12}$ is aryl or heteroaryl. These Sonogashira couplings are preferably performed using catalytic amounts of Pd(PPh$_3$)$_4$/CuI at 45° C. to 80° C. in piperidine, in analogy to a literature procedure [Stara, Irena G.; Stary, Ivo; Kollarovic, Adrian; Teply, Filip; Saman, David; Fiedler, Pavel. Collect. Czech. Chem. Commun. (1999), 64(4), 649-672], Pd(PPh$_3$)$_4$/CuI/Et$_3$N at room temperature in DMF [Natchus, Michael G.; Bookland, Roger G.; Laufersweiler, Matthew J.; Pikul, Staszek; Almstead, Neil G.; De, Biswanath; Janusz, Michael J.; Hsieh, Lily C.; Gu, Fei; Pokross, Matthew E.; Patel, Vikram S.; Garver, Susan M.; Peng, Sean X.; Branch, Todd M.; King, Selane L.; Baker, Timothy R.; Foltz, David J.; Mieling, Glen E. Journal of Medicinal Chemistry (2001), 44(7), 1060-1071] or Pd(PPh$_3$)$_2$Cl$_2$/CuI/Et$_3$N at room temperature in acetonitrile or THF [Thorand, Stephan; Krause, Norbert; Journal of Organic Chemistry (1998), 63(23), 8551-8553] (step a).

Finally, the alcohols 2 ($R^{16}$=OH) of scheme 6 can be converted into compounds of formula 3 ($R^{16}$=OMesylate, Op-Tosylate, Halide or Triflate), e. g. by treatment with methanesulfonyl chloride or p-toluenesulfonyl chloride in dichloromethane in the presence of a base like triethylamine preferably in a temperature range between −20° C. and room temperature or by treatment with thionyl chloride in dichloromethane at 0° C. to room temperature or by reaction with carbon tetrachloride or carbon tetrabromide and triphenylphosphine in solvents like tetrahydrofuran preferably in a temperature range between room temperature and the reflux temperature of the solvents or by treatment with triflic anhydride, 2,6-lutidine and 4-dimethylaminopyridine in dichloromethane between −30° C. and room temperature; thus yielding compounds of formula 3 as methane-sulfonates, p-toluene sulfonates, chlorides, bromides or triflates, respectively (step b). Deprotection of esters 2 ($R^{16}$=COOalkyl) or amines 2 ($R^{16}$=N-protected NR$^9$) yields acids 3 ($R^{16}$=COOH) or amines 3 ($R^{16}$=NHR$^9$) and can be accomplished using procedures well known in the art (step b). All reactions described in scheme 6 are compatible with terminal alkynes, therefore in scheme 6 $R^{12}$ can also be a hydrogen atom.

Scheme 7

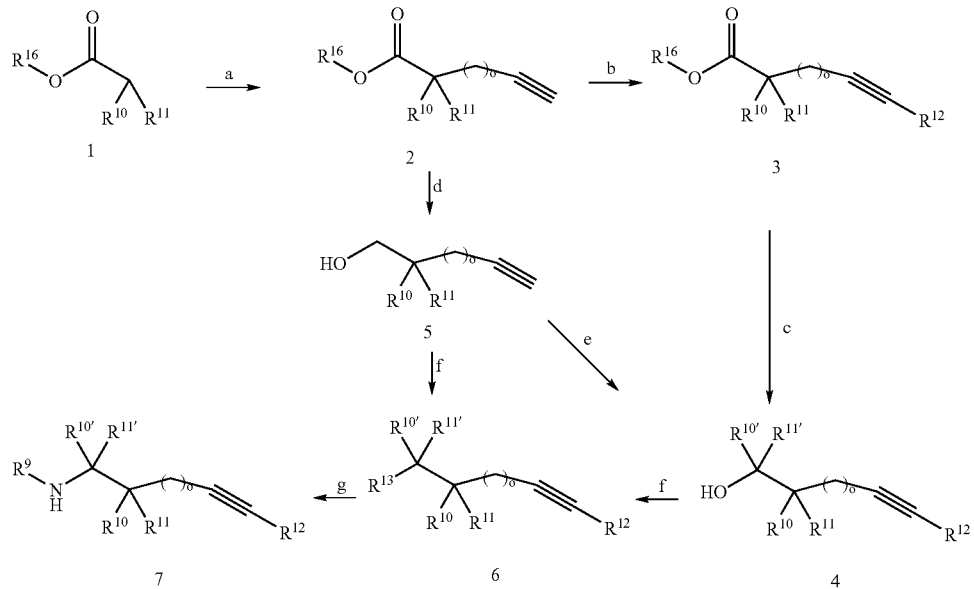

Alpha mono- or di-substituted esters 2 ($R^{10}$ and/or $R^{11} \neq H$) can be synthesized via treatment of esters 1 ($R^{16} \neq H$) with a base like LDA or HMDS in solvents like tetrahydrofuran or 1,2-dimethoxyethane, followed by addition of one or sequentially two different alkyl halides and one alkyne halide (o>0) at temperatures between −78° C. and room temperature, optionally using DMPU or HMPA as cosolvents (step a, scheme 7). To synthesize alkynes 2 with o being 0 3-butynoic acid derivatives can be alkylated at the alpha carbon atom with $R^{10}$- and/or $R^{11}$-alkyl halides by methods known in the art. Sonogashira coupling as described in step a of scheme 6 provides alkynes 3 (step b). Alternatively, alkyne 3 can be synthesized directly from ester 1 using an appropriate alkyne halide. $R^{12}$ can also represent a protecting group, e.g. a trimethylsilyl group. Removal of the protecting group, e.g. by using n-Bu$_4$NF can optionally be performed on each of the intermediates 3, 4 or 7 to give the free acetylene which can be modified via a Sonogashira reaction as described in step a of scheme 6 to form new intermediates 3, 4 or 7. Hydrolysis of esters 2 or 3 gives access to acids 2 or 3 ($R^{16}$=H; acid building block 5 used in scheme 4). Compounds 2 or 3 can be chiral and can optionally be separated into optically pure antipodes by methods well known in the art, e.g. chromatography on a chiral HPLC column, or by derivatization with an optically pure alcohol to form esters, which can be separated by conventional HPLC chromatography and then converted back to the enantiomerically pure acid. In addition, compounds 1 can be converted into chiral amides which can be used for asymmetric alkylation reactions being well known to a person skilled in the art. Esters 3 can subsequently be reduced with lithiumaluminium hydride at −78° C. to 0° C., preferable at −20° C. in solvents like THF to give alcohols 4 ($R^{10'}=R^{11'}$=H) (step c). Esters 3 ($R^{16} \neq H$) can further be converted into tertiary alcohols 4 with $R^{11'}=R^{11'}$ through reaction with alkyl organometallic reagents, preferably using alkyl Grignard compounds in a solvent like tetrahydrofuran or ether, preferably between −15° C. and the reflux temperature of the solvent (step c); $R^{10'}$ and $R^{11'}$ represent substituents as defined for $R^{10}$ and $R^{11}$. Alcohols 4 with $R^{10'}$ not equal to $R^{11'}$ can be prepared by a sequential procedure: i) saponification to the acid; ii) treatment with $R^{10'}$Li, optionally in the presence of a Cu(I) salt, in ether or tetrahydrofuran to yield the alkyl ketones —COR$^{10'}$; iii) subsequent reaction with $R^{11'}$Li or lithium aluminium hydride in ether or tetrahydrofuran (step c). In addition, esters 3 can be converted to secondary alcohols 4 ($R^{10'} \neq H$; $R^{11'}$=H) by a two step procedure: i) reduction to the corresponding aldehydes by methods known in the art, e.g. by treatment with diisobutylaluminium hydride at temperatures preferably around −70° C.; ii) conversion of the aldehydes to the corresponding secondary alcohols 4 through reaction with alkyl organometallic compounds, preferably under the conditions given for the transformation of esters 3 to tertiary alcohols 4 described above (step c); this step can optionally be carried out in enantioselective or diastereoseletive fashion using methods well known to a person skilled in the art. Esters 3 can also be converted to secondary alcohols 4 by standard Weinreb synthesis: i) saponification to the acid; ii) Weinreb amide formation with methoxy-methylamine; iii) reaction with an organolithium reagent and subsequent diisobultylaluminium hydride reduction to the alcohols 4 (step c). Alternatively, alkynes 2 can first be reduced with lithiumaluminium hydride to form alcohols 5 (step d), which undergo Sonogashira coupling reactions as described in step a of scheme 6 to yield building blocks 4 (step e). Alcohols 4 and 5 can be converted to the activated building blocks of formula 6 ($R^{13}$=OMesylate, Op-Tosylate, Halide or Triflate), e.g. by treatment with methanesulfonyl chloride or p-toluenesulfonyl chloride in dichloromethane in the presence of a base like triethylamine or pyridine preferably in a temperature range between −20° C. and room temperature possibly followed by Finkelstein reaction with sodium iodide in 2-butanone at reflux temperature or by treatment with trifluoromethanesulfonic anhydride/2,6-di-tert-butylpyridine in CH$_2$Cl$_2$ at 0° C. to give compounds 6 as methane-sulfonates, p-toluene-sulfonates, iodides or triflates, respectively (step f). Compounds of formula 6 can further be converted to amines 7 in solvents like DMA, DMF or dichloromethane at room temperature using an excess of the corresponding amine (step g). All reactions described in scheme 7 are compatible with terminal alkynes, therefore in scheme 7 $R^{12}$ can also be a hydrogen atom.

conventional HPLC chromatography. Alpha mono- or di-substituted acids 6 ($R^{10'}$ and/or $R^{11'} \neq H$; $R^{10'} = R^{10}$ as defined at the beginning; $R^{11'} = R^{11}$ as defined at the beginning) can be synthesized via transforming acids 4 into the corresponding esters, treating them with a base like LDA or HMDS in

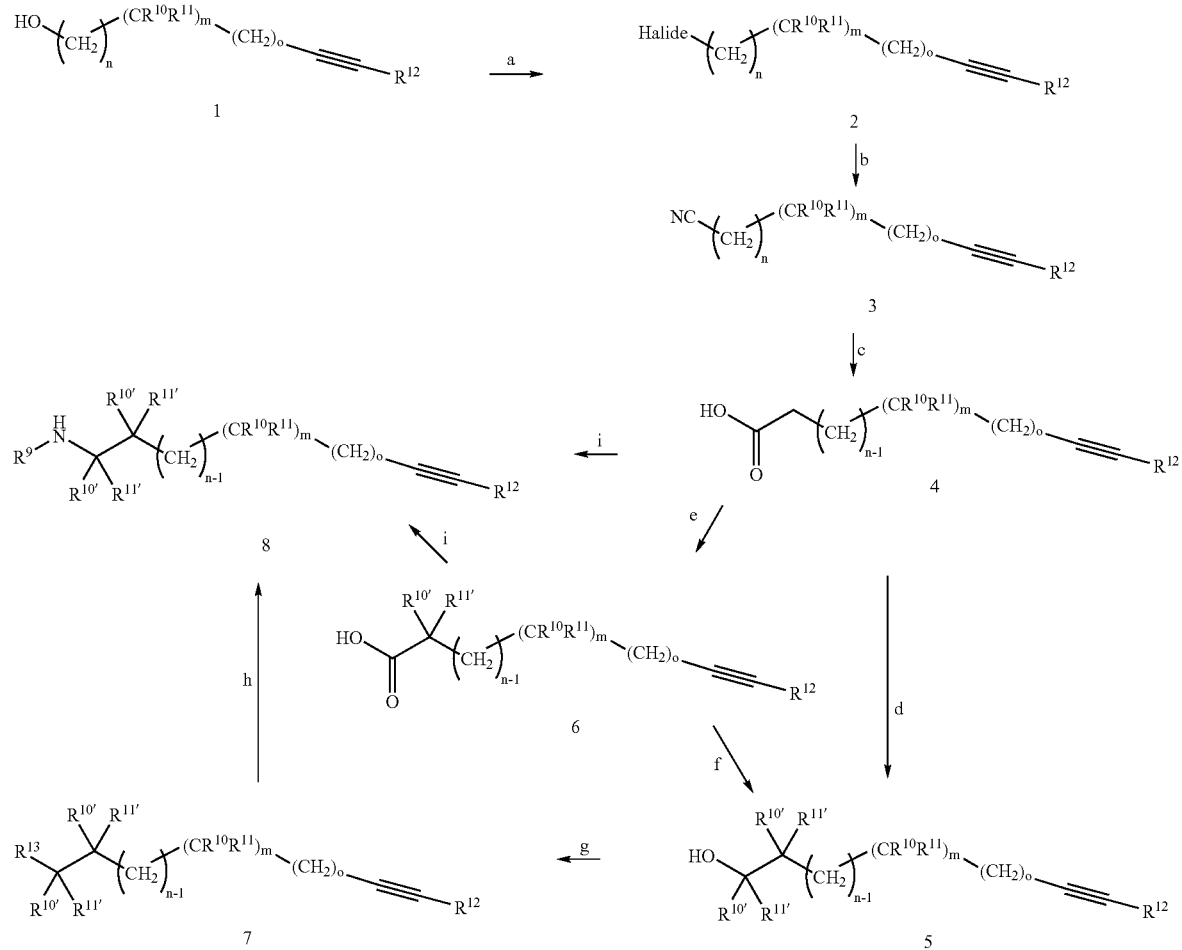

Scheme 8

Alcohols 1 (alcohols 2 in scheme 6 and alcohols 4 or 5 in scheme 7) comprising a chain length m, n and o can be converted into analogues with a chain length of m+1 or n+1 carbon atoms by methods well known in the art, e. g. by conversion of the primary hydroxy group of 1 into a suitable leaving group, e. g. a halide 2 (step a), followed by reaction with cyanide to form nitriles 3 (step b) and saponification to acids 4 (step c). Acids 4 can be further transformed into primary alcohols 5 ($R^{10'}=H$, $R^{11'}=H$), e. g. via esterification and subsequent lithiumaluminium hydride reduction (step d). Optionally, such alcohols 5 can be elongated to a chain length of n+1 carbon atoms by repeating the reaction sequence described for the synthesis of alcohols 5 from alcohols 1. The alcohol compounds 5 containing one or more chiral centers can optionally be separated into optically pure enantiomers or diastereomers by methods well known in the art, e. g. via HPLC chromatography, chromatography on a chiral HPLC column, or by derivatization with an optically pure acid to form esters, which can be separated by solvents like tetrahydrofuran or 1,2-dimethoxyethane, followed by addition of one or sequentially two different alkyl halides, a reaction preferably performed between −78° C. and room temperature followed by ester hydrolysis to obtain acids 6 (step e). The corresponding esters of acids 6 can serve as starting materials to introduce additional substituents $R^{10'}$ and $R^{11'}$ as described in step c of scheme 7.

Compounds 6 can contain one or more stereocenters and can optionally be separated into optically pure enantiomers or diastereomers by methods well known in the art, e. g. by HPLC chromatography, chromatography on a chiral HPLC column, or by derivatization with an optically pure alcohol to form esters, which can be separated by conventional HPLC chromatography and then converted back to the enantiomerically pure acids 6. In addition, compounds 4 can be converted into chiral amides which can be used for asymmetric alkylation reactions being well known to a person skilled in the art. Esterification of acids 6 and subsequent lithiumaluminium hydride reduction gives alcohols 5 (step f). Acid 6 can also be converted to secondary alcohols 5 by standard Weinreb synthesis: i) Weinreb amide formation with methoxy-methylamine; ii) reaction with an organolithium reagent and subsequent diisobultylaluminium hydride reduction to the alcohols 5 (step f). This step can optionally be carried out in enantioselective or diastereoselective fashion using methods well known to a person skilled in the art. Alcohols 5 can be converted to activated building blocks of formula 7 ($R^{13}$=OMesylate, Op-Tosylate, Halide or Triflate), e. g. by treatment with methanesulfonyl chloride or p-toluenesulfonyl chloride in dichloromethane in the presence of a base like triethylamine or pyridine preferably in a temperature range between –20° C. and room temperature, optionally followed by Finkelstein reaction with sodium iodide in 2-butanone at reflux temperature or by treatment with trifluoromethanesulfonic anhydride/2,6-di-tert-butylpyridine in $CH_2Cl_2$ at 0° C. to give compounds 7 as methane-sulfonates, p-toluene-sulfonates, iodides or triflates, respectively (step g). Compounds of formula 7 can further be converted to amines 8 in solvents like DMA, DMF or dichloromethane at room temperature with an excess of the corresponding amine (step h). Amines 8 can also be synthesized from acids 4 or 6 via formation of the corresponding amide which is subsequently reduced using methods well known to a person skilled in the art (step i). All reactions described in scheme 8 are compatible with terminal alkynes ($R^{12}$=H) except for step e where the terminal alkyne needs to be protected applying methods well known in the art, e. g. the use of a trimethylsilyl protection group.

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula (I).

The following examples serve to illustrate the present invention in more detail. They are, however, not intended to limit its scope in any manner.

EXAMPLES

Abbreviations:
EtOAc=ethyl acetate, n-BuLi=n-butyllithium, DEAD=diethyl azodicarboxylate, DIAD=diisopropyl azodicarboxylate, DIBAL-H solution=diisobutylaluminum hydride solution, DMF=N,N-dimethylformamide, DMPU=1,3-dimethyl-3,4,5,6-tetrahydro-2(1H)-pyrimidinone, eq.=equivalents, h=hour(s), DMSO=dimethyl sulfoxide, EDCI=N-(3-dimethylaminopropyl)-N'-ethylcarbodiimide hydrochloride, HPLC=high performance liquid chromatography, HMDS=hexamethyl disilazane, HMPA=hexamethylphosphortriamide, i. V.=in vacuo, LDA=lithium diisopropylamide, $PdCl_2(Ph_3P)_2$=dichlorobis(triphenylphosphine)palladium(II), $Pd(Ph_3P)_4$=tetrakis(triphenylphosphine)palladium, $POCl_3$=phosphorous oxychloride, RT=room temperature, TBME=tert-butyl methyl ether, TFA=trifluoroacetic acid, TFAA=trifluoroacetic anhydride, THF=tetrahydrofuran.

Example 1

2-Methyl-2-{2-methyl-4-[5-(4-trifluoromethoxy-phenyl)-pent-4-ynylsulfanyl]-phenoxy}-propionic acid A] 4,4'-Dithiodi-o-cresol To a stirred solution of 33.0 g (825.6 mmol) NaOH in 200 ml water was added 44.0 g (266.3 mmol) of 2-methyl-4-thiocyanato-phenol at 85° C. [Wei, Zhi-Liang; Kozikowski, Alan P., A Short and Efficient Synthesis of the Pharmacological Research Tool GW501516 for the Peroxisome Proliferator-Activated Receptor delta, Journal of Organic Chemistry (2003), 68(23), 9116-9118]. The temperature was raised to 95° C. and the mixture stirred over night. After cooling (10° C.), ether and 90 ml of aqueous conc. HCl were added. The water phase was extracted with ether (two times). The organic phase was washed with brine, dried ($Na_2SO_4$) and evaporated. The residue was dissolved in 300 ml of DMSO and heated for 2 h at 95° C. Subsequently, the solution was poured onto ice water and extracted with three 1 l portions of TBME. The organic layers were washed with 700 ml of water, dried ($Na_2SO_4$) and evaporated to give 42.1 g of the title compound.

B] 2-{4-[4-(1-Ethoxycarbonyl-1-methyl-ethoxy)-3-methyl-phenyldisulfanyl]-2-methyl-phenoxy}-2-methyl-propionic acid ethyl ester To a solution of 25.0 g (89.8 mmol) 4,4'-dithiodi-o-cresol and 52.7 ml (360 mmol) ethyl-bromoisobutyrate in 600 ml DMF 117 g (360 mmol) cesium carbonate were slowly added at 45° C. The reaction mixture was stirred for 5 h at 45° C., filtered, evaporated and then partitioned between EtOAc and aqueous sat. NH$_4$Cl-solution. Twofold extraction with EtOAc, washing with water, drying (Na$_2$SO$_4$) and evaporation of the solvents followed by flash chromatography (SiO$_2$, n-hexane/EtOAc 5:1) yielded 21.6 g of pure title compound.

C] 2-(4-Acetylsulfanyl-2-methyl-phenoxy)-2-methyl-propionic acid ethyl ester

A solution of 9.2 g (31.7 mmol) of [(n-Bu)$_3$PH]BF$_4$ [Netherton, Matthew R.; Fu, Gregory C., Air-Stable Trialkylphosphonium Salts: Simple, Practical, and Versatile Replacements for Air-Sensitive Trialkylphosphines. Applications in Stoichiometric and Catalytic Processes, Organic Letters (2001), 3(26), 4295-42981 in 150 ml DMF (degassed with argon) was added to 11.5 g (22.6 mmol) of 2-{4-[4-(1-ethoxycarbonyl-1-methyl-ethoxy)-3-methyl-phenyldisulfanyl]-2-methyl-phenoxy}-2-methyl-propionic acid ethyl ester. 5.43 ml (31.7 mmol) N-ethyldiisopropylamine and 0.416 ml (23.1 mmol) of water were added. After 2 h 40 min, 5.14 ml (54.4 mmol) of acetic acid anhydride were added and after 1 h 20 min, the reaction was diluted with isobutyl acetate, washed with 0.1N HCl and brine. The organic phase was dried (Na$_2$SO$_4$), concentrated under reduced pressure and purified by chromatography over silica gel with EtOAc/n-heptane 1:4, to give 12.56 g of the title compound as colorless oil.

MS: 319 (M+Na)$^+$.

D] 2-Methyl-2-{2-methyl-4-[5-(4-trifluoromethoxy-phenyl)-pent-4-ynylsulfanyl]-phenoxy-propionic acid ethyl ester 0.150 g (0.47 mmol) of methanesulfonic acid 5-(4-trifluoromethoxy-phenyl)-pent-4-ynyl ester (example 1G]) and 0.115 g (0.39 mmol) of 2-(4-acetylsulfanyl-2-methyl-phenoxy)-2-methyl-propionic acid ethyl ester (example 1C]) were dissolved in 1.0 ml of acetonitrile and 0.1 ml of MeOH and treated with 0.07 g (0.47 mmol) of NaI and 0.177 g (0.54 mmol) of Cs$_2$CO$_3$. After vigorous stirring for 2 days at ambient temperature and filtration, the solvent was evaporated and the residue redissolved in dichloromethane and filtered again and evaporated. Purification by flash chromatography (SiO$_2$, dichloromethane/n-heptane 1:1) afforded 0.118 g of the title compound as light yellow oil.

MS: 480.2 (M)$^+$.

E] 2-Methyl-2-{2-methyl-4-[5-(4-trifluoromethoxy-phenyl)-pent-4-ynylsulfanyl]-phenoxy}-propionic acid 0.105 g (0.22 mmol) of the above prepared 2-methyl-2-{2-methyl-4-[5-(4-trifluoromethoxy-phenyl)-pent-4-ynyl-sulfanyl]-phenoxy}-propionic acid ethyl ester was dissolved in 4 ml of THF/EtOH (1:1), treated at 0° C. with 0.66 ml (0.66 mmol) of 1N LiOH, and kept at ambient temperature for 22 h. The reaction mixture was taken up in ether and washed with aqueous 10% KHSO$_4$ solution and aqueous 10% NaCl solution. The water phases were extracted with ether (two times). The organic phase was dried (Na$_2$SO$_4$) and evaporated. The crude product was precipitated in pentane (RT to 4° C.) and decanted to give 28 mg of the title compound as colorless oil.

MS: 451.1 (M–H)$^-$.

Methanesulfonic acid 5-(4-trifluoromethoxy-phenyl)-pent-4-ynyl ester used in 1D] was prepared as follows:

F] 5-(4-Trifluoromethoxy-phenyl)-pent-4-yn-1-ol

A mixture of 5 g (17 mmol) 1-iodo-3-trifluoromethoxy-benzene, 973 mg (1 mmol) Pd(PPh$_3$)$_4$ and 160 mg (1 mmol) cuprous iodide in 130 ml piperidine was stirred for 30 min at 50° C. under an argon atmosphere. 2.125 g (25 mmol) 4-Pentyn-1-ol was added within 60 min at 50° C. The temperature was raised to 80° C. and the mixture was stirred for 3 h at this temperature. The reaction mixture was cooled to ambient temperature, poured into a solution of saturated aqueous 10% KHSO$_4$/ice water 1/1 and extracted two times with tert butyl methyl ether. The combined extracts were washed with water and brine (two times) and dried over sodium sulfate. The solvent was removed under reduced pressure and the residue purified by column chromatography (silica gel, heptane/AcOEt) to give 3.4 g of the title compound as orange oil.

MS: 244.2 (M)$^+$.

G] Methanesulfonic acid 5-(4-trifluoromethoxy-phenyl)-pent-4-ynyl ester

To an ice-cooled solution of 2.02 g (8.3 mmol) of 5-(4-trifluoromethoxy-phenyl)-pent-4-yn-1-ol and 1.73 ml (12.4 mmol) of Et$_3$N in 100 ml of dichloromethane were added 0.67 ml (8.7 mmol) of methanesulfonyl chloride under stirring within 15 min keeping the temperature at 0-10° C. The reaction mixture was stirred at RT for 1 h 15 min. Water was added and after 5 min, the reaction was then partitioned between ether and water. The water was extracted again with ether (two times), the organic phases were washed with aqueous 10% NaCl, dried (Na$_2$SO$_4$) and concentrated to yield 2.50 g of the title compound as light brown oil.

MS: 322.1 (M)$^+$.

Example 2

2-Methyl-2-{2-methyl-4-[4-(4-trifluoromethyl-phenyl)-but-3-ynylsulfanyl]-phenoxy}-propionic acid A] 2-Methyl-2-{2-methyl-4-[4-(4-trifluoromethyl-phenyl)-but-3-ynylsulfanyl]-phenoxy}-propionic acid ethyl ester In analogy to the procedure described in example 1D], 2-(4-acetylsulfanyl-2-methyl-phenoxy)-2-methyl-propionic acid ethyl ester (example 1C]) was reacted with 1-(4-iodo-but-1-ynyl)-4-trifluoromethyl-benzene (example 2E]) to give the title compound as colorless oil.

MS: 450.2 (M)$^+$.

B] 2-Methyl-2-{2-methyl-4-[4-(4-trifluoromethyl-phenyl)-but-3-ynylsulfanyl]-phenoxy}-propionic acid In analogy to the procedure described in example 1E], saponification of 2-methyl-2-{2-methyl-4-[4-(4-trifluoromethyl-phenyl)-but-3-ynylsulfanyl]-phenoxy}-propionic acid ethyl ester yielded the title compound as light yellow oil.

MS: 421.1 (M–H)$^-$.

1-(4-Iodo-but-1-ynyl)-4-trifluoromethyl-benzene used in 2A] was prepared as follows:

C] 4-(4-Trifluoromethyl-phenyl)-but-3-yn-1-ol

The synthesis was performed following a procedure of Stara, Irena G.; Stary, Ivo; Kollarovic, Adrian; Teply, Filip; Saman, David; Fiedler, Pavel, Coupling reactions of halobenzenes with alkynes. The synthesis of phenylacetylenes and symmetrical or unsymmetrical 1,2-diphenylacetylenes, Collect. Czech. Chem. Commun. (1999), 64(4), 649-672. To a degassed (argon) solution of 5.0 g (17.83 mmol) 1-iodo-4-trifluoromethyl-benzene in 65 ml piperidine was added 1.03 g (0.89 mmol) Pd(PPh$_3$)$_4$ and 0.17 g (0.89 mmol) CuI. The reaction mixture was stirred at 50° C. for 10 min, then 2.03 ml (26.75 mmol) of but-3-yn-1-ol were added dropwise within 1 h. During the addition of but-3-yn-1-ol the oil bath was slowly heated to 80° C. starting after 30 min. The reaction mixture was stirred at this temperature for 3 h and then extracted with chilled aqueous 10% KHSO$_4$/Et$_2$O (three times). The organic phases were washed with aqueous 10% NaCl, dried (Na$_2$SO$_4$) and evaporated. Purification by flash-chromatography on silica gel (n-heptane/EtOAc 9:1 to 4:1) yielded 3.58 g of the title compound as a yellow solid.
MS: 214.0 (M)$^+$.

D] Methanesulfonic acid 4-(4-trifluoromethyl-phenyl)-but-3-ynyl ester

In analogy to the procedure described in example 1G], 4-(4-trifluoromethyl-phenyl)-but-3-yn-1-ol and methanesulfonyl chloride gave the title compound as light yellow oil.
MS: 291.7 (M)$^+$.

E] 1-(4-Iodo-but-1-ynyl)-4-trifluoromethyl-benzene

To a solution of 3.16 g (10.81 mmol) methanesulfonic acid 4-(4-trifluoromethyl-phenyl)-but-3-ynyl ester in 100 ml 2-butanone was added 3.24 g (21.62 mmol) NaI. The mixture was heated for 2 h at 90° C. The solvent was evaporated and the residue suspended in dichloromethane, ether was added and the suspension was filtrated. Evaporation of the organic phase gave 3.46 g of the title compound as an orange liquid.
MS: 323.9 (M)$^+$.

Example 3

2-Methyl-2-[2-methyl-4-[5-(3-trifluoromethoxy-phenyl)-pent-4-ynylsulfanyl[-phenoxy}-propionic acid A] 2-Methyl-2-{2-methyl-4-[5-(3-trifluoromethoxy-phenyl)-pent-4-ynylsulfanyl]-phenoxy}-propionic acid ethyl ester In analogy to the procedure described in example 1D], 2-(4-acetylsulfanyl-2-methyl-phenoxy)-2-methyl-propionic acid ethyl ester (example 1C]) was reacted with methanesulfonic acid 5-(3-trifluoromethoxy-phenyl)-pent-4-ynyl ester (example 3D]) to give 2-methyl-2-{2-methyl-4-[5-(3-trifluoromethoxy-phenyl)-pent-4-ynylsulfanyl]-phenoxy}-propionic acid ethyl ester as light brown oil.
MS: 480.3 (M)$^+$.

B] 2-Methyl-2-{2-methyl-4-[5-(3-trifluoromethoxy-phenyl)-pent-4-ynylsulfanyl]-phenoxy}-propionic acid In analogy to the procedure described in example 1E], saponification of 2-methyl-2-{2-methyl-4-[5-(3-trifluoromethoxy-phenyl)-pent-4-ynylsulfanyl]-phenoxy}-propionic acid ethyl ester yielded the title compound as colorless oil.
MS: 451.1 (M–H)$^-$.

Methanesulfonic acid 5-(3-trifluoromethoxy-phenyl)-pent-4-ynyl ester used in 3A] was prepared as follows:

C] 5-(3-Trifluoromethoxy-phenyl)-pent-4-yn-1-ol

In analogy to the procedures described in example 1F], 1-iodo-3-trifluoromethoxy-benzene and pent-4-yn-1-ol gave the title compound as a red liquid.
MS 245.3 (M+H)$^{30}$ D] Methanesulfonic acid 5-(3-trifluoromethoxy-phenyl)-pent-4-ynyl ester In analogy to the procedure described in example 1G], 5-(3-trifluoromethoxy-phenyl)-pent-4-yn-1-ol and methanesulfonyl chloride gave the title compound as a light brown oil.
MS 243.1 (M–CH$_3$SO$_2$)$^+$.

Example 4

{2-Methyl-4-[5-(4-trifluoromethoxy-phenyl)-pent-4-ynylsulfanyl]-phenoxy}-acetic acid A] (4-Acetylsulfanyl-2-methyl-phenoxy)-acetic acid tert-butyl ester Analogously to example 1B] and example 1C], 4,4'-dithiodi-o-cresol (example 1A]) and tert-butyl bromoacetate gave the title compound as white solid.
MS: 319 (M+Na)$^+$.

B] {2-Methyl-4-[5-(4-trifluoromethoxy-phenyl)-pent-4-ynylsulfanyl]-phenoxy}-acetic acid tert-butyl ester In analogy to the procedure described in example 1D], (4-acetylsulfanyl-2-methyl-phenoxy)-acetic acid tert-butyl ester (example 4A]) was reacted with methanesulfonic acid 5-(4-trifluoromethoxy-phenyl)-pent-4-ynyl ester (example 1G]) to give the title compound a light yellow oil.
MS: 480.3 (M)$^+$.

C] 2-Methyl-2-{2-methyl-4-[5-(3-trifluoromethoxy-phenyl)-pent-4-ynylsulfanyl]-phenoxy-propionic acid In analogy to the procedure described in example 1E], saponification of {2-methyl-4-[5-(4-trifluoromethoxy-phenyl)-pent-4-ynylsulfanyl]-phenoxy}-acetic acid tert-butyl ester followed by crystallization (ether/n-pentane) yielded the title compound as white crystals, mp. 94-95° C.
MS: 423.0 (M–H)$^-$.

Example 5

{2-Methyl-4-[3-(4-trifluoromethyl-phenyl)-prop-2-ynylsulfanyl]-phenoxy}-acetic acid A] (2-Methyl-4-prop-2-ynylsulfanyl-phenoxy)-acetic acid tert-butyl ester 3.50 g (11.81 mmol) of (4-acetylsulfanyl-2-methyl-phenoxy)-acetic acid tert-butyl ester (example 4A]) and 1.97 ml (17.71 mmol) of propargyl bromide were dissolved in 60 ml of acetonitrile and 3 ml of MeOH and treated with 6.62 g (14.17 mmol) Cs$_2$CO$_3$. After vigorous stirring for 3 h at ambient temperature and filtration, the solvent was evaporated and the residue redissolved in EtOAc. The organic phase was washed with aqueous 1N NaOH (two times) and aqueous 10% NaCl. After extraction of the water phases with EtOAc (two times), the organic phase was dried (Na$_2$SO$_4$) and evaporated to give 3.48 g of the title compound as a yellow oil.
MS: 293.1 (M+H)$^+$.

B] {2-Methyl-4-[3-(4-trifluoromethyl-phenyl)-prop-2-ynylsulfanyl]-phenoxy}-acetic acid tert-butyl ester A degassed (argon) solution of 96.0 mg (0.33 mmol) (2-methyl-4-prop-2-ynylsulfanyl-phenoxy)-acetic acid tert-butyl ester, 0.053 ml (0.36 mmol) 1-iodo-4-trifluoromethyl-benzene and 0.086 (0.621 mmol) Et$_3$N in 1 ml DMF was treated with 37.9 mg (0.03 mmol) Pd(PPh$_3$)$_4$ and 12.5 mg (0.07 mmol) of CuI. After stirring for 2 h at room temperature, the reaction was distributed between 1N HCl and ether (three times). Washing of the organic layer with saturated aqueous NH$_4$Cl solution and brine, drying (Na$_2$SO$_4$) and evaporation of the solvents, followed by flash chromatography (SiO$_2$, n-heptane/EtOAc 1 to 5%), yielded 76 mg of the title compound as yellow oil.
MS: 437.4 (M+H)$^+$.

C] {2-Methyl-4-[3-(4-trifluoromethyl-phenyl)-prop-2-ynyl-sulfanyl]-phenoxy}-acetic acid A solution of 75 mg (1.7 mmol) of the above prepared {2-methyl-4-[3-(4-trifluoromethyl-phenyl)-prop-2-ynylsulfanyl]-phenoxy}-acetic acid tert-butyl ester in 2 ml dichloromethane was treated at 0° C. with 0.4 ml TFA and stirred at RT for 3 h. The reaction was evaporated, dissolved in toluene and evaporated again (two times). Purification by flash chromatography on $SiO_2$ with a gradient of $CH_2Cl_2$/MeOH (98:2 to 9:1) yielded 30 mg of the title compound as white crystals, mp. 130-131° C.

MS: 379.2 (M–H)⁻.

Example 6

{2-Methyl-4-[3-(3-trifluoromethyl-phenyl)-prop-2-ynylsulfanyl]-phenoxy}-acetic acid A] {2-Methyl-4-[3-(3-trifluoromethyl-phenyl)-prop-2-ynyl-sulfanyl]-phenoxy}-acetic acid tert-butyl ester In analogy to the procedure described in example 5B], (2-methyl-4-prop-2-ynylsulfanyl-phenoxy)-acetic acid tert-butyl ester (example 5A]) and 1-iodo-3-trifluoromethyl-benzene gave the title compound as a colorless oil.

MS: 437.2 (M+H)⁺.

B] {2-Methyl-4-[3-(3-trifluoromethyl-phenyl)-prop-2-ynyl-sulfanyl]-phenoxy}-acetic acid In analogy to the procedure described in example 5C], {2-methyl-4-[3-(3-trifluoromethyl-phenyl)-prop-2-ynylsulfanyl]-phenoxy}-acetic acid tert-butyl ester gave the title compound as a white solid, mp. 81-82° C.

MS: 379.0 (M–H)⁻.

Example 7

{2-Methyl-4-[3-(2-trifluoromethyl-phenyl)-prop-2-ynylsulfanyl]-phenoxy}-acetic acid A] {2-Methyl-4-[3-(2-trifluoromethyl-phenyl)-prop-2-ynyl-sulfanyl]-phenoxy}-acetic acid tert-butyl ester In analogy to the procedure described in example 5B], (2-methyl-4-prop-2-ynylsulfanyl-phenoxy)-acetic acid tert-butyl ester (example 5A]) and 1-iodo-2-trifluoromethyl-benzene gave the title compound as a light yellow oil.

MS: 437.2 (M+H)⁺.

B] [2-Methyl-4-[3-(2-trifluoromethyl-phenyl)-prop-2-ynyl-sulfanyl]-phenoxy}-acetic acid In analogy to the procedures described in example 5C], {2-methyl-4-[3-(2-trifluoromethyl-phenyl)-prop-2-ynylsul-fanyl]-phenoxy}-acetic acid tert-butyl ester gave the title compound as an off-white solid, mp. 95-97° C.

MS: 379.0 (M–H)⁻.

Example 8

{4-[3-(4-Chloro-phenyl)-prop-2-ynylsulfanyl]-2-methyl-phenoxy}-acetic acid

A] {4-[3-(4-Chloro-phenyl)-prop-2-ynylsulfanyl]-2-methyl-phenoxy}-acetic acid tert-butyl ester In analogy to the procedure described in example 5B], (2-methyl-4-prop-2-ynylsulfanyl-phenoxy)-acetic acid tert-butyl ester (example 5A]) and 1-chloro-4-iodo-benzene gave the title compound as a light yellow oil.

MS: 403.3 (M+H, 1Cl)⁺.

B] {4-[3-(4-Chloro-phenyl)-prop-2-ynylsulfanyl]-2-methyl-phenoxy}-acetic acid

In analogy to the procedure described in example 5C], {4-[3-(4-chloro-phenyl)-prop-2-ynylsulfanyl]-2-methyl-phenoxy}-acetic acid tert-butyl ester gave the title compound as a light brown solid, mp. 106-108° C.

MS: 345.0 (M–H, 1Cl)⁻.

Example 9

{4-[3-(4-Methoxy-phenyl)-prop-2-ynylsulfanyl]-2-methyl-phenoxy}-acetic acid

A] {4-[3-(4-Methoxy-phenyl)-prop-2-ynylsulfanyl]-2-methyl-phenoxy}-acetic acid tert-butyl ester In analogy to the procedure described in example 5B], (2-methyl-4-prop-2-ynylsulfanyl-phenoxy)-acetic acid tert-butyl ester (example 5A]) and 1-iodo-4-methoxy-benzene gave the title compound as a yellow oil.

MS: 399.2 (M+H)⁺.

B] {4-[3-(4-Methoxy-phenyl)-prop-2-ynylsulfanyl]-2-methyl-phenoxy}-acetic acid

In analogy to the procedure described in example 1E], {4-[3-(4-methoxy-phenyl)-prop-2-ynylsulfanyl]-2-methyl-phenoxy}-acetic acid tert-butyl ester gave the title compound as an orange solid, mp. 143-144° C.

MS: 343.1 (M+H)⁺.

Example 10

[2-Methyl-4-(3-phenyl-prop-2-ynylsulfanyl)-phenoxy]-acetic acid

A] [2-Methyl-4-(3-phenyl-prop-2-ynylsulfanyl)-phenoxy]-acetic acid tert-butyl ester In analogy to the procedure described in example 5B], (2-methyl-4-prop-2-ynylsulfanyl-phenoxy)-acetic acid tert-butyl ester (example 5A]) and iodo-benzene gave the title compound as a colorless oil.

MS: 369.1 (M+H)⁺.

B] [2-Methyl-4-(3-phenyl-prop-2-ynylsulfanyl)-phenoxy]-acetic acid

In analogy to the procedure described in example 1E], [2-methyl-4-(3-phenyl-prop-2-ynylsulfanyl)-phenoxy]-acetic acid tert-butyl ester gave the title compound as a yellow solid, mp. 90-92° C.

MS: 311.1 (M–H)⁻.

Example 11

{4-[3-(4-Fluoro-phenyl)-prop-2-ynylsulfanyl]-2-methyl-phenoxy}-acetic acid

A] {4-[3-(4-Fluoro-phenyl)-prop-2-ynylsulfanyl]-2-methyl-phenoxy}-acetic acid tert-butyl ester In analogy to the procedure described in example 5B], (2-methyl-4-prop-2-ynylsulfanyl-phenoxy)-acetic acid tert-butyl ester (example 5A]) and 1-fluoro-4-iodo-benzene gave the title compound as a yellow oil.

MS: 387.2 (M+H)⁺.

B] {4-[3-(4-Fluoro-phenyl)-prop-2-ynylsulfanyl]-2-methyl-phenoxy}-acetic acid

In analogy to the procedure described in example 1E], {4-[3-(4-fluoro-phenyl)-prop-2-ynylsulfanyl]-2-methyl-phenoxy}-acetic acid tert-butyl ester gave the title compound as a yellow oil.

MS: 329.2 (M–H)⁻.

Example 12

{2-Methyl-4-[4-(4-trifluoromethyl-phenyl)-but-3-ynylsulfanyl]-phenoxy}-acetic acid A] (4-But-3-ynylsulfanyl-2-methyl-phenoxy)-acetic acid tert-butyl ester In analogy to the procedure described in example 5A], (4-acetylsulfanyl-2-methyl-phenoxy)-acetic acid tert-butyl ester (example 4A]) and 4-chloro-but-1-yne gave the title compound as orange oil.

MS: 307.2 (M+H)⁺.

B] {2-Methyl-4-[4-(4-trifluoromethyl-phenyl)-but-3-ynylsulfanyl]-phenoxy}-acetic acid tert-butyl ester In analogy to the procedure described in example 5B], (4-but-3-ynylsulfanyl-2-methyl-phenoxy)-acetic acid tert-butyl ester (example 12A]) and 1-fluoro-4-iodo-benzene gave the title compound as a yellow oil.

MS: 450.2 (M)⁺.

C] {2-Methyl-4-[4-(4-trifluoromethyl-phenyl)-but-3-ynylsulfanyl]-phenoxy}-acetic acid In analogy to the procedure described in example 1E], {2-methyl-4-[4-(4-trifluoromethyl-phenyl)-but-3-ynylsulfanyl]-phenoxy}-acetic acid tert-butyl ester gave the title compound as white powder, mp. 129-130° C.

MS: 392.9 (M–H)⁻.

Example 13

2-Methyl-2-{2-methyl-4-[5-(4-trifluoromethoxy-phenyl)-pent-4-ynyloxy]-phenoxy}-propionic acid A] 2-Methyl-2-(2-methyl-4-pent-4-ynyloxy-phenoxy)-propionic acid ethyl ester To a solution of 0.95 g (4.0 mmol) 2-(4-hydroxy-2-methyl-phenoxy)-2-methyl-propionic acid ethyl ester (described in WO 02/092590) and 0.42 ml (4.0 mmol) 5-chloro-pent-1-yne in 20 ml acetonitrile were added 0.60 g (4.0 mmol) NaI and 1.56 g (4.80 mmol) $Cs_2CO_3$. The mixture was stirred at 50° C. for 3 days and every day 0.42 ml (4.0 mmol) 5-chloro-pent-1-yne and 1.56 g (4.80 mmol) $Cs_2CO_3$ were added (two times). After 2 further days stirring at ambient temperature and filtration, the solvent was evaporated. The residue was redissolved in dichloromethane, dried ($Na_2SO_4$), filtered and evaporated. Purification by flash chromatography ($SiO_2$, n-heptane/EtOAc 2.5 to 5%) yielded 1.11 g of the title compound as colorless oil.

MS: 304.1 (M)⁺.

B] 2-Methyl-2-{2-methyl-4-[5-(4-trifluoromethoxy-phenyl)-pent-4-ynyloxy]-phenoxy}-propionic acid ethyl ester The synthesis was performed following a procedure of Stara, Irena G.; Stary, Ivo; Kollarovic, Adrian; Teply, Filip; Saman, David; Fiedler, Pavel, Coupling reactions of halobenzenes with alkynes. The synthesis of phenylacetylenes and symmetrical or unsymmetrical 1,2-diphenylacetylenes, Collect. Czech. Chem. Commun. (1999), 64(4), 649-672. To a degassed (argon) solution of 178 mg (0.60 mmol) 1-iodo-4-trifluoromethoxy-benzene in 2 ml piperidine was added 29 mg (0.03 mmol) $Pd(PPh_3)_4$ and 5 mg (0.03 mmol) CuI. The reaction mixture was stirred at 50° C. for 10 min, then a solution of 152 mg (0.50 mmol) 2-methyl-2-(2-methyl-4-pent-4-ynyloxy-phenoxy)-propionic acid ethyl ester (example 13A]) in 2 ml piperidine was added dropwise within 1 h. During the addition the oil bath was slowly heated to 80° C. starting after 30 min. The reaction mixture was stirred at this temperature for 3 h and then extracted with chilled aqueous 10% $KHSO_4/Et_2O$ (three times). The organic phases were washed with aqueous 10% NaCl, dried ($Na_2SO_4$) and evaporated. Purification by flash-chromatography on silica gel (n-heptane/EtOAc 95:5 to 9:1) yielded 190 mg of the title compound as a light yellow viscous oil.

MS: 464.3 (M)⁺.

C] 2-Methyl-2-{2-methyl-4-[5-(4-trifluoromethoxy-phenyl)-pent-4-ynyloxy]-phenoxy}-propionic acid In analogy to the procedure described in example 1E], 2-methyl-2-{2-methyl-4-[5-(4-trifluoromethoxy-phenyl)-pent-4-ynyloxy]-phenoxy}-propionic acid ethyl ester was hydrolyzed to give the title compound as a white powder, mp. 90-91° C., dec.

MS: 435.2 (M–H)⁻.

Example 14

2-Methyl-2-{2-methyl-4-[5-(4-trifluoromethyl-phenyl)-pent-4-ynyloxy]-phenoxy}-propionic acid A] 2-Methyl-2-{2-methyl-4-[5-(4-trifluoromethyl-phenyl)-pent-4-ynyloxy]-phenoxy}-propionic acid ethyl ester In analogy to the procedure described in example 13B], 2-methyl-2-(2-methyl-4-pent-4-ynyloxy-phenoxy)-propionic acid ethyl ester (example 13A]) and 1-iodo-4-trifluoromethyl-benzene gave the title compound as a light yellow viscous oil.

MS: 448.3 (M)⁺.

B] 2-Methyl-2-{2-methyl-4-[5-(4-trifluoromethyl-phenyl)-pent-4-ynyloxy]-phenoxy}-propionic acid In analogy to the procedure described in example 1E], 2-methyl-2-{2-methyl-4-[5-(4-trifluoromethyl-phenyl)-pent-4-ynyloxy]-phenoxy}-propionic acid ethyl ester was hydrolyzed to give the title compound as a white powder, mp. 114-115° C., dec.

MS: 419.1 (M–H)⁻.

Example 15

2-{4-[5-(4-Chloro-phenyl)-pent-4-ynyloxy]-2-methyl-phenoxy}-2-methyl-propionic acid A] 2-{4-[5-(4-Chloro-phenyl)-pent-4-ynyloxy]-2-methyl-phenoxy}-2-methyl-propionic acid ethyl ester In analogy to the procedure described in example 13B], 2-methyl-2-(2-methyl-4-pent-4-ynyloxy-phenoxy)-propionic acid ethyl ester (example 13A]) and 1-chloro-4-iodo-benzene gave the title compound as a yellow viscous oil.

MS: 414.3 (M, 1Cl)⁺.

B] 2-{4-[5-(4-Chloro-phenyl)-pent-4-ynyloxy]-2-methyl-phenoxy}-2-methyl-propionic acid In analogy to the procedure described in example 1E], 2-{4-[5-(4-chloro-phenyl)-pent-4-ynyloxy]-2-methyl-phenoxy}-2-methyl-propionic acid ethyl ester was hydrolyzed to give the title compound as an off-white powder, mp. 119-120° C., dec.

MS: 385.1 (M–H, 1Cl)⁻.

Example 16

2-Methyl-2-{2-methyl-4-[4-(4-trifluoromethyl-phenyl)-but-3-ynyloxy]-phenoxy}-propionic acid A] 2-(4-But-3-ynyloxy-2-methyl-phenoxy)-2-methyl-propionic acid ethyl ester 2.38 g (10.00 mmol) 2-(4-hydroxy-2-methyl-phenoxy)-2-methyl-propionic acid ethyl ester (described in WO 02/092590) and 1.63 g (5.00 mmol) $Cs_2CO_3$ were heated in 25 ml acetonitrile at reflux for 5 min. 2.34 (10.0 mmol) 3-Butynyl tosylate was added and heating was continued for 2.5 h. Then 1.63 g (5.00 mmol) $Cs_2CO_3$ and 2.34 (10.0 mmol) of 3-butynyl tosylate were added and the mixture was stirred at 60° C. (2.5 h). The temperature was raised to 95° C. and stirring continued for 12 h. Every 3 h 1.63 g (5.0 mmol) $Cs_2CO_3$ and 2.34 g (10.0 mmol) of 3-butynyl tosylate were added. The solvent was evaporated and the residue was redissolved in dichloromethane, dried ($Na_2SO_4$), filtered and evaporated. Purification by flash chromatography ($SiO_2$, n-heptane/EtOAc 2.5%) yielded 0.67 g of the title compound as light yellow oil.

MS: 290.2 (M)⁺.

B] 2-Methyl-2-{2-methyl-4-[4-(4-trifluoromethyl-phenyl)-but-3-ynylox]-phenoxy}-propionic acid ethyl ester In analogy to the procedure described in example 13B], 2-(4-but-3-ynyloxy-2-methyl-phenoxy)-2-methyl-propionic acid ethyl ester (example 16A]) and 1-iodo-4-trifluoromethyl-benzene gave the title compound as a yellow viscous oil.

MS: 434.2 (M)⁺.

C] 2-Methyl-2-{2-methyl-4-[4-(4-trifluoromethyl-phenyl)-but-3-ynylox]-phenoxy}-propionic acid In analogy to the procedure described in example 1E], 2-methyl-2-{2-methyl-4-[4-(4-trifluoromethyl-phenyl)-but-3-ynyloxy]-phenoxy}-propionic acid ethyl ester was hydrolyzed to give the title compound as light yellow viscous oil.

MS: 405.3 (M–H)⁻.

Example 17

2-Methyl-2-{2-methyl-4-[4-(4-trifluoromethoxy-phenyl)-but-3-ynyloxy]-phenoxy}-propionic acid A] 2-Methyl-2-{2-methyl-4-[4-(4-trifluoromethoxy-phenyl)-but-3-ynyloxy]-phenoxy}-propionic acid ethyl ester In analogy to the procedure described in example 13B], 2-(4-but-3-ynyloxy-2-methyl-phenoxy)-2-methyl-propionic acid ethyl ester (example 16A]) and 1-iodo-4-trifluoromethoxy-benzene gave the title compound as a light yellow viscous oil.

MS: 450.2 (M)⁺.

B] 2-Methyl-2-{2-methyl-4-[4-(4-trifluoromethoxy-phenyl)-but-3-ynyloxy]-phenoxy}-propionic acid In analogy to the procedure described in example 1E], 2-methyl-2-{2-methyl-4-[4-(4-trifluoromethoxy-phenyl)-but-3-ynyloxy]-phenoxy}-propionic acid ethyl ester was hydrolyzed to give the title compound as a white powder, mp. 62-71° C., slow dec.

MS: 421.2 (M–H)⁻.

Example 18

2-{4-[4-(4-Chloro-phenyl)-but-3-ynyloxy]-2-methyl-phenoxy}-2-methyl-propionic acid A] 2-{4-[4-(4-Chloro-phenyl)-but-3-ynyloxy]-2-methyl-phenoxy}-2-methyl-propionic acid ethyl ester In analogy to the procedure described in example 13B], 2-(4-but-3-ynyloxy-2-methyl-phenoxy)-2-methyl-propionic acid ethyl ester (example 16A]) and 1-chloro-4-iodo-benzene gave the title compound as a light yellow viscous oil.

MS: 400.2 (M, 1Cl)⁺.

B] 2-{4-[4-(4-Chloro-phenyl)-but-3-ynyloxy]-2-methyl-phenoxy}-2-methyl-propionic acid In analogy to the procedure described in example 1E], 2-{4-[4-(4-chloro-phenyl)-but-3-ynyloxy]-2-methyl-phenoxy}-2-methyl-propionic acid ethyl ester was hydrolyzed to give the title compound as white powder, mp. 68-69° C., dec.

MS: 371.0 (M–H, 1Cl)⁻.

Example 19

2-Methyl-2-{2-methyl-4-[5-(5-trifluoromethyl-pyridin-2-yl)-pent-4-ynyloxy]-phenoxy}-propionic acid A] 2-Methyl-2-{2-methyl-4-[5-(5-trifluoromethyl-pyridin-2-yl)-pent-4-ynyloxy]-phenoxy}-propionic acid ethyl ester A degassed (argon) solution of 152 mg (0.50 mmol) 2-methyl-2-(2-methyl-4-pent-4-ynyloxy-phenoxy)-propionic acid ethyl ester (example 13A]), 124 mg (0.55 mmol) 2-bromo-5-(trifluoromethyl)pyridine and 0.21 ml (1.5 mmol) $Et_3N$ in 5 ml acetonitrile was treated with 18 mg (0.03 mmol) of $PdCl_2(PPh_3)_2$ and 3 mg (0.03 mmol) of CuI. After stirring for 3 h at room temperature the reaction mixture was partitioned between cold aqueous 10% $KHSO_4$ and ether (three times). Washing of the organic layer with aqueous 10% NaCl solution, drying ($Na_2SO_4$) and evaporation of the solvents, followed by flash chromatography ($SiO_2$, n-heptane/EtOAc 95:5 to 9:1) yielded 170 mg of the title compound as yellow viscous oil.

MS: 450.4 (M+H)⁺.

B] 2-Methyl-2-{2-methyl-4-[5-(5-trifluoromethyl-pyridin-2-yl)-pent-4-ynyloxy]-phenoxy}-propionic acid In analogy to the procedure described in example 1E], 2-methyl-2-{2-methyl-4-[5-(5-trifluoromethyl-pyridin-2-yl)-pent-4-ynyloxy]-phenoxy}-propionic acid ethyl ester was hydrolyzed to give the title compound as orange viscous oil.

MS: 420.1 (M–H)⁻.

Example 20

{2-Methyl-4-[5-(4-trifluoromethoxy-phenyl)-pent-4-ynyloxy]-phenoxy}-acetic acid

A] {2-Methyl-4-[5-(4-trifluoromethoxy-phenyl)-pent-4-ynyloxy]-phenoxy}-acetic acid ethyl ester To a solution of 110 mg (0.52 mmol) (4-hydroxy-2-methyl-phenoxy)-acetic acid ethyl ester (WO02092590) and 169 mg (0.52 mmol) methanesulfonic acid 5-(4-trifluoromethoxy-phenyl)-pent-4-ynyl ester (example 1G]) in 5 ml acetonitrile were added 15.7 mg (0.10 mmol) NaI and 188 mg (0.58 mmol) $Cs_2CO_3$. The mixture was stirred at room temperature for 2 days and for 4.75 h at reflux. After filtration, the solvent was evaporated. The residue was redissolved in dichloromethane, dried ($Na_2SO_4$), filtered and evaporated. Purification by flash chromatography ($SiO_2$, n-heptane/EtOAc 95:5) yielded 143 mg of the title compound as light yellow oil.

MS: 436.2 (M)$^+$.

B] {2-Methyl-4-[5-(4-trifluoromethoxy-phenyl)-pent-4-ynyloxy]-phenoxy}-acetic acid In analogy to the procedure described in example 1E], {2-methyl-4-[5-(4-trifluoromethoxy-phenyl)-pent-4-ynyloxy]-phenoxy}-acetic acid ethyl ester was hydrolyzed to give the title compound as white crystals, mp. 124.6-126.7° C.

MS: 408.2 (M)$^+$.

Example 21

2-{2,5-Dichloro-4-[5-(4-trifluoromethoxy-phenyl)-pent-4-ynyloxy]-phenoxy}-2-methyl-propionic acid A] Benzoic acid 2,5-dichloro-4-(1-ethoxycarbonyl-1-methyl-ethoxy)-phenyl ester To a suspension of 1.4 g (5 mmol) benzoic acid 2,5-dichloro-4-hydroxy-phenyl ester (D. Koike, *Gunma Daigaku Kyoyobu Kiyo* 1968, 2, 13-28), 2.6 g (7.9 mmol) cesium carbonate and a trace of potassium iodide in 80 ml acetonitrile under an argon atmosphere was added 1.1 ml (7.4 mmol) bromo-acetic acid ethyl ester. The mixture was stirred for 14 h at ambient temperature, poured onto 1 N HCl/ice water 1/1 and extracted two times with ethyl acetate. The combined organic layers were washed with brine/water 1/1 and dried over sodium sulfate. The solvent was removed under reduced pressure and the residue purified by column chromatography (silica gel, heptane/AcOEt) to give 0.5 g (1.3 mmol, 25%) of the title compound as colorless oil.

MS: 396.1 (M, 1Cl)$^+$.

B] 2-(2,5-Dichloro-4-hydroxy-phenoxy)-2-methyl-propionic acid methyl ester

To an ice cold solution of 500 mg (1.3 mmol) benzoic acid 2,5-dichloro-4-(1-ethoxycarbonyl-1-methyl-ethoxy)-phenyl ester in 11.5 ml methanol was added a solution of 145 mg (6.3 mmol) sodium in 11.5 ml methanol within 5 min under an argon atmosphere. The solution was stirred for 4 h at ambient temperature, cooled to 0° C. and carefully neutralized with 1 N HCl. The solvent was removed under reduced pressure and the residue was dissolved in ethyl acetate and brine/ice water 1/1. The layers were separated and the aqueous layer was extracted two times with ethyl acetate. The combined organic layers were washed with brine/ice water 1/1 and dried over sodium sulfate. The solvent was removed under reduced pressure and the residue purified by column chromatography (silica gel, heptane/AcOEt) to give 219 mg (0.8 mmol, 62%) of the title compound as colorless oil.

MS: 279.1 (M+H, 1Cl)$^+$.

C] 2-{2,5-Dichloro-4-[5-(4-trifluoromethoxy-phenyl)-pent-4-ynyloxy]-phenoxy}-2-methyl-propionic acid methyl ester In analogy to the procedure described in. example 20A], 2-(2,5-dichloro-4-hydroxy-phenoxy)-2-methyl-propionic acid methyl ester was treated with methanesulfonic acid 5-(4-trifluoromethoxy-phenyl)-pent-4-ynyl ester (example 1G]) in acetonitrile at the reflux temperature of the solvent for 3 h to give the title compound as colorless oil.

MS: 505.3 (M+H, 1Cl)$^+$.

D] 2-{2,5-Dichloro-4-[5-(4-trifluoromethoxy-phenyl)-pent-4-ynyloxy]-phenoxy}-2-methyl-propionic acid In analogy to the procedure described in example 1E], 2-{2,5-dichloro-4-[5-(4-trifluoromethoxy-phenyl)-pent-4-ynyloxy]-phenoxy}-2-methyl-propionic acid methyl ester was hydrolyzed to give the title compound as colorless oil.

MS: 508.5 (M+$NH_4$, 1Cl)$^+$.

Example 22

2-Methyl-2-{2-methyl-4-[5-(3-trifluoromethoxy-phenyl)-pent-4-ynyloxy]-phenoxy}-propionic acid A] 2-Methyl-2-{2-methyl-4-[5-(3-trifluoromethoxy-phenyl)-pent-4-ynyloxy]-phenoxy}-propionic acid ethyl ester To an ice cold solution of 50 mg (0.21 mmol) 2-(4-hydroxy-2-methyl-phenoxy)-2-methyl-propionic acid ethyl ester (described in WO 02/092590), 48 mg (0.21 mmol) 5-(3-trifluoromethoxy-phenyl)-pent-4-yn-1-ol (example 3C]) and 70 μl (0.25 mmol) tributylphosphine (50 19 μmol) in 5 ml tetrahydrofuran were added 43 mg (0.25 mmol) N,N,N',N'-tetramethyl azodicarboxamide. The cooling bath was removed and stirring continued for 14 h. The mixture was filtered over celite and the solvent removed under reduced pressure to give a yellow oil which was purified by column chromatography (silica gel, heptane/AcOEt) to obtain 34 mg (80 μmol, 36%) of the title compound as colorless oil.

MS: 465.4 (M+H)$^+$.

B] 2-Methyl-2-{2-methyl-4-[5-(3-trifluoromethoxy-phenyl)-pent-4-ynyloxy]-phenoxy}-propionic acid In analogy to the procedure described in example 1E], 2-methyl-2-{2-methyl-4-[5-(3-trifluoromethoxy-phenyl)-pent-4-ynyloxy]-phenoxy}-propionic acid ethyl ester was hydrolyzed to give the title compound as colorless oil.

MS: 435.1 (M−H)$^−$.

Example 23

2-Methyl-2-{2-methyl-4-[5-(3-trifluoromethyl-phenyl)-pent-4-ynyloxy]-phenoxy}-propionic acid A] 5-(3-Trifluoromethyl-phenyl)-pent-4-yn-1-ol In analogy to the procedure described in example 1F], 1-iodo-3-trifluoromethyl-benzene, was reacted with 4-pentyn-1-ol in the presence of Pd(PPh$_3$)$_4$ and cuprous iodide to yield the title compound as brown oil.

MS: 228.2 (M)$^+$.

B] 2-Methyl-2-{2-methyl-4-[5-(3-trifluoromethyl-phenyl)-pent-4-ynyloxy]-phenoxy}-propionic acid ethyl ester In analogy to the procedure described for example 21A], 2-(4-hydroxy-2-methyl-phenoxy)-2-methyl-propionic acid ethyl ester (described in WO 02/092590) was reacted with 5-(3-trifluoromethyl-phenyl)-pent-4-yn-1-ol in the presence of N,N,N',N'-tetramethyl azodicarboxamide and tributylphosphine to give the title compound as colorless oil.

MS: 449.4 (M+H)$^+$.

C] 2-Methyl-2-{2-methyl-4-[5-(3-trifluoromethyl-phenyl)-pent-4-ynyloxy]-phenoxy}-propionic acid In analogy to the procedure described in example 1E], 2-methyl-2-{2-methyl-4-[5-(3-trifluoromethyl-phenyl)-pent-4-ynyloxy]-phenoxy}-propionic acid ethyl ester was hydrolyzed to give the title compound as colorless oil.

MS: 421.1 (M+H)$^+$.

Example 24

2-{4-[2,2-Dimethyl-5-(4-trifluoromethoxy-phenyl)-pent-4-ynyloxy]-2-methyl-phenoxy}-2-methyl-propionic acid A] 2-{4-[2,2-Dimethyl-5-(4-trifluoromethoxy-phenyl)-pent-4-ynyloxy]-2-methyl-phenoxy}-2-methyl-propionic acid ethyl ester A solution of 0.082 g (0.30 mmol) 2,2-dimethyl-5-(4-trifluoromethoxy-phenyl)-pent-4-yn-1-ol (example 24E]) in 0.3 ml $CH_2Cl_2$ was treated at 0° C. with 0.08 ml (0.36 mmol) 2,6-di-tert-butylpyridine and 0.05 ml (0.33 mmol) trifluoromethanesulfonic anhydride. After 2.5 h at 0° C. and 0.5 h at room temperature the solution was evaporated, dissolved in 1 ml acetonitrile and added to a solution of 0.071 g (0.30 mmol) 2-(4-hydroxy-2-methyl-phenoxy)-2-methyl-propionic acid ethyl ester (described in WO 02/092590) and 0.205 g (0.63 mmol) $Cs_2CO_3$ in 2 ml acetonitrile. The mixture was stirred for 20 h at room temperature and 1 h at reflux temperature. After filtration, the residue was dissolved in dichloromethane, dried ($Na_2SO_4$), filtered and evaporated. Purification by flash chromatography ($SiO_2$, n-heptane/EtOAc 2%) yielded 0.096 g of the title compound as light yellow oil.

MS: 492.3 $(M)^+$.

B] 2-{4-[2,2-Dimethyl-5-(4-trifluoromethoxy-phenyl)-pent-4-ynyloxy]-2-methyl-phenoxy}-2-methyl-propionic acid In analogy to the procedure described in example 1E], saponification of 2-{4-[2,2-dimethyl-5-(4-trifluoromethoxy-phenyl)-pent-4-ynyloxy]-2-methyl-phenoxy}-2-methyl-propionic acid ethyl ester yielded the title compound as light yellow oil.

MS: 463.1 $(M-H)^-$.

2,2-Dimethyl-5-(4-trifluoromethoxy-phenyl)-pent-4-yn-1-ol used in 24A] was prepared as follows:

C] 2,2-Dimethyl-pent-4-ynoic acid ethyl ester

The synthesis was performed following a procedure of Crimmins, Michael T.; Mascarella, S. Wayne; DeLoach, Joe A., *Journal of Organic Chemistry* 1984, 49(16), 3033-5.

A solution of 22.0 ml (2.0 M in THF/n-heptane/ethylbenzene, 44 mmol) LDA in 40 ml THF was treated during 10 min at −78° C. with 5.47 ml (40 mmol) ethyl isobutyrate in 4.7 ml THF. After 1 h at this temperature, a solution of 4.90 ml (80% by weight in toluene, 44 mmol) of propargyl bromide in 7.5 ml THF was added dropwise. The solution was naturally warmed to 0° C. and after 2 h treated carefully with aqueous 10% $KHSO_4$ and extracted with ether (three times). The organic phases were washed with aqueous 10% $KHSO_4$ and aqueous 10% NaCl solution. The organic phase was dried ($Na_2SO_4$) and evaporated to give 5.70 g of the title compound as volatile orange liquid.

GC/MS: 154 $(M)^+$.

D] 2,2-Dimethyl-pent-4-yn-1-ol 3.86 g (25 mmol) of the above synthesized 2,2-dimethyl-pent-4-ynoic acid ethyl ester in 200 ml of abs. THF was cooled to −20° C. and treated slowly (15 min) with 30 ml (1.0 M in THF, 30 mmol) of LAH-solution. The reaction was stirred for 20 min at this temperature, cooled (−78° C.) and hydrolyzed with a suspension of 8.3 g $MgSO_4.7H_2O$, 8.3 g silicagel in 13 ml of aqueous 10% $KHSO_4$. The cooling bath was removed, THF was added and water, the mixture was stirred for 30 min and filtered. After evaporation, the residue was dissolved in $CH_2Cl_2$, dried over $Na_2SO_4$ and evaporated to yield 2.75 g of the title compound as volatile orange liquid.

GC/MS: 112 $(M)^+$.

E] 2,2-Dimethyl-5-(4-trifluoromethoxy-phenyl)-pent-4-yn-1-ol

The synthesis was performed following a procedure of Stara, Irena G.; Stary, Ivo; Koilarovic, Adrian; Teply, Filip; Saman, David; Fiedler, Pavel, *Collect. Czech. Chem. Commun.* 1999, 64(4), 649-672.

To a degassed (argon) solution of 3.56 g (12.00 mmol) 1-iodo-4-trifluoromethoxy-benzene in 40 ml piperidine was added 0.58 g (0.50 mmol) $Pd(PPh_3)_4$ and 0.095 g. (0.50 mmol) CuI. The reaction mixture was stirred at 50° C. for 10 min, then 1.25 g (10.00 mmol) of above synthesized 2,2-dimethyl-pent-4-yn-1-ol in 20 ml of piperidine was added dropwise within 1 h. During the addition the oil bath was slowly heated to 80° C. starting after 30 min. The reaction mixture was stirred at this temperature for 2 h and then extracted with chilled aqueous 10% $KHSO_4$/ether (three times). The organic phases were washed with aqueous 10% NaCl, dried ($Na_2SO_4$) and evaporated. Purification by flash-chromatography on silica gel (n-heptane/EtOAc 2:1 to 1:1) yielded 1.91 g of the title compound as a yellow oil.

MS: 272.2 $(M)^+$.

Example 25

2-{4-[2,2-Dimethyl-5-(4-trifluoromethoxy-phenyl)-pent-4-ynylsulfanyl]-2-methyl-phenoxy}-2-methyl-propionic acid A] 2-{4-[2,2-Dimethyl-5-(4-trifluoromethoxy-phenyl)-pent-4-ynylsulfanyl]-2-methyl-phenoxy}-2-methyl-propionic acid ethyl ester A solution of 0.109 g (0.40 mmol) 2,2-dimethyl-5-(4-trifluoromethoxy-phenyl)-pent-4-yn-1-ol (example 24E]) in 0.4 ml $CH_2Cl_2$ was treated at 0° C. with 0.11 ml (0.48 mmol) 2,6-di-tert-butylpyridine and 0.07 ml (0.44 mmol) trifluoromethanesulfonic anhydride. After 1.5 h at 0° C. the solution was evaporated, dissolved in 1.5 ml acetonitrile and added to a suspension of 0.142 g (0.48 mmol) of 2-(4-acetylsulfanyl-2-methyl-phenoxy)-2-methyl-propionic acid ethyl ester (example 1C]) and 0.274 g (0.84 mmol) of $Cs_2CO_3$ in 2.5 ml of acetonitrile and 0.1 ml of MeOH. After vigorous stirring for 20 h at ambient temperature and filtration, the solvent was evaporated and the residue re-dissolved in dichloromethane and filtered again and evaporated. Purification by flash chromatography ($SiO_2$, n-heptane/EtOAc 2.5%) yielded 0.18 g of the title compound as colorless viscous oil.

MS: 509.4 $(M+H)^+$.

B] 2-{4-[2,2-Dimethyl-5-(4-trifluoromethoxy-phenyl)-pent-4-ynylsulfanyl]-2-methyl-phenoxy}-2-methyl-propionic acid In analogy to the procedure described in example 1E], saponification of 2-{4-[2,2-dimethyl-5-(4-trifluoromethoxy-phenyl)-pent-4-ynylsulfanyl]-2-methyl-phenoxy}-2-methyl-propionic acid ethyl ester yielded the title compound as light yellow viscous oil.

MS: 479.2 $(M-H)^-$.

Example 26

2-{4-[5-(3-Fluoro-phenyl)-pent-4-ynyloxy]-2-methyl-phenoxy}-2-methyl-propionic acid A] 2-{4-[5-(3-Fluoro-phenyl)-pent-4-ynyloxyl]-2-methyl-phenoxy}-2-methyl-propionic acid A degassed (argon) solution of 0.098 g (0.44 mmol) 1-fluoro-3-iodobenzene in 4 ml acetonitrile was treated with 0.111 g (0.40 mmol) 2-methyl-2-(2-methyl-4-pent-4-ynyloxy-phenoxy)-propionic acid (example 26B]), 0.014 g (0.02 mmol) PdCl$_2$(Ph$_3$P)$_2$, 0.004 g (0.02 mmol) of CuI and 0.17 ml (1.20 mmol) triethylamine. The reaction was stirred for 2.5 h and then extracted with chilled aqueous 10% KHSO$_4$/ether (three times). The organic phases were washed with aqueous 10% NaCl, dried (Na$_2$SO$_4$) and evaporated. Purification was done by flash-chromatography on silica gel (1. n-heptane/EtOAc 4:1 and 2. CH$_2$Cl$_2$/MeOH 2%-10%). The pure fractions were evaporated, dissolved in ether and washed with aqueous 10% KHSO$_4$/ether (three times). The organic phase was dried (Na$_2$SO$_4$) and evaporated to yield 0.10 g of the title compound as an orange viscous oil.

MS: 369.1 (M–H)$^-$.

2-Methyl-2-(2-methyl-4-pent-4-ynyloxy-phenoxy)-propionic acid used in 26A] was prepared as follows:

B] 2-Methyl-2-(2-methyl-4-pent-4-ynyloxy-phenoxy)-propionic acid

In analogy to the procedure described in example 1E], saponification of 2-methyl-2-(2-methyl-4-pent-4-ynyloxy-phenoxy)-propionic acid ethyl ester (example 13A]) yielded the title compound as light yellow viscous oil.

MS: 275.1 (M–H)$^-$.

Example 27

2-{4-[5-(4-Chloro-3-fluoro-phenyl)-pent-4-ynyloxy]-2-methyl-phenoxy}-2-methyl-propionic acid In analogy to the procedure described in example 24E], 1-chloro-2-fluoro-4-iodobenzene and 2-methyl-2-(2-methyl-4-pent-4-ynyloxy-phenoxy)-propionic acid (example 26B]), followed by purification described in example 26A] yielded the title compound as off-white powder, mp. 106-107° C., dec.

MS: 403.3 (M–H, 1Cl)$^-$.

Example 28

2-Methyl-2-{2-methyl-4-[5-(2-trifluoromethyl-pyrimidin-5-yl)-pent-4-ynyloxy]-phenoxy}-propionic acid A] 2-Methyl-2-{2-methyl-4-[5-(2-trifluoromethyl-pyrimidin-5-yl)-pent-4-ynyloxy]-phenoxy}-propionic acid In analogy to the procedure described in example 24E], 5-chloro-2-trifluoromethyl-pyrimidine (example 28B]) and 2-methyl-2-(2-methyl-4-pent-4-ynyloxy-phenoxy)-propionic acid (example 26B]), followed by flash chromatography (SiO$_2$, CH$_2$Cl$_2$/MeOH 2.5 to 10%) and precipitation ether/n-pentane yielded the title compound as white powder, mp. 95-97° C., dec.

MS: 421.1 (M–H)$^-$.

5-Chloro-2-trifluoromethyl-pyrimidine used in 28A] was prepared as follows:

B] 5-Chloro-2-trifluoromethyl-pyrimidine

A solution of 4.70 g (85% purity, 35.65 mmol) of trifluoroacetamidine and 10.93 g (35.65 mmol) of ((Z)-2-chloro-3-dimethylamino-allylidene)-dimethyl-ammonium; hexafluoro phosphate [Davies, Ian W.; Marcoux, Jean-Francois; Wu, Jimmy; Palucki, Michael; Corley, Edward G.; Robbins, Michael A.; Tsou, Nancy, Ball, Richard G.; Dormer, Peter; Larsen, Robert D.; Reider, Paul J, *Journal of Organic Chemistry* 2000, 65(15), 4571-4574] in 70 ml acetonitrile was treated with 4.33 ml (42.78 mol) of triethylamine and stirred for 4 h at room temperature. The reaction was poured into 250 ml of water and extracted with ether (three times). The organic phases were washed with water (two times), dried (Na$_2$SO$_4$) and carefully evaporated to give 3.66 g of the title compound as an orange volatile liquid.

MS: 182.0 (M, 1Cl)$^+$.

Example 29

2-Methyl-2-(4-{[5-(4-trifluoromethoxy-phenyl)-pent-4-ynoylamino]-methyl}-phenoxy)-propionic acid A] 2-Methyl-2-(4-{[5-(4-trifluoromethoxy-phenyl)-pent-4-ynoylamino]-methyl}-phenoxy)-propionic acid ethyl ester 0.16 g (0.68 mmol) of 2-(4-aminomethyl-phenoxy)-2-methyl-propionic acid ethyl ester [PCT Int. Appl. WO 2002/096895 A1] and 0.16 g (0.62 mmol) of 5-(4-trifluoromethoxy-phenyl)-pent-4-ynoic acid (example 29D]) were dissolved in 4 ml of dichloromethane. This solution was cooled to 0° C. and then 0.14 g (0.74 mmol) of N-(3-dimethylamino-propyl)-N'-ethyl-carbodiimide-hydrochloride was added and the reaction stirred for 28 hours at ambient temperature. It was subsequently poured into aqueous 10% KHSO$_4$/ether and extracted two fold with ether; the organic layers were washed with aqueous saturated NaHCO$_3$, dried (Na$_2$SO$_4$), filtered and evaporated. The crude product was purified by flash chromatography (SiO$_2$; n-heptane/AcOEt=9:1 to 1:2) to give 0.14 g of the title compound as light brown oil.

MS: 478.1 (M+H)$^+$.

B] 2-Methyl-2-(4-{[5-(4-trifluoromethoxy-phenyl)-pent-4-ynoylamino]-methyl}-phenoxy)-propionic acid In analogy to the procedure described in example 1E], saponification of 2-methyl-2-(4-{[5-(4-trifluoromethoxy-phenyl)-pent-4-ynoylamino]-methyl}-phenoxy)-propionic acid ethyl ester yielded the title compound as white crystals, mp. 127-128° C., dec.

MS: 467.1 (M+NH$_4$)$^+$.

5-(4-Trifluoromethoxy-phenyl)-pent-4-ynoic acid used in 29A] was prepared as follows:

C] 5-(4-Trifluoromethoxy-phenyl)-pent-4-ynoic acid methyl ester

In analogy to the procedure described in example 19A], pent-4-ynoic acid methyl ester [Wulff, W. D., McCallum, J., Stuart; Kunng, Fen Ann, *Journal of the American Chemical Society* 1988, 110(22), 7419-34] and 1-iodo-4-trifluoromethoxy-benzene yielded the title compound as a brown oil.

MS: 272.1 (M)$^+$

D] 5-(4-Trifluoromethoxy-phenyl)-pent-4-ynoic acid

In analogy to the procedure described in example 1E], saponification of 5-(4-trifluoromethoxy-phenyl)-pent-4-ynoic acid methyl ester yielded the title compound as light brown crystals.

MS: 256.9 (M–H)$^-$.

Example 30

2-Methyl-2-[4-({methyl-[5-(4-trifluoromethoxy-phenyl)-pent-4-ynoyl]-amino}-methyl)-phenoxy]-propionic acid A] (4-Hydroxy-benzyl)-carbamic acid tert-butyl ester A solution of 4.3 g (21 mmol) of 4-hydroxybenzylamine hydrobromide and 5.49 g (65 mmol) NaHCO$_3$ in 17 ml dioxane and 4 ml of water was treated with 5.06 g (23 mmol) di-tert-butyl dicarbonate and stirred for 4 h at room tem- B] 2-[4-(tert-Butoxycarbonylamino-methyl)-phenoxy]-2-methyl-propionic acid ethyl ester 5.85 g (26 mmol) of (4-hydroxy-benzyl)-carbamic acid tert-butyl ester and 10.14 ml (68 mmol) of ethyl-bromo isobutyrate were dissolved in 70 ml acetonitrile. Then 10.86 g (79 mmol) of potassium carbonate were added and the reaction mixture stirred for 20 h at 80° C. (reflux). It was then cooled down to ambient temperature and the solvent was evaporated. The residue was partitioned between water and ether and extracted twice with ether; the organic phases were washed with water, dried ($MgSO_4$) and evaporated. The crude product was purified by flash chromatography ($SiO_2$, n-heptane/AcOEt=4:1) to finally give 8.05 g of the title compound as colorless oil.

MS: 337.1 $(M)^+$.

C] 2-{4-[(tert-Butoxycarbonyl-methyl-amino)-methyl]-phenoxy}-2-methyl-propionic acid ethyl ester To an ice-cooled and stirred solution of 4.0 g (12 mmol) of the above prepared 2-[4-(tert-butoxycarbonylamino-methyl)-phenoxy]-2-methyl-propionic acid ethyl ester in 37 ml DMF was cooled (0° C.), and treated with 0.78 g (55% in oil, 18 mmol) of sodium hydride and, after 30 min, with 5.93 ml (95 mmol) of $CH_3I$. The reaction was stirred at 0° C. to room temperature for 16 h. Subsequently, the solution was poured onto ice water, adjusted to pH 1 (with aqueous 1N HCl) and extracted with ether (two times). The organic layers were washed with water, dried ($MgSO_4$), evaporated and purified by flash chromatography ($SiO_2$, heptane/AcOEt=9:1) to finally give 3.68 g of the title compound as colorless oil.

MS: 352.3 $(M+H)^+$.

D] 2-Methyl-2-(4-methylaminomethyl-phenoxy)-propionic acid ethyl ester

A solution of 3.66 g (10 mmol) of the above prepared 2-{4-[(tert-butoxycarbonyl-methyl-amino)-methyl]-phenoxy}-2-methyl-propionic acid ethyl ester in 50 ml dichloromethane was treated at 0° C. with 3.98 ml TFA and stirred at room temperature for 16 h. The reaction was evaporated and treated with ice water, neutralized with $NaHCO_3$ (pH=8) and extracted dichloromethane (two times). The organic phases were washed with water, dried ($MgSO_4$), and evaporated to give 2.77 g of crude product. Purification by flash chromatography on $SiO_2$ with $CH_2Cl_2$/MeOH (95:5) yielded 1.95 g of the title compound as brown-yellow oil.

MS: 252.2 $(M+H)^+$.

E] 2-Methyl-2-[4-({methyl-[5-(4-trifluoromethoxy-phenyl)-pent-4-ynoyl]-amino}-methyl)-phenoxy]-propionic acid ethyl ester In analogy to the procedures described in example 29A], 2-methyl-2-(4-methylaminomethyl-phenoxy)-propionic acid ethyl ester was reacted with 5-(4-trifluoromethoxy-phenyl)-pent-4-ynoic acid (example 29D]) to give the title compound as light brown oil.

MS: 492.2 $(M+H)^+$.

F] 2-Methyl-2-[4-({methyl-[5-(4-trifluoromethoxy-phenyl)-pent-4-ynoyl]-amino}-methyl)-phenoxy]-propionic acid In analogy to the procedure described in example 1E], saponification of 2-methyl-2-[4-({methyl-[5-(4-trifluoromethoxy-phenyl)-pent-4-ynoyl]-amino}-methyl)-phenoxy)-propionic acid ethyl ester yielded the title compound as off-white foam.

MS: 464.1 $(M+NH_4)^+$.

Example 31 rac-2-Methyl-2-{2-methyl-4-[1-methyl-5-(4-trifluoromethoxy-phenyl)-pent-4-ynyloxy]-phenoxy}-propionic acid A] rac-2-Methyl-2-{2-methyl-4-[1-methyl-5-(4-trifluoromethoxy-phenyl)-pent-4-ynyloxy]-phenoxy}-propionic acid ethyl ester In analogy to the procedure described in example 24A], rac-6-(4-trifluoromethoxy-phenyl)-hex-5-yn-2-ol (example 31E]) and 2-(4-hydroxy-2-methyl-phenoxy)-2-methyl-propionic acid ethyl ester (described in WO 02/092590) yielded the title compound as yellow oil.

MS: 478.2 $(M)^+$.

B] rac-2-Methyl-2-{2-methyl-4-[1-methyl-5-(4-trifluoromethoxy-phenyl)-pent-4-ynyloxy]-phenoxy}-propionic acid In analogy to the procedure described in example 1E], saponification of rac-2-methyl-2-{2-methyl-4-[1-methyl-5-(4-trifluoromethoxy-phenyl)-pent-4-ynyloxy]-phenoxy}-propionic acid ethyl ester, followed by purification described in example 26A] yielded the title compound as yellow oil.

MS: 449.2 $(M-H)^-$.

rac-6-(4-trifluoromethoxy-phenyl)-hex-5-yn-2-ol used in 31A] was prepared as follows:

C] 5-(4-Trifluoromethoxy-phenyl)-pent-4-ynoic acid methoxy-methyl-amide

A solution of 1.00 g (3.87 mmol) of 5-(4-trifluoromethoxy-phenyl)-pent-4-ynoic acid (example 29D]) in 50 ml $CH_2Cl_2$ was treated with 0.45 g (4.65 mmol) N,O-dimethylhydroxylamine hydrochloride, 0.55 ml (5.03 mmol) N-methylmorpholine and at 0° C. with 0.97 g (5.03 mmol) N-(3-dimethylaminopropyl)-N'-ethylcarbodiimide hydrochloride (EDCI). The reaction was naturally warmed to ambient temperature over night and partitioned between aqueous 10% $KHSO_4$/ether (three times). The organic phases were washed with aqueous saturated $NaHCO_3$, 10% NaCl and dried ($Na_2SO_4$) to give 1.165 g of the title compound as brown oil.

MS: 302.1 $(M+H)^+$.

D] 6-(4-Trifluoromethoxy-phenyl)-hex-5-yn-2-one

A cooled solution (0° C.) of 1.11 ml (3 M in ether, 3.32 mmol) of methyl magnesium bromide in 4 ml ether was dropped a solution of 0.77 g (2.56 mmol) 5-(4-trifluoromethoxy-phenyl)-pent-4-ynoic acid methoxy-methyl-amide in 4 ml ether. The reaction mixture was stirred 3 h at this temperature, diluted in ether and washed with aqueous, saturated $NH_4Cl$ solution, aqueous 10% $KHSO_4$ and 10% NaCl solution. The water phases were extracted with ether (two times), the organic phase was dried ($Na_2SO_4$) and evaporated to give 0.68 g of the title compound as yellow oil.

MS: 256.1 $(MH)^+$.

E] rac-6-(4-Trifluoromethoxy-phenyl)-hex-5-yn-2-ol

Within 15 min was dropped 1.46 ml (1.2 M in toluene, 1.75 mmol) of DIBAL-H to a dry ice cooled (−30° C.) solution of 0.23 g (0.88 mmol) 6-(4-trifluoromethoxy-phenyl)-hex-5-yn-2-one in 4 ml of THF. The reaction was warmed up (0° C. for 1 h 10 min) and neutralized with aqueous 10% $KHSO_4$ solution. The mixture was extracted with ether (three times), the organic phases were washed with a aqueous 10% NaCl solution, dried (Na$_2$SO$_4$) and evaporated to give 0.24 g of the title compound as light brown oil.

MS: 258.1 (M)$^+$.

Example 32

2-{3-Fluoro-4-[5-(4-trifluoromethoxy-phenyl)-pent-4-ynyloxy]-phenoxy}-2-methyl-propionic acid

A] 2-{3-Fluoro-4-[5-(4-trifluoromethoxy-phenyl)-pent-4-ynyloxy]-phenoxy}-2-methyl-propionic acid ethyl ester In analogy to the procedure described in example 20A], 2-(3-fluoro-4-hydroxy-phenoxy)-2-methyl-propionic acid ethyl ester (example 32E]) and methanesulfonic acid 5-(4-trifluoromethoxy-phenyl)-pent-4-ynyl ester (example 1G]) yielded the title compound as brown oil.

MS: 468.2 (M)$^+$.

B] 2-{3-Fluoro-4-[5-(4-trifluoromethoxy-phenyl)-pent-4-ynyloxy]-phenoxy}-2-methyl-propionic acid In analogy to the procedure described in example 1E], 2-{3-fluoro-4-[5-(4-trifluoromethoxy-phenyl)-pent-4-ynyloxy]-phenoxy}-2-methyl-propionic acid ethyl ester was hydrolyzed to give after purification as described in example 26A] the title compound as yellow solid, mp. 65.5-68.5° C.

MS: 439.1 (M−H)$^-$.

2-(3-Fluoro-4-hydroxy-phenoxy)-2-methyl-propionic acid ethyl ester used in 32A] was prepared as follows:

C] 2-(4-Acetyl-3-fluoro-phenoxy)-2-methyl-propionic acid ethyl ester

A suspension of 12.0 g (77.9 mmol) of 2-fluoro-4-hydroxyacetophenone, 27.9 g (85.6 mmol) of cesium carbonate and 11.6 ml (77.9 mmol) of ethyl 2-bromo-2-methyl-propionate in 200 ml of DMF was heated at 50° C. for 3 days. Twice a day additional 12.7 g (38.9 mmol) of cesium carbonate and 5.8 ml (38.9 mmol) of ethyl 2-bromo-2-methyl-propionate were added (total of 2.5 equivalents). The mixture was neutralized with aqueous 10% KHSO$_4$ and extracted with ether (three times). The organic phases were washed with aqueous 10% KHSO$_4$, aqueous 10% NaCl solution, dried (Na$_2$SO$_4$) and evaporated. The crude product was purified by flash chromatography over silica gel with n-heptane/AcOEt 9:1 to 6:1, to give 16.7 g of the title compound as colorless oil.

MS: 268.2 (M)$^+$.

D] 2-(4-Acetoxy-3-fluoro-phenoxy)-2-methyl-propionic acid ethyl ester

A solution of 3.0 g (11.2 mmol) of 2-(4-acetyl-3-fluoro-phenoxy)-2-methyl-propionic acid ethyl ester in 30 ml dichloromethane was treated with 4.1 g (70%, 16.8 mmol) of 3-chloro perbenzoic acid. The reaction was stirred at RT. After 1 day additional 1.2 g (70%, 4.7 mmol), after 2 days 0.8 g (70%, 3.1 mmol) and after 3 days 0.6 g (70%, 2.3 mmol) of 3-chloro perbenzoic acid were added. The mixture was poured on ice/aqueous 10% disodium pyrosulfite solution and extracted with ether (three times). The organic phases were washed with aqueous 10% NaHCO$_3$, aqueous saturated NH$_4$Cl, aqueous 10% NaCl and dried over sodium sulfate to give 3.2 g of the title compound as light yellow oil.

MS: 302.2 (M+NH$_4$)$^+$.

E] 2-(3-Fluoro-4-hydroxy-phenoxy)-2-methyl-propionic acid ethyl ester

A solution of 3.10 g (10.9 mmol) of 2-(4-acetoxy-3-fluoro-phenoxy)-2-methyl-propionic acid ethyl ester in 30 ml ethanol was treated at 0° C. with 2.26 g (16.4 mmol) of K$_2$CO$_3$. The mixture was stirred for 1 day at RT, then neutralized with aqueous 10% KHSO$_4$ and extracted with ether (three times). The organic phases were washed with aqueous 10% KHSO$_4$, aqueous 10% NaCl and dried over sodium sulfate. The crude product was purified by flash chromatography over silica gel with heptane/AcOEt 97.5:2.5 to 4:1, to give 2.48 g of the title compound as colorless crystals.

MS: 242.3 (M)$^+$.

Example 33

2-{3-Fluoro-2-methyl-4-[5-(4-trifluoromethoxy-phenyl)-pent-4-ynyloxy]-phenoxy}-2-methyl-propionic acid

A] 2-{3-Fluoro-2-methyl-4-[5-(4-trifluoromethoxy-phenyl)-pent-4-ynyloxy]-phenoxy}-2-methyl-propionic acid ethyl ester In analogy to the procedure described in example 20A], 2-(3-fluoro-4-hydroxy-2-methyl-phenoxy)-2-methyl-propionic acid ethyl ester (example 33H]) and methanesulfonic acid 5-(4-trifluoromethoxy-phenyl)-pent-4-ynyl ester (example 1G]) yielded the title compound as light yellow viscous oil.

MS: 482.2 (M)$^+$.

B] 2-{3-Fluoro-2-methyl-4-[5-(4-trifluoromethoxy-phenyl)-pent-4-ynyloxy]-phenoxy}-2-methyl-propionic acid In analogy to the procedure described in example 1E), 2-{3-fluoro-2-methyl-4-[5-(4-trifluoromethoxy-phenyl)-pent-4-ynyloxy]-phenoxy}-2-methyl-propionic acid ethyl ester was hydrolyzed to give the title compound as white powder, mp. 116-118° C.

MS: 453.2 (M−H)$^-$.

2-(3-Fluoro-4-hydroxy-2-methyl-phenoxy)-2-methyl-propionic acid ethyl ester used in 33A] was prepared as follows:

C] 2-(2-Fluoro-4-methoxy-phenyl)-2-methyl-[1,3]dioxolane

A solution of 5.00 g (30.00 mmol) 2-fluoro-4-methoxy-acetophenone, 1.11 ml (33.00 mmol) ethylene glycol and 0.28 g (1.49 mmol) p-toluene sulfonic acid hydrate in 50 ml toluene was refluxed in a Dean-Stark apparatus for 2.5 days. After 0.5 and 1.5 days additional 1.11 ml (33.00 mmol) ethylene glycol and 0.28 g (1.49 mmol) p-toluene sulfonic acid hydrate were added. After cooling, the reaction was diluted in ether and washed with aqueous saturated NaHCO$_3$ (two times) and aqueous 10% NaCl solution. The water phases were extracted with ether, the organic phase was dried (Na$_2$SO$_4$) and evaporated. The crude product was purified by flash chromatography (SiO$_2$; n-heptane/AcOEt=95:5) to give 4.90 g of the title compound as brown liquid (with ca 10% of starting material, seen in $^1$H-NMR).

MS: 212.2 (M)$^+$.

D] 1-(2-Fluoro-4-methoxy-3-methyl-phenyl)-ethanone 17.69 ml (1.6 M in n-hexane, 28.30 mmol) n-BuLi were added slowly to a cooled solution (−78° C.) of the above prepared 4.29 g (20.21 mmol) 2-(2-fluoro-4-methoxy-phenyl)-2-methyl-[1,3]-dioxolane in 100 ml THF. The reaction was stirred for 30 min at this temperature. 5.03 ml (80.86 mmol) of iodomethane were then added over 20 min and after 6 h at −78° C. the reaction was stopped with 3.24 ml (56.60 mmol) of acetic acid in 5 ml ether. The reaction mixture was taken up in ether and washed with aqueous 10%

KHSO₄ solution and aqueous 10% NaCl solution. The water phases were extracted with ether (two times). The organic phase was dried (Na₂SO₄) and evaporated. The crude product was dissolved in 30 ml dioxane and treated slowly with 6.74 ml of aqueous 6M HCl. After 2 h, the reaction was taken up in ether and washed with aqueous 10% NaCl solution (two times). The water phases were extracted with ether (two times). The organic phase was dried (Na₂SO₄), evaporated and purified by flash chromatography (SiO₂; n-heptane/CH₂Cl₂=4:1) to give 1.60 g of the title compound.
MS: 182.1 (M)⁺.

E] 1-(2-Fluoro-4-hydroxy-3-methyl-phenyl)-ethanone

A solution of 1.09 g (5.96 mmol) 1-(2-fluoro-4-methoxy-3-methyl-phenyl)-ethanone was dissolved in 12 ml acetic acid and 6 ml 62% aqueous HBr. The reaction mixture was stirred 2 h at room temperature and heated to 120° C. for 6 h, cooled, diluted with ether and neutralized carefully with aqueous saturated NaHCO₃ (pH=8). Extraction of the water phase with ether (two times), washing with aqueous 10% NaCl, drying (Na₂SO₄) and evaporation gave 0.78 g of the crude product as a dark red gum.
MS: 167.3 (M−H)⁻.

F] 2-(4-Acetyl-3-fluoro-2-methyl-phenoxy)-2-methyl-propionic acid ethyl ester

A suspension of 0.21 g (0.62 mmol) of crude 1-(2-fluoro-4-hydroxy-3-methyl-phenyl)-ethanone, 0.45 g (1.37 mmol) of cesium carbonate and 0.24 ml (1.25 mmol) of ethyl 2-bromo-2-methylpropionate in 5 ml of DMF was heated at 50° C. for 7 h. Additional 0.10 g (0.31 mmol) of cesium carbonate and 0.06 ml (0.31 mmol) of ethyl 2-bromo-2-methylpropionate were added and stirred at 50° C. for 11 h. The mixture was neutralized with aqueous 10% KHSO₄ and extracted with ether (three times). The organic phases were washed with aqueous 10% KHSO₄, aqueous 10% NaCl solution, dried (Na₂SO₄) and evaporated. The crude product was purified by flash chromatography over silica gel with n-heptane/AcOEt 95:5 to give 0.048 g of the title compound as yellow liquid.
MS: 282.1 (M)⁺.

G] 2-(4-Acetoxy-3-fluoro-2-methyl-phenoxy)-2-methyl-propionic acid ethyl ester

In analogy to the procedure described in example 32D], 2-(4-acetyl-3-fluoro-2-methyl-phenoxy)-2-methyl-propionic acid ethyl ester was oxidized with a total of 4.5 equivalent of 3-chloro perbenzoic acid during 6 day to give the title compound as orange semisolid residue.
MS: 142.1 (M)⁺.

H] 2-(3-Fluoro-4-hydroxy-2-methyl-phenoxy)-2-methyl-propionic acid ethyl ester

In analogy to the procedure described in example 32E], 2-(4-acetoxy-3-fluoro-2-methyl-phenoxy)-2-methyl-propionic acid ethyl ester was hydrolyzed during 88 h to give the title compound as brown semisolid residue.
MS: 256.2 (M)⁺.

Example 34

2-Methyl-2-(2-methyl-4-{1-[3-(4-trifluoromethoxy-phenyl)-prop-2-ynyl]-cyclobutylmethoxy}-phenoxy)-propionic acid A] 2-Methyl-2-(2-methyl-4-{1-[3-(4-trifluoromethoxy-phenyl)-prop-2-ynyl]-cyclobutylmethoxyl-phenoxy)-propionic acid ethyl ester A suspension of 0.100 g (0.25 mmol) 1-[3-(1-iodomethyl-cyclobutyl)-prop-1-ynyl]-4-trifluoromethoxy-benzene (example 34G]), 0.060 g (0.25 mmol) 2-(4-hydroxy-2-methyl-phenoxy)-2-methyl-propionic acid ethyl ester (described in WO 02/092590) and 0.099 g (0.30 mmol) Cs₂CO₃ in 2 ml acetonitrile was stirred for 16 h at room temperature and 7 h at reflux temperature. 0.041 g (0.15 mmol) Cs₂CO₃ was added and stirred at reflux temperature for 12 h. After filtration, the residue was dissolved in dichloromethane, dried (Na₂SO₄), filtered and evaporated. Purification by flash chromatography (SiO₂, n-heptane and then n-heptane/EtOAc 5%) yielded 0.139 g of the title compound as light yellow oil.
MS: 504.3 (M)⁺.

B] 2-Methyl-2-(2-methyl-4-{1-[3-(4-trifluoromethoxy-phenyl)-prop-2-ynyl]-cyclobutylmethoxy}-phenoxy)-propionic acid In analogy to the procedure described in example 1E], saponification of 2-methyl-2-(2-methyl-4-{1-[3-(4-trifluoromethoxy-phenyl)-prop-2-ynyl]-cyclobutylmethoxy}-phenoxy)-propionic acid ethyl ester, followed by purification described in example 26A] yielded the title compound as light yellow oil.
MS: 475.1 (M−H)⁻.

1-[3-(1-Iodomethyl-cyclobutyl)-prop-1-ynyl]-4-trifluoromethoxy-benzene used in 34A] was prepared as follows:

C] 1-Prop-2-ynyl-cyclobutanecarboxylic acid ethyl ester

In analogy to the procedure described in example 24C], reaction of ethyl cyclobutanecarboxylate and propargyl bromide gave the title compound as brown liquid.
MS: 166.1 (M)⁺.

D] 1-[3-(4-Trifluoromethoxy-phenyl)-prop-2-ynyl]-cyclobutanecarboxylic acid ethyl ester In analogy to the procedure described in example 24E], reaction of 1-prop-2-ynyl-cyclobutanecarboxylic acid ethyl ester and 1-iodo-4-trifluoromethoxybenzene gave the title compound as yellow oil.
MS: 326.2 (M)⁺.

E]{1-[3-(4-Trifluoromethoxy-phenyl)-prop-2-ynyl]-cyclobutyl}-methanol

In analogy to the procedure described in example 31E], reduction of 1-[3-(4-trifluoromethoxy-phenyl)-prop-2-ynyl]-cyclobutanecarboxylic acid ethyl ester with 3 equivalent of DIBAL-H (1.2 M solution in toluene) gave the title compound as yellow oil.
MS: 284.1 (M)⁺.

F] Methanesulfonic acid 1-[3-(4-trifluoromethoxy-phenyl)-prop-2-ynyl]-cyclobutylmethyl ester In analogy to the procedure described in example 1G], {1-[3-(4-trifluoromethoxy-phenyl)-prop-2-ynyl]-cyclobutyl}-methanol and methanesulfonyl chloride gave the title compound as yellow oil.
MS: 362.1 (M)⁺.

G] 1-[3-(1-Iodomethyl-cyclobutyl)-prop-1-ynyl]-4-trifluoromethoxy-benzene

To a solution of 0.78 g (2.15 mmol) methanesulfonic acid 1-[3-(4-trifluoromethoxy-phenyl)-prop-2-ynyl]-cyclobutyl-methyl ester in 30 ml 2-butanone was added 0.65 g (4.30 mmol) NaI. The mixture was heated for 9 h at 90° C. The solvent was evaporated and the residue suspended in dichloromethane, ether was added and the suspension was filtrated. Evaporation of the organic phase gave 0.74 g of the title compound as dark brown oil.
MS: 394.1 (M)⁺.

Example 35

2-Methyl-2-(2-methyl-4-{1-[3-(4-trifluoromethoxy-phenyl)-prop-2-ynyl]-cyclopropylmethoxy]-phenoxy}-propionic acid A] 2-Methyl-2-(2-methyl-4-{1-[3-(4-trifluoromethoxy-phenyl)-prop-2-ynyl]-cyclopropylmethoxy}-phenoxy)-propionic acid ethyl ester In analogy to the procedure described in example 24E), reaction of 2-methyl-2-[2-methyl-4-(1-prop-2-ynyl-cyclopropylmethoxy)-phenoxy]-propionic acid ethyl ester (example 35I]) and 1-iodo-4-trifluoromethoxybenzene gave the title compound as light yellow oil.

MS: 490.2 (M)+.

B] 2-Methyl-2-(2-methyl-4-[1-[3-(4-trifluoromethoxy-phenyl)-prop-2-ynyl]-cyclopropylmethoxy}-phenoxy)-propionic acid In analogy to the procedure described in example 1E], saponification of 2-methyl-2-(2-methyl-4-{1-[3-(4-trifluoromethoxy-phenyl)-prop-2-ynyl]-cyclopropylmethoxy}-phenoxy)-propionic acid ethyl ester yielded the title compound as light yellow oil.

MS: 461.1 (M–H)−.

2-Methyl-2-[2-methyl-4-(1-prop-2-ynyl-cyclopropylmethoxy)-phenoxy]-propionic acid ethyl ester used in 35A] was prepared as follows:

C] Cyclopropanecarboxylic acid tert-butyl ester

The esterification was performed following conditions described in Wright, Stephen W.; Hageman, David L.; Wright, Ann S.; Mc Clure, Lester D., *Tetrahedron Letters* 1997, 38(42), 7345-7348. 8.04 ml (150 mmol) concentrated sulfuric acid was added to a vigorously stirred suspension of 72.22 g (600 mmol) $MgSO_4$ in 450 ml $CH_2Cl_2$. The mixture was stirred for 20 min, after which 11.90 ml (150 mmol) of cyclopropanecarboxylic acid was added. 55.59 ml (750 mmol) of tert-butanol was added last. The mixture was sealed tightly and stirred for 18 h at room temperature. The reaction was quenched with aqueous saturated $NaHCO_3$ and stirred until all $MgSO_4$ had dissolved. The aqueous phase was extracted with ether (two times). The organic phases were washed with water (5×), aqueous saturated NaCl solution and dried ($Na_2SO_4$) to give 10.38 g of the title compound as volatile, light yellow liquid.

D] 1-(3-Trimethylsilanyl-prop-2-ynyl)-cyclopropanecarboxylic acid tert-butyl ester A solution of 14.0 ml (2.0 M in THF/n-heptane/ethylbenzene, 28 mmol) LDA in 100 ml THF was treated during 15 min at −78° C. with 2.84 g (20 mmol) cyclopropanecarboxylic acid tert-butyl ester in 20 ml THF. After 6 h at −78° C., a solution of 3-(trimethylsilyl) propargyl bromide and 29 ml DMPU in 40 ml THF was added during 20 min. Over night, the solution was naturally warmed to room temperature, poured on ice/aqueous saturated $NH_4Cl$ solution and extracted with ether (three times). The organic phases were washed with aqueous 10% $KHSO_4$, water (5×), aqueous 10% NaCl and dried ($Na_2SO_4$) to give 5.59 g of the title compound as volatile dark brown liquid.

MS: 253.4(M+H)+.

E] [1-(3-Trimethylsilanyl-prop-2-ynyl)-cyclopropyl]-methanol

In analogy to the procedure described in example 24D], reduction of the crude 1-(3-trimethylsilanyl-prop-2-ynyl)-cyclopropane carboxylic acid tert-butyl ester with LAH (1 M in THF) gave after naturally warming up to ambient temperature (during 2.75 h) the title compound as yellow oil.

GC/MS: 182 (M)+.

F] Methanesulfonic acid 1-(3-trimethylsilanyl-prop-2-ynyl)-cyclopropylmethyl ester In analogy to the procedure described in example 1G], [1-(3-trimethylsilanyl-prop-2-ynyl)-cyclopropyl]-methanol and methanesulfonyl chloride gave the title compound as yellow oil.

MS: 278.3 (M+$NH_4$)+.

G] [3-(1-Iodomethyl-cyclopropyl)-prop-1-ynyl]-trimethylsilane

In analogy to the procedure described in example 34G], methanesulfonic acid 1-(3-trimethylsilanyl-prop-2-ynyl)-cyclopropylmethyl ester and NaI gave after 30 min at reflux temperature the title compound as orange oil.

GC/MS: 293 (M+H)+.

H] 2-Methyl-2-{2-methyl-4-[1-(3-trimethylsilanyl-prop-2-ynyl)-cyclopropylmethoxy]-phenoxy}-propionic acid ethyl ester In analogy to the procedure described in example 20A], [3-(1-iodomethyl-cyclopropyl)-prop-1-ynyl]-trimethylsilane and 2-(4-hydroxy-2-methyl-phenoxy)-2-methyl-propionic acid ethyl ester (described in WO 02/092590) gave after 18 h at room temperature the title compound as light yellow oil.

MS: 402.3 (M)+.

I] 2-Methyl-2-[2-methyl-4-(1-prop-2-ynyl-cyclopropylmethoxy)-phenoxy]-propionic acid ethyl ester A solution of 0.201 (0.50 mmol) 2-methyl-2-{2-methyl-4-[1-(3-trimethylsilanyl-prop-2-ynyl)-cyclopropylmethoxy]-phenoxy}-propionic acid ethyl ester in 5 ml THF were treated at 0° C. with 0.55 ml (1 M solution in THF, 0.55 mmol) of n-$Bu_4NF$ and stirred for 1.5 h at this temperature. The reaction mixture was then diluted with water and extracted with ether (three times). The organic layers were washed with water, dried ($Na_2SO_4$) and evaporated to give 0.152 g of the title compound as light yellow oil.

MS: 330.2 (M)+.

Example 36

2-{5-Methoxy-2-methyl-4-[5-(4-trifluoromethoxy-phenyl)-pent-4-ynyloxy]-phenoxy}-2-methyl-propionic acid A] 1-(4-Hydroxy-2-methoxy-5-methyl-phenyl)-ethanone 1.16 ml (16 mmol) Acetylchloride were added within 5 min to a ice cooled suspension of 2.4 g (16.4 mmol) $AlCl_3$ in 5 ml 1,2-dichloroethane under an argon atmosphere. A solution of 1.13 g (8.2 mmol) 5-methoxy-2-methyl-phenol (PCT Int. Appl. WO 2003/084916 A2) in 2.4 ml 1,2-dichloroethane was added within 5 min. The mixture was naturally warmed to ambient temperature, poured after 4 h onto ice water and extracted twice with dichloromethane. The combined extracts were washed with ice water/0.5 M NaOH solution 1/1 and brine and dried over sodium sulfate. Removal of the solvent under reduced pressure gave a yellow oil which was dissolved in a mixture of 3.5 ml methanol, 7 ml THF and 7 ml 1 M LiOH solution. The solution was stirred for 30 min at ambient temperature and the solvent was partially removed under reduced pressure. Ice water/1 M HCl solution 1/1 was added and the solution was extracted twice with ethyl acetate. The combined extracts were washed with brine and dried over sodium sulfate. Evaporation of the solvent left a yellow solid which was crystallized from dichloromethane/methanol/heptane to yield 441 mg (2.45 mmol, 30%) of the title compound as colorless crystals.

MS: 179.4 (M–H)⁻.

B] 2-(4-Acetyl-5-methoxy-2-methyl-phenoxy)-2-methyl-propionic acid ethyl ester

A suspension of 416 mg (2.3 mmol) 1-(4-hydroxy-2-methoxy-5-methyl-phenyl)-ethanone, 0.69 ml (4.6 mmol) 2-bromo-2-methyl-propionic acid ethyl ester, 1.58 g (4.9 mmol) cesium carbonate and a trace of potassium iodide in 25 ml acetonitrile was heated under reflux conditions for 14 h. The mixture was poured onto 1 M HCl solution/ice water 1/1 and extracted two times with ethyl acetate. The combined extracts were washed with brine/ice water and dried over sodium sulfate. Removal of the solvent under reduced pressure gave a yellow oil which was purified by column chromatography (silica gel, heptane/AcOEt) to give 450 mg (1.5 mmol, 66%) of the title compound as colorless oil.

MS: 295.5 (M+H)⁺.

C] 2-(4-Acetoxy-5-methoxy-2-methyl-phenoxy)-2-methyl-propionic acid ethyl ester

A solution of 531 mg (1.8 mmol) 2-(4-acetyl-5-methoxy-2-methyl-phenoxy)-2-methyl-propionic acid ethyl ester, 545 mg (3.2 mmol) 3-chloroperbenzoic acid and 34 mg (0.2 mmol) 4-toluenesulfonic acid in 24 ml dichloromethane was heated under reflux conditions for 72 h. The mixture was cooled to room temperature and washed two times with ice water/sodium iodide solution and two times with ice water/ aqueous NaHSO₃ solution. The organic layer was dried over sodium sulfate, the solvent was removed under reduced pressure and the resulting brown solid was purified by column chromatography (silica gel, heptane/AcOEt) to give 235 mg (0.8 mmol, 42%) of the title compound as yellow oil.

MS: 311.3 (M+H)⁺.

D] 2-(4-Hydroxy-5-methoxy-2-methyl-phenoxy)-2-methyl-propionic acid methyl ester A freshly prepared solution of 91 mg (4 mmol) sodium in 5.4 ml methanol was added within 5 min to an ice cooled solution of 235 mg (0.8 mmol) 2-(4-acetoxy-5-methoxy-2-methyl-phenoxy)-2-methyl-propionic acid ethyl ester in 5.4 ml methanol. The solution was naturally warmed to ambient temperature and after 5 h the solvent was removed under reduced pressure. Ice water/1 M HCl 1/1 was added and the mixture was extracted two times with dichloromethane. The combined extracts were dried over sodium sulfate and the solvent was removed under reduced pressure to yield 153 mg (0.6 mmol, 76%) of the title compound as brown oil which was used in the next step without further purification.

MS: 254.2 (M)⁺.

E] 2-{5-Methoxy-2-methyl-4-[5-(4-trifluoromethoxy-phenyl)-pent-4-ynyloxy]-phenoxy}-2-methyl-propionic acid methyl ester In analogy to the procedure described in example 1D], 2-(4-hydroxy-5-methoxy-2-methyl-phenoxy)-2-methyl-propionic acid methyl ester was reacted with methanesulfonic acid 5-(4-trifluoromethoxy-phenyl)-pent-4-ynyl ester (example 1G]) in the presence of NaI and Cs₂CO₃ in acetonitrile under reflux conditions for 4 h, to give 2-{5-methoxy-2-methyl-4-[5-(4-trifluoromethoxy-phenyl)-pent-4-ynyloxy]-phenoxy}-2-methyl-propionic acid methyl ester as colorless oil.

MS: 481.0 (M+H)⁺.

F] 2-{5-Methoxy-2-methyl-4-[5-(4-trifluoromethoxy-phenyl)-pent-4-ynyloxyl-phenoxy}-2-methyl-propionic acid In analogy to the procedure described in example 1E], saponification of 2-{5-methoxy-2-methyl-4-[5-(4-trifluoromethoxy-phenyl)-pent-4-ynyloxy]-phenoxy}-2-methyl-propionic acid methyl ester yielded the title compound as brown oil.

MS: 467.4 (M+H)⁺.

Example 37

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesium stearate and compressed to yield kernels of 120 or 350 mg respectively. The kernels are lacquered with an aqueous solution /suspension of the above mentioned film coat.

Example 38

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example 39

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example 40

Soft gelatin capsules containing the following ingredients can be manufactured in a conventional manner:

| Capsule contents | |
| --- | --- |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example 41

Sachets containing the following ingredients can be manufactured in a conventional manner:

| | |
| --- | --- |
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Example 42

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257: 112-119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM $MgCl_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiom-ethylsulfanyl]-phenoxy}-acetic acid, was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resuspended in 50 μl of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using OptiPlates (Packard). Dose response curves were done in triplicates within a range of concentration from $10^{-10}$ M to $10^{-4}$ M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARα-LBD fusion protein was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resolved in 50 μl of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 μl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% O2:5% $CO_2$ atmosphere. Cells were seeded in 6 well plates at a density of $10^5$ cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit $IC_{50}$ values of 0.5 nM to 10 μM, preferably 1 nM to 250 nM for PPARδ and $IC_{50}$ values of 1 nM to 10 μM, preferably 5 nM to 500 nM for PPARα. Compounds, in which $R^1$ is not hydrogen are converted in vivo to compounds in which $R^1$ is hydrogen. The following table shows measured values for some selected compounds of the present invention.

|  | PPARα $IC_{50}$ (μmol/l) | PPARγ $IC_{50}$ (μmol/l) | PPARδ $IC_{50}$ (μmol/l) |
| --- | --- | --- | --- |
| Example 4 | 0.014 | >10 | 0.039 |
| Example 13 | 0.021 | >10 | 0.120 |
| Example 17 | 0.018 | >10 | 0.203 |

It is to be understood that the invention is not limited to the particular embodiments of the invention described above, as variations of the particular embodiments may be made and still fall within the scope of the appended claims.

What is claimed is:

1. A compound of the formula I

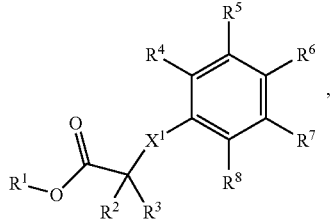

wherein:
$X^1$ is O or S;
$R^1$ is hydrogen or $C_{1-7}$-alkyl;
$R^2$ is hydrogen or $C_{1-7}$-alkyl,
$R^3$ is hydrogen or $C_{1-7}$-alkyl;
$R^4$ and $R^8$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;
$R^5$, $R^6$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, fluoro-$C_{1-7}$-alkoxy, cyano-$C_{1-7}$-alkyl and cyano;
and one of $R^5$, $R^6$ and $R^7$ is

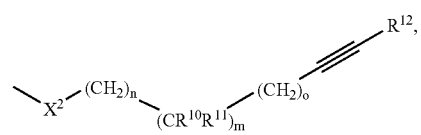

wherein
$X^2$ is selected from the group consisting of S, O, $NR^9$, $(CH_2)_pNR^9CO$ and $(CH_2)_pCONR^9$;
$R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl;
$R^{10}$ is selected from the group consisting of $C_{1-7}$-alkyl, $C_{3-7}$-cycloalkyl, fluoro-$C_{1-7}$-alkyl and $C_{1-7}$-alkoxy-$C_{1-7}$-alkyl;
$R^{11}$ is selected from the group consisting of hydrogen, $C_{1-7}$-alkyl, and $C_{1-7}$-alkoxy-$C_{1-7}$-alkyl;
or $R^{10}$ and $R^{11}$ together with the carbon atom they are attached to form a $C_{3-6}$-cycloalkyl ring;
m, o, p is 0, 1 or 2; n is 0, 1, 2 or 3;
and the sum of m, n and o is 1 to 5;
$R^{12}$ is unsubstituted phenyl, phenyl substituted with one to three groups selected from the group consisting of $C_{1-7}$-alkyl, $C_{1-7}$-alkoxy, halogen, fluoro-$C_{1-7}$-alkyl, fluoro-$C_{1-7}$-alkoxy and cyano, unsubstituted pyridyl or pyridyl substituted with one to three groups selected from the group consisting of $C_{1-7}$-alkyl, $C_{1-7}$-alkoxy, halogen, fluoro-$C_{1-7}$-alkyl, fluoro-$C_{1-7}$-alkoxy and cyano;
and pharmaceutically acceptable salts or esters thereof.

2. The compound according to claim 1, having the formula I-A:

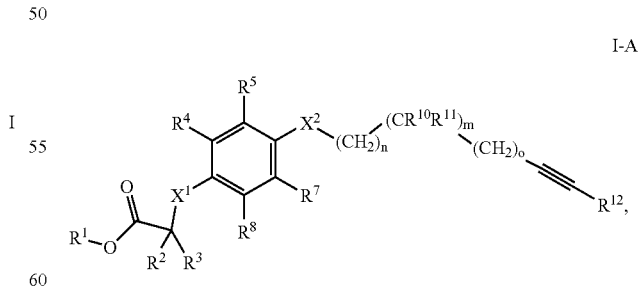

wherein:
$X^1$, $X^2$, $R^1$ to $R^4$, $R^8$, $R^{10}$ to $R^{12}$, m, n and o are as defined in claim 1;
$R^5$ and $R^7$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{1-7}$- alkenyl, $C_{1-7}$-alkinyl, fluoro-$C_{1-7}$-alkyl, fluoro-$C_{1-7}$-alkoxy, cyano-$C_{1-7}$-alkyl and cyano; and pharmaceutically acceptable salts or esters thereof.

3. The compound according to claim 2, wherein at least one of $R^4$, $R^5$, $R^7$ and $R^8$ is selected from the group consisting of $C_{1-7}$-alkyl, $C_{1-7}$-alkoxy and halogen.

4. The compound according to claim 3, wherein $R^4$ is selected from the group consisting of $C_{1-7}$-alkyl, halogen and $C_{1-7}$-alkoxy.

5. The compound according to claim 1, wherein $R^1$ is hydrogen.

6. The compound according to claim 1, wherein $X^1$ is O.

7. The compound according to claim 1, wherein $R^2$ and $R^3$ are $C_{1-7}$-alkyl.

8. The compound according to claim 1, wherein $R^2$ and $R^3$ are hydrogen.

9. The compound according to claim 1, wherein $X^2$ is selected from the group consisting of S, O and $NR^9$, and wherein $R^9$ selected from the group consisting of hydrogen, $C_{1-7}$-alkyl, $C_{3-7}$-cycloalkyl, fluoro-$C_{1-7}$-alkyl, hydroxy-$C2$-$7$-alkyl and $C_{1-7}$-alkoxy-$C_{2-7}$-alkyl.

10. The compound according to claim 9, wherein $X^2$ is S or O.

11. The compound according to claim 9, wherein $X^2$ is S.

12. The compound according to claim 9, wherein $X^2$ is O.

13. The compound according to claim 1, wherein m is 0.

14. The compound according to claim 9, wherein m is 0 and the sum of n and o is 1, 2 or 3.

15. The compound according to claim 14, wherein the sum of n and o is 2 or 3.

16. The compound according to claim 1, wherein $X^2$ is $(CH_2)_pNR_9CO$ or $(CH_2)_pCONR^9$, $R^9$ is selected from the group consisting of hydrogen, $C_{1-7}$-alkyl, $C_{3-7}$-cycloalkyl, fluoro-$C_{1-7}$-alkyl, hydroxy-$C_{2-7}$-alkyl and $C_{1-7}$-alkoxy-$C_{2-7}$-alkyl, and the integer p is 0, 1 or 2.

17. The compound according to claim 1, wherein $R^{12}$ is phenyl substituted with halogen, $C_{1-7}$-alkoxy, fluoro-$C_{1-7}$-alkyl or fluoro-$C_{1-7}$-alkoxy.

18. The compound according to claim 1, wherein $R^{12}$ is pyridyl substituted by fluoro-$C_{1-7}$-alkyl or fluoro-$C_{1-7}$-alkoxy.

19. The compound according to claim 1, selected from the group consisting of:

2-methyl-2-{2-methyl-4-[5-(4-trifluoromethoxy-phenyl)-pent-4-ynylsulfanyl]-phenoxy}-propionic acid, 2-methyl-2-{2-methyl-4-[4-(4-trifluoromethyl-phenyl)-but-3-ynylsulfanyl]-phenoxy}-propionic acid, 2-methyl-2-{2-methyl-4-[5-(3-trifluoromethoxy-phenyl)-pent-4-ynylsulfanyl]-phenoxy}-propionic acid, {2-methyl-4-[5-(4-trifluoromethoxy-phenyl)-pent-4-ynylsulfanyl]-phenoxy}-acetic acid, {2-methyl-4-[3-(4-trifluoromethyl-phenyl)-prop-2-ynylsulfanyl]-phenoxy}-acetic acid, {2-methyl-4-[3-(3-trifluoromethyl-phenyl)-prop-2-ynylsulfanyl]-phenoxy}-acetic acid, {2-methyl-4-[3-(2-trifluoromethyl-phenyl)-prop-2-ynylsulfanyl]-phenoxy}-acetic acid, {4-[3-(4-chloro-phenyl)-prop-2-ynylsulfanyl]-2-methyl-phenoxy}-acetic acid, {4-[3-(4-methoxy-phenyl)-prop-2-ynylsulfanyl]-2-methyl-phenoxy}-acetic acid,

[2-methyl-4-(3-phenyl-prop-2-ynylsulfanyl)-phenoxy]-acetic acid,

{4-[3-(4-fluoro-phenyl)-prop-2-ynylsulfanyl]-2-methyl-phenoxy}-acetic acid,

{2-methyl-4-[4-(4-trifluoromethyl-phenyl)-but-3 -ynyl-sulfanyl]-phenoxy}-acetic acid, 2-methyl-2-{2-methyl-4-[5-(4-trifluoromethoxy-phenyl)-pent-4-ynyloxy]-phenoxy}-propionic acid, 2-methyl-2-{2-methyl-4-[5-(4-trifluoromethyl-phenyl)-pent-4-ynyloxy]-phenoxy}-propionic acid, 2-{4-[5-(4-chloro-phenyl)-pent-4-ynyloxy]-2-methyl-phenoxy}-2-methyl-propionic acid, 2-methyl-2-{2-methyl-4-[4-(4-trifluoromethyl-phenyl)-but-3 -ynyloxy]-phenoxy}-propionic acid, 2-methyl-2-{2-methyl-4-[4-(4-trifluoromethoxy-phenyl)-but-3 -ynyloxy]-phenoxy}-propionic acid, 2-{4-[4-(4-chloro-phenyl)-but-3-ynyloxy]-2-methyl-phenoxy}-2-methyl-propionic acid, 2-methyl-2-{2-methyl-4-[5-(5-trifluoromethyl-pyridin-2-yl)-pent-4-ynyloxy]-phenoxy}-propionic acid, {2-methyl-4-[5-(4-trifluoromethoxy-phenyl)-pent-4-ynyloxy]-phenoxy}-acetic acid, 2-{2,5-dichloro-4-[5 -(4-trifluoromethoxy-phenyl)-pent-4-ynyloxy]-phenoxy}-2-methyl -propionic acid, 2-methyl-2-{2-methyl-4-[5-(3-trifluoromethoxy-phenyl)-pent-4-ynyloxy]-phenoxy}-propionic acid, 2-methyl-2-{2-methyl-4-[5-(3 -trifluoromethyl-phenyl)-pent-4-ynyloxy]-phenoxy}-propionic acid, 2-{4-[2,2-dimethyl-5-(4-trifluoromethoxy-phenyl)-pent-4-ynyloxy]-2-methyl-phenoxy}-2-methyl-propionic acid, 2-{4-[2,2-dimethyl-5-(4-trifluoromethoxy-phenyl)-pent-4-ynylsulfanyl]-2-methyl-phenoxy}-2-methyl-propionic acid, 2-{4-[5-(3-fluoro-phenyl)-pent-4-ynyloxy]-2-methyl-phenoxy}-2-methyl-propionic acid, 2-{4-[5-(4-chloro-3-fluoro-phenyl)-pent-4-ynyloxy}-2-methyl-phenoxy}-2-methyl-propionic acid, 2-methyl-2-{2-methyl-4-[5-(2-trifluoromethyl-pyrimidin-5-yl)-pent-4-ynyloxy]-phenoxy}-propionic acid, 2-methyl-2-(4-{[5-(4-trifluoromethoxy-phenyl)-pent-4-ynoylamino]-methyl}-phenoxy) -propionic acid, 2-methyl-2-[4-({methyl-[5-(4-trifluoromethoxy-phenyl)-pent-4-ynoyl]-amino}-methyl)-phenoxy]-propionic acid, rac-2-methyl-2-{2-methyl-4-[1-methyl-5-(4-trifluoromethoxy-phenyl)-pent-4-ynyloxy]-phenoxy}-propionic acid, 2-{3-fluoro-4-[5-(4-trifluoromethyl-phenyl)-pent-4-ynyloxy]-phenoxy}-2-methyl-propionic acid, 2-{3-fluoro-2-methyl-4-[5-(4-trifluoromethoxy-phenyl)-pent-4-ynyloxy]-phenoxy}-2-methyl propionic acid, 2-methyl-2-(2-methyl-4-{1-[3-(4-trifluoromethoxy-phenyl)-prop-2-ynyl]-cyclobutylmethoxy}-phenoxy)-propionic acid, 2-methyl-2-(2-methyl-4-{1-[3-(4-trifluoromethoxy-phenyl)-prop-2-ynyl]-cyclopropylmethoxy}-phenoxy)-propionic acid, and 2-{5-methoxy-2-methyl-4-[5-(4-trifluoromethoxy-phenyl)-pent-4-ynyloxy]-phenoxy}-2-methyl-propionic acid, and pharmaceutically acceptable salts or esters thereof.

20. The compound according to claim 1, selected from the group consisting of:

{2-methyl-4-[5-(4-trifluoromethoxy-phenyl)-pent-4-ynylsulfanyl]-phenoxy}-acetic acid, 2-methyl-2-{2-methyl-4-[5-(4-trifluoromethoxy-phenyl)-pent-4-ynyloxy]-phenoxy}-propionic acid, 2-methyl-2-{2-methyl-4-[4-(4-trifluoromethoxy-phenyl)-but-3-ynyloxy]-phenoxy}-propionic acid, 2-{2,5-dichloro-4-[5-(4-trifluoromethoxy-phenyl)-pent-4-ynyloxy]-phenoxy}-2-methyl -propionic acid, 2-{4-[2,2-dimethyl-5-(4-trifluoromethoxy-phenyl)-pent-4-ynylsulfanyl]-2-methyl-phenoxy}-2-methyl-propionic acid, and 2-methyl-2-(2-methyl-4-{1-[3-(4-trifluoromethoxy-phenyl)-prop-2-ynyl]-cyclobutylmethoxy}-phenoxy)-propionic acid, and pharmaceutically acceptable salts or esters thereof.

21. A process for the manufacture of a compound according to claim 1, comprising the steps of:

a) reacting a compound of formula

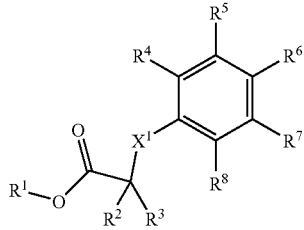

II wherein $R^1$ is $C_{1-7}$-alkyl, $X^1$ and $R^2$ to $R^8$ are as defined as in claim 1 and one of $R^5$, $R^6$ or $R^7$ is selected from —OH, —SH or —NHR$^9$, wherein $R^9$ is as defined in claim 1, with a compound of formula

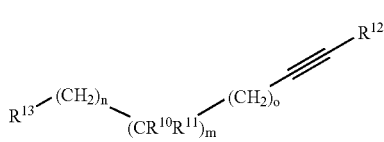

III wherein $R^{10}$, $R^{11}$, $R^{12}$, m, n and o are as defined in claim 1 and $R^{13}$ is —OH, —Cl, —Br, —I or another leaving group, to obtain a compound of formula

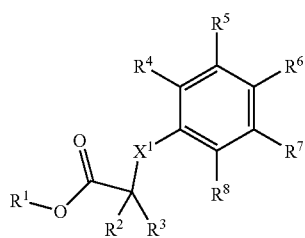

I-1 wherein one of $R^5$, $R^6$ and $R^7$ is

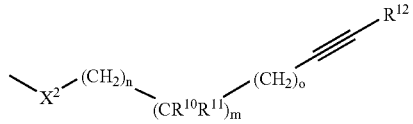

and wherein $X^2$ is O, S or —NR$^9$, $R^1$ is $C_{1-7}$-alkyl and $X^1$, $R^2$ to $R^{12}$ and m, n and o are as defined in claim 1, and optionally hydrolyzing the ester group to obtain a compound of formula I, wherein $R^1$ is hydrogen;

or, alternatively, b) reacting a compound of formula

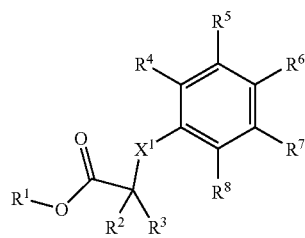

IV wherein $R^1$ is $C_{1-7}$-alkyl, $R^2$ to $R^8$ are as defined as in claim 1 and one of $R^5$, $R^6$ or $R^7$ is —(CH$_2$)$_p$—NHR$^9$, wherein $R^9$ and p are as defined in claim 1, with a compound of formula

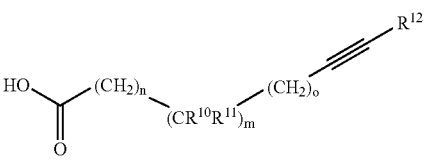

V wherein $R^{10}$, $R^{11}$, $R^{12}$, m, n and o are as defined in claim 1, to obtain a compound of formula

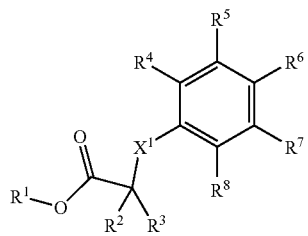

I-2 wherein one of $R^5$, $R^6$ and $R^7$ is

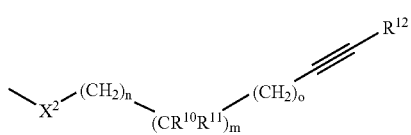

and wherein $X^2$ is —(CH$_2$)$_p$—NR$_9$CO—, $R^1$ is $C_{1-7}$-alkyl and $X^1$, $R^2$ to $R^{12}$ and m, n, o and p are as defined in claim 1, and optionally hydrolyzing the ester group to obtain a compound of formula I, wherein $R^1$ is hydrogen;

or, alternatively, c) reacting a compound of formula

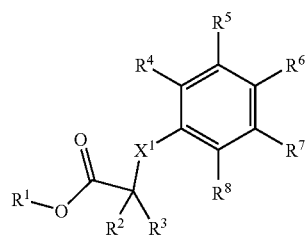

VI wherein $R^1$ is $C_{1-7}$-alkyl, $R^2$ to $R^8$ are as defined as in claim 1 and one of $R^5$, $R^6$ or $R^7$ is —(CH$_2$)$_p$—COOH, and p is defined as in claim 1, with a compound of formula

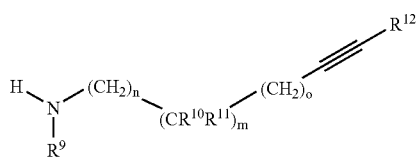

VII wherein $R^9$, $R^{10}$, $R^{11}$, $R^{12}$, m,n and o are as defined in claim 1, to obtain a compound of formula

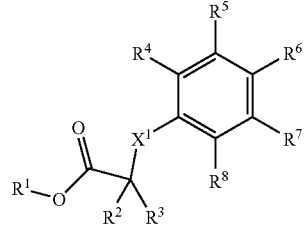

I-3 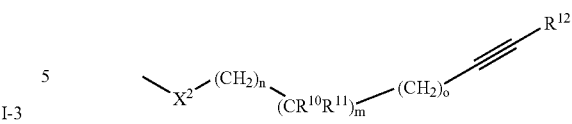

wherein one of $R^5$, $R^6$ and $R^7$ is and wherein $X^2$ is —$(CH_2)_p$—$CONR^9$, $R^1$ is $C_{1-7}$-alkyl and $X^1$, $R^2$ to $R^{12}$ and m, n, o and p are as defined in claim 1, and optionally hydrolyzing the ester group to obtain a compound of formula I, wherein $R^1$ is hydrogen.

22. A pharmaceutical composition comprising a therapeutically effective amount of a compound according to claim 1 and a pharmaceutically acceptable carrier and/or adjuvant.

23. A method for the treatment of diabetes, which method comprises administering a therapeutically effective amount of a compound according to claim 1 to a human being or animal in need thereof.

* * * * *

UNITED STATES PATENT AND TRADEMARK OFFICE
CERTIFICATE OF CORRECTION

PATENT NO.         : 7,253,192 B2                                       Page 1 of 1
APPLICATION NO.  : 11/172321
DATED              : August 7, 2007
INVENTOR(S)       : Jean Ackermann et al.

It is certified that error appears in the above-identified patent and that said Letters Patent is hereby corrected as shown below:

In Claim 2, Column 66, line 66 and Column 67, line 1, please delete "C3-7-cycloalkyl, halogen, C1-7-alkoxy-C1-7alkyl, C1-7- alkenyl, C1-7-alkinyl, fluoro-C1-7"

Insert -- C3-7-cycloalkyl, halogen, C1-7-alkoxy-C1-7 alkyl, C2-7-alkenyl, C2-7-alkinyl, fluoro-C1-7 --

Signed and Sealed this

Fifteenth Day of January, 2008

JON W. DUDAS
*Director of the United States Patent and Trademark Office*